(12) United States Patent
Ward et al.

(10) Patent No.: US 10,254,212 B2
(45) Date of Patent: *Apr. 9, 2019

(54) PARTICLE ANALYZING SYSTEMS AND METHODS USING ACOUSTIC RADIATION PRESSURE

(71) Applicant: LIFE TECHNOLOGIES CORPORATION, Carlsbad, CA (US)

(72) Inventors: Michael Ward, Eugene, OR (US); Gregory Kaduchak, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,948

(22) Filed: Aug. 18, 2016

(65) Prior Publication Data

US 2017/0038288 A1 Feb. 9, 2017

Related U.S. Application Data

(60) Division of application No. 14/464,763, filed on Aug. 21, 2014, now Pat. No. 9,476,855, which is a
(Continued)

(51) Int. Cl.
*G01N 15/14* (2006.01)
*A61M 1/36* (2006.01)
(Continued)

(52) U.S. Cl.
CPC ....... *G01N 15/1404* (2013.01); *A61M 1/3678* (2014.02); *G01N 15/12* (2013.01); *G01N 21/64* (2013.01); *G01N 21/645* (2013.01); *G01N 27/447* (2013.01); *G01N 29/222* (2013.01); *G01N 33/56966* (2013.01); *G01N 15/147* (2013.01); *G01N 21/1702* (2013.01); *G01N 21/6428* (2013.01); *G01N 2015/142* (2013.01); *G01N 2015/1409* (2013.01); *G01N 2015/1415* (2013.01); *G01N 2291/02416* (2013.01); *G01N 2291/02809* (2013.01); *G01N 2291/02836* (2013.01); *Y10T 436/101666* (2015.01); *Y10T 436/25* (2015.01); *Y10T 436/2575* (2015.01);
(Continued)

(58) Field of Classification Search
None
See application file for complete search history.

(56) References Cited

U.S. PATENT DOCUMENTS 3,882,732 A 5/1975 Fletcher et al.
4,055,491 A 10/1977 Porath-Furedi
(Continued)

FOREIGN PATENT DOCUMENTS

DE 3027433 2/1982
EP 0147032 7/1985
(Continued)

OTHER PUBLICATIONS

Aboobaker, N. et al. "Mathematical modeling of the movement of suspended particles subjected to acoustic and flow fields.", Applied Mathematical Modelling, vol. 29, 2005, pp. 515-532.
(Continued)

*Primary Examiner* — Xiaoyun R Xu
(74) *Attorney, Agent, or Firm* — Baker & Hostetler LLP

(57) ABSTRACT

The present invention comprises methods and systems that use acoustic radiation pressure.

20 Claims, 27 Drawing Sheets

Related U.S. Application Data continuation of application No. 12/239,453, filed on Sep. 26, 2008, now Pat. No. 8,846,408, which is a continuation-in-part of application No. PCT/US2008/059181, filed on Apr. 2, 2008.

(60) Provisional application No. 61/026,082, filed on Feb. 4, 2008, provisional application No. 60/909,704, filed on Apr. 2, 2007.

(51) Int. Cl.
  G01N 29/22 (2006.01)
  G01N 21/64 (2006.01)
  G01N 15/12 (2006.01)
  G01N 27/447 (2006.01)
  G01N 33/569 (2006.01)
  G01N 21/17 (2006.01)

(52) U.S. Cl.
  CPC ............... Y10T 436/25375 (2015.01); Y10T 436/25625 (2015.01)

(56) References Cited

U.S. PATENT DOCUMENTS

| | | |
|---|---|---|
| 4,265,124 A | 5/1981 | Lim et al. |
| 4,285,810 A | 8/1981 | Kirkland et al. |
| 4,350,683 A | 9/1982 | Galfre et al. |
| 4,434,230 A | 2/1984 | Ritts |
| 4,492,752 A | 1/1985 | Hoffman et al. |
| 4,523,682 A | 6/1985 | Barmatz et al. |
| 4,523,982 A | 6/1985 | Lee |
| 4,604,542 A | 8/1986 | Thompson |
| 4,673,512 A | 6/1987 | Schram |
| 4,743,361 A | 5/1988 | Schram |
| 4,759,775 A | 7/1988 | Peterson et al. |
| 4,777,823 A | 10/1988 | Barmatz et al. |
| 4,845,025 A | 7/1989 | Lary et al. |
| 4,867,559 A | 9/1989 | Bach |
| 4,877,516 A | 10/1989 | Schram |
| 4,913,883 A | 4/1990 | Imai et al. |
| 4,964,303 A | 10/1990 | Barmatz et al. |
| 4,979,824 A | 12/1990 | Mathies et al. |
| 4,983,189 A | 1/1991 | Peterson et al. |
| 4,987,086 A | 1/1991 | Brosnan et al. |
| 5,006,266 A | 4/1991 | Schram |
| 5,030,002 A | 7/1991 | North |
| 5,032,381 A | 7/1991 | Bronstein et al. |
| 5,040,890 A | 8/1991 | North |
| 5,079,959 A | 1/1992 | Miyake et al. |
| 5,085,783 A | 2/1992 | Feke et al. |
| 5,164,094 A | 11/1992 | Stuckart |
| 5,225,089 A | 7/1993 | Benes et al. |
| 5,264,906 A | 11/1993 | Ferer et al. |
| 5,346,670 A | 9/1994 | Renzoni et al. |
| 5,376,551 A | 12/1994 | Yoshikami |
| 5,395,588 A | 3/1995 | North et al. |
| 5,430,541 A | 7/1995 | Sapp et al. |
| 5,491,344 A | 2/1996 | Kenny et al. |
| 5,504,337 A | 4/1996 | Lakowicz et al. |
| 5,527,460 A | 6/1996 | Trampler et al. |
| 5,528,045 A | 6/1996 | Hoffman et al. |
| 5,547,849 A | 8/1996 | Baer et al. |
| 5,626,767 A | 5/1997 | Trampler et al. |
| 5,644,388 A | 7/1997 | Maekawa et al. |
| 5,674,698 A | 10/1997 | Zarling et al. |
| 5,688,406 A | 11/1997 | Stuart et al. |
| 5,711,888 A | 1/1998 | Trampler et al. |
| 5,739,902 A | 4/1998 | Gjelsnes et al. |
| 5,747,349 A | 5/1998 | van den Engh et al. |
| 5,798,222 A | 8/1998 | Goix |
| 5,800,861 A | 9/1998 | Chiang et al. |
| 5,831,166 A | 11/1998 | Kozuka et al. |
| 5,915,925 A | 6/1999 | North, Jr. |
| 5,981,180 A | 11/1999 | Chandler et al. |
| 5,994,089 A | 11/1999 | Siiman et al. |
| 6,003,388 A | 12/1999 | Oeftering |
| 6,049,380 A | 4/2000 | Goodwin et al. |
| 6,055,859 A | 5/2000 | Kozuka et al. |
| 6,074,879 A | 6/2000 | Zelmanovic et al. |
| 6,090,295 A | 7/2000 | Karumanchi et al. |
| 6,197,593 B1 | 3/2001 | Deka et al. |
| 6,216,538 B1 | 4/2001 | Yasuda et al. |
| 6,221,258 B1 | 4/2001 | Feke et al. |
| 6,248,590 B1 | 6/2001 | Malachowski |
| 6,255,118 B1 | 7/2001 | Alfano et al. |
| 6,309,886 B1 | 10/2001 | Ambrose et al. |
| 6,332,541 B1 | 12/2001 | Coakley et al. |
| 6,348,687 B1 | 2/2002 | Brockmann et al. |
| 6,373,567 B1 | 4/2002 | Wise et al. |
| 6,432,630 B1 | 8/2002 | Blankenstein |
| 6,449,563 B1 | 9/2002 | Dukhin et al. |
| 6,467,350 B1 | 10/2002 | Kaduchak et al. |
| 6,549,275 B1 | 4/2003 | Cabuz et al. |
| 6,565,727 B1 | 5/2003 | Shenderov et al. |
| 6,592,821 B1 | 7/2003 | Wada et al. |
| 6,644,118 B2 | 11/2003 | Kaduchak et al. |
| 6,649,414 B1 | 11/2003 | Chandler |
| 6,683,314 B2 | 1/2004 | Oostman et al. |
| 6,713,019 B2 | 3/2004 | Ozasa et al. |
| 6,773,556 B1 | 8/2004 | Brockie et al. |
| 6,797,158 B2 | 9/2004 | Feke et al. |
| 6,813,017 B1 | 11/2004 | Hoffman et al. |
| 6,816,257 B2 | 11/2004 | Goix |
| 6,831,279 B2 | 12/2004 | Ho |
| 6,881,314 B1 | 4/2005 | Wang et al. |
| 7,008,540 B1 | 3/2006 | Weavers et al. |
| 7,018,819 B2 | 3/2006 | Orwar et al. |
| 7,052,864 B2 | 5/2006 | Durkop et al. |
| 7,081,192 B1 | 7/2006 | Wang et al. |
| 7,091,348 B2 | 8/2006 | O'Neill et al. |
| 7,108,137 B2 | 9/2006 | Lal et al. |
| 7,113,266 B1 | 9/2006 | Wells |
| 7,161,665 B2 | 1/2007 | Johnson |
| 7,255,780 B2 | 8/2007 | Shenderov |
| 7,262,838 B2 | 8/2007 | Fritz et al. |
| 7,315,357 B2 | 1/2008 | Ortyn et al. |
| 7,329,545 B2 | 2/2008 | Pamula et al. |
| 7,340,957 B2 | 3/2008 | Kaduchak et al. |
| 7,362,432 B2 | 4/2008 | Roth |
| 7,373,805 B2 | 5/2008 | Hawkes et al. |
| 7,403,125 B2 | 7/2008 | Rich |
| 7,477,363 B2 | 1/2009 | Nagai |
| 7,570,676 B2 | 8/2009 | Essaian |
| 7,758,811 B2 | 7/2010 | Durack et al. |
| 7,837,040 B2 | 11/2010 | Ward et al. |
| 7,990,525 B2 | 8/2011 | Kanda |
| 8,227,257 B2 | 7/2012 | Ward et al. |
| 8,486,371 B2 | 7/2013 | Ye et al. |
| 2002/0121285 A1 | 9/2002 | Poniatowski et al. |
| 2002/0129669 A1 | 9/2002 | Buchanan |
| 2002/0162393 A1 | 11/2002 | Kaduchak et al. |
| 2003/0030783 A1 | 2/2003 | Roche et al. |
| 2003/0059850 A1 | 3/2003 | Evans |
| 2003/0098421 A1 | 5/2003 | Ho |
| 2003/0134416 A1 | 7/2003 | Yamanishi et al. |
| 2003/0162393 A1 | 8/2003 | Sato et al. |
| 2004/0057866 A1 | 3/2004 | Zumeris et al. |
| 2004/0069717 A1 | 4/2004 | Laurell et al. |
| 2004/0106215 A1 | 6/2004 | Lehmann |
| 2004/0139792 A1 | 7/2004 | Cobb |
| 2004/0142463 A1 | 7/2004 | Walker et al. |
| 2005/0072677 A1 | 4/2005 | Gascoyne et al. |
| 2005/0112541 A1 | 5/2005 | Durack |
| 2005/0223427 A1 | 10/2005 | Leake et al. |
| 2006/0021437 A1 | 2/2006 | Kaduchak et al. |
| 2006/0034733 A1 | 2/2006 | Ferren et al. |
| 2006/0163166 A1 | 7/2006 | Hawkes et al. |
| 2007/0037172 A1 | 2/2007 | Chiu et al. |
| 2007/0071683 A1 | 3/2007 | Dayton et al. |
| 2007/0098232 A1 | 5/2007 | Matula |
| 2007/0119239 A1 | 5/2007 | Priev et al. |
| 2007/0263693 A1 | 11/2007 | Essaian et al. |
| 2008/0053787 A1 | 3/2008 | Bagajewicz |

(56) References Cited

U.S. PATENT DOCUMENTS

| | | | |
|---|---|---|---|
| 2008/0106736 A1 | 5/2008 | Graves et al. |
| 2008/0245709 A1 | 10/2008 | Kaduchak et al. |
| 2008/0245745 A1 | 10/2008 | Ward et al. |
| 2009/0029870 A1 | 1/2009 | Ward et al. |
| 2009/0042239 A1 | 2/2009 | Ward et al. |
| 2009/0042310 A1 | 2/2009 | Ward et al. |
| 2009/0045107 A1 | 2/2009 | Ward et al. |
| 2009/0048805 A1 | 2/2009 | Kaduchak et al. |
| 2009/0050573 A1 | 2/2009 | Ward et al. |
| 2009/0053686 A1 | 2/2009 | Ward et al. |
| 2009/0107241 A1 | 4/2009 | Goddard et al. |
| 2009/0139332 A1 | 6/2009 | Goddard et al. |
| 2009/0158823 A1 | 6/2009 | Kaduchak et al. |
| 2009/0162887 A1 | 6/2009 | Kaduchak et al. |
| 2009/0178716 A1 | 7/2009 | Kaduchak et al. |
| 2009/0227042 A1 | 9/2009 | Gauer et al. |
| 2009/0316151 A1 | 12/2009 | Matula et al. |
| 2010/0000325 A1 | 1/2010 | Kaduchak et al. |
| 2010/0009333 A1 | 1/2010 | Auer |
| 2010/0248284 A1 | 9/2010 | Chen et al. |
| 2011/0024335 A1 | 2/2011 | Ward et al. |
| 2011/0032522 A1 | 2/2011 | Graves et al. |
| 2011/0134426 A1 | 6/2011 | Kaduchak et al. |

FOREIGN PATENT DOCUMENTS

| | | |
|---|---|---|
| EP | 0292470 | 5/1988 |
| EP | 0703296 | 3/1996 |
| EP | 0773055 | 5/1997 |
| FR | 821419 | 12/1937 |
| JP | S63139231 | 6/1988 |
| JP | H01-112161 | 4/1989 |
| JP | H06241977 | 9/1994 |
| JP | H08266891 | 10/1996 |
| JP | H11-014533 | 1/1999 |
| RU | 2224992 | 2/2004 |
| WO | 1988009210 | 12/1988 |
| WO | 1990005008 | 5/1990 |
| WO | 1994029695 | 12/1994 |
| WO | 1997002482 | 1/1997 |
| WO | 2000041794 | 7/2000 |
| WO | 2002059577 | 8/2002 |
| WO | 2002072234 | 9/2002 |
| WO | 2002072236 | 9/2002 |
| WO | 2003079006 | 9/2003 |
| WO | 2004024287 | 3/2004 |
| WO | 2004033087 | 4/2004 |
| WO | 2006076195 | 7/2006 |
| WO | 2007128795 | 11/2007 |
| WO | 2008122051 | 10/2008 |
| WO | 2009091925 | 7/2009 |
| WO | 2011068764 | 6/2011 |

OTHER PUBLICATIONS

Aleksandrov, M. et al. "Pulsed laser fluoresence spectrometer", translation from Zhurnal Prikladnoi Spektroskopii,47, 1987, pp. 686-692.

Anderson, M. et al. "The Physics and Technology of Ultrasonic Particle Separation in Air", WCU 2003, Paris, Sep. 7-10, 2003, pp. 1615-1621.

Apfel, R. "Acoustic Radiation Pressure—Principles and Application to Separation Science", Fortschritte Der Akustik DAGA '90, 1990, pp. 19-30.

Araz, M. et al. "Ultrasonic Separation in Microfluidic Capillaries", IEEE Ultrasonics Symposium, 2003, pp. 1066-1069.

Asai, K. "Ultrasonic treatment of slurry", Third International Coal Preparation Conference, 1958, pp. 518-527.

Bardsley, et al. "Electroacoustic production of murine hybridomas", Journal of Immunological;Methods,vol. 129 (1), 1990, pp. 41-47.

Barmatz, M et al. "Acoustic radiation potential on a sphere in plane, cylindrical, and spherical standing wave fields.", J. Acoust. Soc. Am. vol. 77, 1985, pp. 928-945.

Bauerecker, Sigurd et al. "Formation and growth of ice particles in stationary ultrasonic fields", J of Chem Phys, 1998, pp. 3709-3712.

Bazou, D et al. "Physical Environment of 2-D Animal Cell Aggregates Formed in a Short Pathlength Ultrasound Standing Wave Trap", Ultrasound in Med & Biol, vol. 31, 2005, pp. 423-430.

Benes, E. et al. "Absheidung Dispergieter Teilchen Durch Ultraschall-Induzierte Koagulation", Tagung der Deutschen Arbeitsgameinschaft fur Akustik—DAGA '89, 1989, pp. 1-4.

Benes, E. et al. "Improved quartz crystal microbalance technique", Journal of Applied Physics, vol. 56, 1984, pp. 608-626.

Benes, E. et al. "Separation of Dispersed Particles by Ultrasonic-Induced Coagulation", 15th Conference of the German Society for Acoustics, 1989, p. 2.

Beverloo, H. et al. "Inorganic Phosphors asNew Luminescent Labels for Immunocytochemistry andTime-Resolved Microscopy", Cytometry, vol. 11, 1990, pp. 784-792.

Bienvenue, J. et al. "Microchip-Based Cell Lysis and DNA Extraction from Sperm Cells for Application to Forensic Analysis", J. Forensic Sci. vol. 51, 2006, pp. 266-273.

Binks, B. et al. "Modern Aspects of Emulsion Science", The Royal Society of Chemistry, 1998, pp. 310-321.

BIOSEP: The Advanced Acoustic Cell Retention Device, Technical Data Sheet: STS90; AppliSens Sensor Innovation, Applikon Dependable Instruments by, The Netherlands, Downloaded Jun. 20, 2011, 2002, 12 pages.

Bishop, J. et al. "Mechanism of higher brightness of PerCP-Cy5.5", Cytometry Supp, vol. 10, 2000, pp. 162-163.

Borgnis, F. "Acoustic Radiation Pressure of Plane Compressional Waves", Review of Modern Physics, vol. 25, 1953, pp. 653-664.

Borisov, S. et al. "Blue LED Excitable Temperature Sensors Based on a New Eurpium (III) Chelate", J. Fluoresc, vol. 18, Feb. 21, 2008, pp. 581-589.

Borthwick, K. et al. "Development of a novel compact sonicator for cell disruption", Journal of Microbiological Methods, vol. 60, 2005, pp. 207-216.

Bosma, R. et al. "Ultrasound, a new separation technique to harvest microalgae", Journal of Applied Phycology, vol. 15, 2003, pp. 143-153.

Bossuyt, X. et al. "Comparative Analysis for Whole Blood Lysis Methods for Flow Cytometry", Cytometry, vol. 30, 1997, pp. 124-133.

Brodeur, P. "Acoustic Separation in a Laminar Flow", Ultrasonics Symposium, IEEE, 1994, pp. 1359-1362.

Caperan, P. et al. "Acoustic Agglomeration of a Glycol Fog Aerosol: Influence of Particle COncentration and Intensity of the Sound Field at Two Frequencies", J. Aerosol Sci, vol. 26, 1995, pp. 595-612.

Chase, E. et al. "Resolution of Dimly Fluorescent Particles: A Practical Measure of Fluoresence Sensitivity", Cytometry, vol. 33, 1998, pp. 267-279.

Cheung, K. et al. "Impedance spectroscopy flow cytometry: on-chip label-free cell diffeentiation", 2005, Cytometry Part A, vol. 65A, pp. 124-132. 2005, pp. 124-132.

Coakley, W. et al. "Analytical scale ultrasonic standing wave manipulation of cells and microparticles", Ultrasonics, vol. 38, 2000, pp. 638-641.

Coakley, W. et al. "Ultrasonic separations in analytical biotechnology", Tibtech, vol. 15, 1997, pp. 506-511.

Coakley, W. et al. "Cell-cell contact and membrande spreading in an ultrasound trap", Colloids and Surfaces B: Biointerfaces, vol. 34, 2004, pp. 221-230.

Condrau, M. et al. "Time-Resolved Flow Cytometry for the Measurement of Lanthanide Chelate Fluoresence: I. Concept and Theoretical Evaluation", Cytometry, vol. 16, 1994, pp. 187-194.

Condrau, M. et al. "Time-Resolved Flow Cytometry for the Measurement of Lanthanide Chelate Fluoresence: II. Instrument Design and Experimental Results", Cytometry, vol. 16, 1994, pp. 195-205.

Cousins, C. et al. "Plasma Preparation from Whole Blood Using Ultrasound", Ultrasound in Med & Biol, vol. 26, 2000, pp. 881-888.

Curtis, H. et al. "Ultrasonic COntinuous Flow Plasmapheresis Separator", IBM Tech. Disc. Bulletin, vol. 25, 1982, pp. 192-193.

Czyz, H. "On the Concentration of Aerosol Particles by Means of Drift Forces in a Standing Wave Field", Acustica, vol. 70, 1990, pp. 23-28.

(56) References Cited

OTHER PUBLICATIONS

Dain, Y. et al. "Dynamics of Suspended Particles in a Two-Dimensional High-Frequency Sonic Field", J. Aerosol Sci, vol. 26, 1995, pp. 575-594.
Dain, Y. "Side drift of aerosols in two-dimensional resonant acoustic levitators", J Acoust SOc Am, vol. 102, 1997, pp. 2549-2555.
Danilov, S. et al. "Mean force on a small sphere in a sound field in a viscous fluid", J Acoust Soc Am, vol. 107, 2000, pp. 143-153.
Danilov, S. et al. "The Mean Force Acting on a Small Body in an Axisymetric Sound Field in a Real Medium", Izvestiya Adademii Nauk SSSR, Mekhanika Zhidkosti I Gaza vol. 5, 1985, pp. 812-820.
Dean, P. et al. "Hydrodynamic Orientation of Sperm Heads for Flow Cytometry", Biophys J, vol. 23, 1978, pp. 7-13.
Doblhoff-Dier, O. et al. "A Novel Ultrasonic Resonance Field Device for the Retention of Animal Cells", Biotechnol Prog, vol. 10, 1994, pp. 428-432.
Doinikov, A. et al. "Acoustic radiation force on a spherical particle in a viscous heat-conducting fluid. I. General formula", J. Acoust Soc Am, vol. 101, 1997, pp. 713-721.
Doinikov, A. et al. "Acoustic radiation force on a spherical particle in a viscous heat-conducting fluid. II. Force on a rigid sphere.", J Acoust Soc Am, vol. 101, 1997, pp. 722-730.
Doinikov, A. et al. "Acoustic radiation force on a spherical particle in a viscous heat-conducting fluid. III. Force on a liquid drop", J. Acoust. Soc Am, vol. 101, 1997, pp. 731-740.
Doinikov, A. et al. "Acoustic radiation pressure on a rigid sphere in a viscous fluid", Proceedings Royal Society of London, vol. 447, 1994, pp. 447-466.
Donnert, G. et al. "Major signal increase in fluoresence microscopy through dark-state relaxation", Nature Methods, vol. 4, 2007, pp. 81-86.
Doornbos, R. et al. "Experimental and Model Investigations of Bleaching and Saturation of Fluoresence in Flow Cytometry", Cytometry, vol. 29, 1997, pp. 204-214.
Fenniri, H. et al. "Classification of Spectrscopically Encoded Resins by Raman Mapping and Infrared Hyperspectral Imaging", Journal of Combinatorial Chemistry, vol. 8, 2006, pp. 192-198.
Fulwyler, M. et al. "Hydronamic Orientation of Cells", Histochem Cytoche, vol. 7, 1977, pp. 781-783.
Gaida, T. et al. "Selective Retention of Viable Cells in Ultrasonic Resonance Field Devices", Biotech Prog, vol. 12, 1996, pp. 73-76.
Gallego, J. et al. "Piezoelectric Transducer for Air-Borne Ultrasound", Acustica, vol. 29, 1973, pp. 234-239.
Gao, X. et al. "Quantum Dot-Encoded Mesoporous Beads with High Brightness and Uniformity: Rapid Readout Using Flow Cytometry", Anal Chem, vol. 76, 2004, pp. 2406-2410.
Gawad, S. et al. "Micromachined impedance spectroscopy flow cytometer for cell analysis and particle sizing", Lab on a Chip, vol. 1, 2001, pp. 76-82.
Gherardini, L et al. "A New Immobilisation Method to Arrange Particles in a Gel Matrix by Ultrasound Standing Waves", Ultrasound in Med & Biol. vol. 31, 2005, pp. 261-272.
Goddard, G. et al. "Ultrasonic particle-concentration for sheathless focusing of particles for analysis in a flow cytometer", Cytometry Part A, 69A, 2006, pp. 66-74.
Goddard, G. et al. "Ultrasonic Concentration in a Line Driven Cylindrical Tube", Dissertation, 2004, pp. 1-276.
Goddard, G. et al. "Single Particle High Resolution Spectral Analysis Flow Cytometry", Cytometry, vol. 69A, 2006, pp. 842-851.
Goddard, G. et al. "Ultrasonic particle concentration in a line-driven cylindrical tube", J. Acoust. Soc. Am, vol. 117, 2005, pp. 3440-3447.
Gonzalez, I. et al. "Precise Measurements of Particle Entertainment in a Standing-Wave Acoustic Field Between 20 and 3500 Hz", J Aerosol Sci, vol. 31, 2000, pp. 1461-1468.
Gor'Kov, L. et al. "On the Forces Acting on a Small Particle in an Acoustical Field in an Ideal Fluid.", Soviet Physics-Doklady, vol. 6, 1962, pp. 773-775.
Gould, R. et al. "The effects of acoustic forces on small aprticles in suspension", Proceedings of the 1973 Symposium on Finite Amplitude Wave Effects in Fluids, Bjorno, L. ed. Pergamon, Guildford, 1974, pp. 252-257.
Gould, R. et al. "Upper sound pressure limits on particle concentration in fields of ultrasonic standing-wave at megahertz frequencies", Ultrasonics, vol. 30, 1992, pp. 239-244.
Groschl, M. et al. "Automatische Frequenzregelung fur Piezoelektrische Resonatoren und deren Implementierung in akustischen Driftwellenresonator", Diplomarbeit Institut fur Allgemeine Physik, Technishchen Universitat Wien, 1991, pp. 1-132.
Groschl, M. et al. "Automatic Frequency Control for Piexoelectric Resonators and their Implementation in the Acoustic Driftwave Resonator", Thesis implemented at the Institute for General Physics at the Technical University of Vienna, 1991, pp. 1-132
Grossner, M. et al. "Single-Collector Experiments and Modeling of Acoustically Aided Mesh Filtration", American institute of Chemical Engineering Journal, vol. 51, No. 6, 2005, pp. 1590-1598.
Grossner, M. et al. "Single fiber model of particle retention in an acoustically driven porous mesh", Ultrasonics, vol. 41, 2003, pp. 65-74.
Grossner, M. T. et al. "Transport analysis and model for the performance of an ultrasonically enhanced filtration process", Chem. Eng. Sci, vol. 60, 2005, pp. 3233-3238.
Gupta, S. et al. "Acoustically driven collection of suspended particles within porous media", Ultrasonics, vol. 35, 1997, pp. 131-139.
Gupta, S. et al. "Fractionation of Mixed Particulate Solids According to Compressibility Using Ultrasonic Standing Wave Fields", Chem Eng Sci, vol. 50, 1995, pp. 3275-3284.
Haake, A. et al. "Manipulation of Cells Using an Ultrasonic Pressuer Field", Ultrasound in Med & Biol, vol. 31, 2005, pp. 857-864.
Haake, A. et al. "Positioning of small particles by an ultrasound field excited by surface waves", Ultrasonics, vol. 42, 2004, pp. 75-80.
Haake, A. et al. "Contactless micromanipulation of small particles by an ultrasound field excited by a vibrating body", J. Acoust Soc Am, vol. 117, 2005, pp. 2752-2760.
Haake, A. et al. "Positioning, Displacement, and Localization of Cells Using Ultrasonic Forces", Biotechnology and Bioengineering, vol. 92, No. 1, 2005, pp. 8-14.
Habbersett, R. et al. "An Analytical System Based on a Compact Flow Cytometer for DNA Fragment Sizing and Single Molecule Detection", Cytometry, vol. 60A, 2004, pp. 125-134.
Hager, F. et al. "A Summary of All Forces Acting on Spherical Particles in a Sound Field", Proc of the Ultrasonic International '91 Conference and Exhibition, Le Touquet, France, 1991, pp. 1-4.
Hamilton, M. et al. "Acoustic streaming generated by standing waves in two-dimensional channels of arbitrary width", J. Acoust SOc Am, vol. 113, 2003, pp. 153-160.
Hamilton, M. et al. "Linear and nonlinear frequency shifts in acoustical resonators with varying cross sections", J. Acoust SOc Am, vol. 110, 2001, pp. 109-119.
Hancock, A. "Observation of Forces on Microparticles in Acoustic Standing Waves", Thesis, 2001, pp. 1-139.
Harma, H. et al. "Zeptomole detection sensitivity of prostate-specific antigen in a rapid microtitre plate assay using time-resolved fluoresence", Luminescence, vol. 15, 2000, pp. 351-355.
Harris, N. et al. "A silicon microfluidic ultrasonic separator", Sensors and Actuators, vol. 95, 2003, pp. 425-434.
Harrison, B. et al. "Near-Infrared Photo- and Electroluminescence of Alkoxy-Substituted Poly (p-phenylene) and Nonconjugated Polymer/Lanthanide Tetraphenylporphyrin Blends", Chemistry of Materials, vol. 16, 2004, pp. 2938-2947.
Hatanaka, S. et al. "Effect of Process Parameters on Ultrasonic Separation of Dispersed Particles in Liquid", Jpn J Appl Phys, vol. 38, 1999, pp. 3096-3100.
Hawkes, J. et al. "Continuous cell washing and mixing driven by an ultrasound standing wave within a microfluidic channel", Lab on a Chip, vol. 4(5), 2004, pp. 446-452.
Hawkes, J. et al. "Force field particle filter, combining ultrasound standing waves and laminar flow", Sensors and Actuators B, vol. 75, 2001, pp. 213-222.

(56) References Cited

OTHER PUBLICATIONS

Hawkes, J. et al. "Microparticle manipulation in millimetre scale ultrasonic standard wave chambers", Ultrasonics, vol. 36, 1998, pp. 925-931.

Hawkes, J. et al. "Single half-wavelength ultrasonic particle filter: Predictions of the transfer matrix multilayer resonator model and experimental filtration results", J Acoust Soc Am, vol. 111, 2002, pp. 1259-1266.

Hawkes, J. et al. "A laminar flow expansion chamber facilitating downstream manipulation of particles concentrated using an ultrasonic standing wave", Ultrasonics, vol. 36, 1998, pp. 901-903.

Hawkes, J. et al. "Ultrasonic deposition of cells on a surface.", Biosensors and Bioelectronics, vol. 19, 2004, pp. 1021-1028.

Hemmila, I. et al. "Progress in Lanthanides as Luminescent Probes", J. Fluoresence, vol. 15, 2005, pp. 529-542.

Hertz, H. et al. "Standing-wave acoustic trap for nonintrusive positioning of microparticles", J. Appl. Phys, vol. 78, 1995, pp. 4845-4849.

Higashitani, K. et al. "Migration of Suspended Paticles in Plane Stationary Ultrasonic Field", Chem. Eng. Sci, vol. 36, 1981, pp. 1187-1192.

Hill, D. et al. "Operating Characteristics of Acoustically Driven Filtration Processes for Particulate Suspensions", Sep. Sci. and Tech. vol. 35, 2000, pp. 1363-1375.

Hill, M. et al. "Modelling in the design of a flow-through ultrasonic separator", Ultrasonics, vol. 38, 2000, pp. 662-665.

Hill, M. et al. "Modelling of layered resonators for ultrasonic separation", Ultrasonics, vol. 40, 2002, pp. 385-392.

Hill, M. "The selection of layer thicknesses to control acoustic radiation forces profiles in layered resonators", J. Acoust Soc Am, vol. 114, No. 5, 2003, pp. 2654-2661.

Hirschfeld, T. et al. "Fluoresence Background Discrimination by Prebleaching", J. Histochem and Cytochem, vol. 27, 1979, pp. 96-101.

Holmes, D. et al. "High throughput particle analysis: Combining dielectrophoretic particle focusing with confocal optical detection", Biosensors and Bioelectronics, vol. 21, 2006, pp. 1621-1630.

Holwill, I. et al. "The use of ultrasonic standing waves to enhance optical particle sizing equipment", Ultrasonics, vol. 38, 2000, pp. 650-653.

Huhtinen, P. et al. "Synthesis, Characterization, and Application of Eu(III), Tb(III), Sm(III), and Dy(III) Lanthanide Chelate Nanoparticle Labels", Anal Chem, vol. 77, 2005, pp. 2643-2648.

Invitrogen, "Fluorophore selection guide for flow cytometry", Cellular Analysis, 2007, 31 pages.

Johnston, P. et al. "Cellular platforms for HTS: three case studies", DDT, vol. 7, 2002, pp. 353-363.

Jonsson, H. et al. "Particle separation using ultrasound can be used with human shed mediastinal blood", Perfusion, vol. 20, 2005, pp. 39-43.

Kaduchak, G. et al. "E6 diffraction catastrophe of the primary rainbow of oblate water drops: observations with white-light and laser illumination", Applied Optics, vol. 33, 1994, pp. 4691-4696.

Kaduchak, G. et al. "Hyperbolic umbilic and E6 diffraction catastrophes associated with the secondary rainbow of oblate water drops: observations with laser illumination", Applied Optics, vol. 33, 1994, pp. 4697-4701.

Kapishnikov, S. et al. "Continuous particle size separation and size sorting using ultrasound in a microchannel", J Stat Mech, 2006, 1-13.

Karumanchi, R. "Field-assisted extraction of cells, particles and macromolecules", Trends in Biotech, vol. 20, 2002, pp. 72-78.

Kaye, P. et al. "Spatial light-scattering analysis as a means of characterizing and classifying non-spherical particles", Meas Sci Technol, vol. 9, 1998, pp. 141-149.

Keij, J. et al. "Coincidence in high-speed flow cytometry: models and measurements", Cytometry, vol. 12, pp. 398-404, 1991, pp. 398-404.

Kilburn, D. et al. "Enhanced Sedimentation of Mammalian Cells following Acoustic Aggregation", Biotech and Bioeng, vol. 34, 1989, pp. 559-562.

King, L. et al. "On the acoustic radiation on spheres", Proceedings Royal Society A. vol. 147, 1933, pp. 212-240.

Kogan, S. et al. "Acoustic concentration of particles in piezoelectric tubes: Theoretical modeling of the effect of cavity shape and symmetry breaking", J. Acoust Soc Am, vol. 116, 2004, pp. 1967-1974.

Kozuka, T. et al. "Acoustic Micromanipulation Using a Multi-Electrode Transducer", 7th Inter Symp on Micro Machine and Human Science, 1996, pp. 163-170.

Kozuka, T. et al. "Control of a Standing Wave Field Using a Line-Focused Transducer for Two-Dimensional Manipulation of Particles", Jpn. J. Appl. Phys, vol. 37, 1998, pp. 2974-2978.

Kozuka, T. et al. "Micromanipulation Using a Focused Ultrasonic Standing Wave Field", Electronics and Communications in Japan, vol. 83, No. 1. Translated from Denshi Joho Tsushin Gakkai Ronbunshi, vol. J80-A, No. 10, 1997, pp. 1654-1659.

Kumar, et al. "Fractionation of Cell Mixture Using Acoustic and Laminar Flow Fields", Biotech. Bioeng. vol. 89, 2004, pp. 129-137.

Kundt, A. et al. "Longitudinal vibrations and acoustic figures in cylindrical columns of liquids", Annalen der Physik und Chemie (Poggendorff's Annalen), vol. 153, 1874, pp. 1-12.

Kuznetsova, L. et al. "Cavitation buble-driven cell and particle behavior in a ultrasound standing wave", J. Acoust Soc Am, vol. 117, 2005, pp. 104-112.

Kuznetsova, L. et al. "Microparticle concentration in short path length ultrasonic resonators: Roles of radiation pressure and acoustic streaming", J. Acoust Soc Am, vol. 116, 2004, pp. 1956-1966.

Kwiatkowski, C. et al. "Resonator frequency shift due to ultrasonically induced microparticle migration in an aqueous suspension: Observations and model for the maximum frequency shift", J. Acoust. Soc. Am, vol. 103, 1998, pp. 3290-3300.

Lakowicz, J. et al. "On the Possibility of Long-Wavelength Long-Lifetime High-Quantum-Yield Luminophores", Analytical Biochemistry, vol. 288, 2001, pp. 62-75.

Leif, R. et al. "Markers for Instrumental Evaluation of Cells of the Female Reproductive Tract; Existing and New Markers", The Automation of Uterine Cancer Cytology, edited by G.L. Wied, G.F. Babr, P.H. Bartels, 1976, pp. 313-344.

Leif, Robert C. et al. "Increasing the Luminescence of Lanthanide Complexes", Cytometry, vol. 69A, 2006, pp. 767-778.

Lierke, E. G. et al. "Acoustic Positioning for Space Processing of Materials Science Samples in Mirror Furnaces", IEE Ultrasonics Symposium, 1983, pp. 1129-1139.

Lilliehorn, T et al. "Trapping of microparticles in the rear field of an ultrasonic transducer", Ultrasonics, vol. 43, 2005, pp. 293-303.

Lofstedt, R. et al. "Theory of long wavelength acoustic radiation pressure", J Acoust Soc Am, vol. 90, 1991, pp. 2027-2033.

Loken, M. et al. "Cell Discrimination by Multiangle Light Scattering", Histochem Cytochem, vol. 24, 1976, pp. 284-291.

Loken, M. et al. "Identification of Cell Asymmetry and Orientation by Light Scattering", Histochem Cytochem, vol. 7, 1977, pp. 790-795.

Macey, M. et al. "The Q-Prep system: Effects on the apparent expression of leucocyte cell surface antigens", Cytometry Part A, Abstract, vol. 30(2), 1997, pp. 67-71.

Macey, M. et al. "Comparative Study of Five Commercial Reagents for Preparing Normal and Leikaemic Lymphocytes for Immunophenotypic Analysis by Flow Cytometry", Cytometry, vol. 38, 1999, pp. 153-160.

Maltsev, V. et al. "Scanning flow cytometry for individual particle analysis", Review of Scientific Instruments, vol. 71, 2000, pp. 243-255.

Mandralis, Z. et al. "Enhanced synchronized ultrasonic and flow-field fractionation of suspensions", Ultrasonics, vol. 32, 1994, pp. 113-121.

Mandralis, Z. et al. "Transient Response of Fine Particle Suspensions to Mild Planar Ultrasonic Fields", Fluid/Particle Separation Journal, vol. 3, 1990, pp. 115-121.

(56) References Cited

OTHER PUBLICATIONS

Marston, P. et al. "Manipulation of Fluid Objects with Acoustic Radiation Pressure", Ann. N.Y. Acad. Sci, vol. 1027, 2004, pp. 414-434.
Marston, P. et al. "Generalized rainbows and unfolded glories of oblate drops: organization for multiple internal reflection and extension of cusps into Alexander's dark band", Applied Optics, vol. 33, 1994, pp. 4702-4713.
Marston, P. et al. "Resonances, Radiation Pressure, and Optical Scatering Phenomena of Drops and Bubbles", JPL Pub, vol. 82, No. 7, 1982, pp. 166-174.
Marston, P. "Tensile Strength and Visible Ultrasonic Cavitation of Superfluid 4He*", Journal of Low Temperature Physics, vol. 25, Nos. 3/4, 1976, pp. 383-407.
Martin, K. et al. "Acoustic filtration and sedimentation of soot particles", Experiments in Fluids, vol. 23, 1997, pp. 483-488.
Masudo, T. et al. "Particle Characterization and Separation by a Coupled Acoustic-Gravity Field", Analytical Chemistry, vol. 73, 2001, pp. 3467-3471.
Mathies, R. et al. "Optimization of High-Sensitivity Fluoresence Detection", Anal Chem, vol. 62, 1990, pp. 1786-1791.
Mazumder, M. et al. "Single particle aerodynamic relaxation time analyzer", Rev Sci Instrum, vol. 48, 1977, pp. 622-624.
Mazumder, M. et al. "Spart Analyzer: Its Application to Aerodynamic Size Distribution Measurement", J. Aerosol Sci, vol. 10, 1979, pp. 561-569.
McCartin, B. "A Numerical Procedure for 2D Acoustic Waveguides with Heated Walls", Session C3—Education and Theory: ORAL session, downloaded at http://flux.aps.org/meetings/YR99/OSS99/abs/S700004.html, May 1, 1999, 1 page.
Meindersma, G. et al. "Separation of a biocatalyst with ultrafiltration or filtration after bioconversion", J Membrane Sci, vol. 125, 1997, pp. 333-349.
Molecular Probes, "Fluo-4 NW Calcium Assay Kits (F36205, F36206)", Product Information, Invitrogen Detection Technologies, Oct. 20, 2006, 5 pages.
Molecular Probes, "Handbook of Fluorescent Probes and Research Products", Chapter 6—Ultrasensitive Detection Technology, 6.5 FluoSpheres and TransFluoSpheres Fluorescent Microspheres; http:www.mobitec.com/probes/docs/sections/0605.pdf, 2002, 12 pages.
Morgan, J. et al. "Manipulation of in vitro toxicant sensors in an ultrasonic standing wave", Toxicology in Vitro, vol. 18, 2004, pp. 115-120.
Mullaney, P. et al. "The Small Angle Light Scattering of Biological Cells", Biophys Journal, vol. 10, 1970, pp. 764-772.
Neild, A. et al. "Design, modeling and characterization of microfluidic devices for ultrasonic manipulation", Sensors and Actuators B, vol. 121, 2007, pp. 452-461.
Neild, A. et al. "A micro-particle positioning technique combining an ultrasonic manipulator and a microgripper", J. Micromech. Microeng. 16, http://stacks.iop.org/JMM/16/1562, 2006, pp. 1562-1570.
Neild, Adrian et al. "Design, modeling and characterization of microfluidic devices for ultrasonic manipulation", Sensors and Actuators B, vol. 121, 2007, pp. 452-461.
Neukammer, J. et al. "Angular distribution of light scattered by single biological cells and oriented particle agglomerates", Appl Opt, vol. 42, 2003, pp. 6388-6397.
Nilsson, A. et al. "Acoustic control of suspended particles in micro fluidic chips", Lab Chip, vol. 4, 2004, pp. 131-135.
Nolan, J. et al. "Suspension array technology: new tools for gene and protein analysis.", Cell and Molecular Biology, vol. 47, No. 7, 2001, pp. 1241-1256.
Nowotny, H. "Layered piezoelectric resonators with an arbitrary number electrodes (general one-dimensional treatment)", J Acoust Soc Am, vol. 90, 1991, pp. 1238-1245.
Otaki, M. et al. "Virus Removal in a Membrane Separation Process", Water Sci and Tech, vol. 37, 1998, pp. 107-116.
Oxford, "Dictionary of Biochemistry and Molecular Biology Revised Edition", Lysis, 2006, p. 397.
Pangu, G. et al. "Acoustically aided separation of oil droplets from aqueous emulsions", Chem Eng Sci, vol. 59, 2004, pp. 3183-1393.
Petersson, F. et al. "Separation of lipids from blood utilizing ultrasonic standing waves in microfluidic channels", Analyst, vol. 129, 2004, pp. 938-943.
Petersson, F. et al. "Continuous separation of lipid particles from erythrocytes by means of laminar flow and acoustic standing wave forces", Lab Chip, vol. 5, 2005, pp. 20-22.
Petersson, F. et al. "Carrier medium exchange through ultrasonic particle switching in microfluidic channels", Analytical Chemistry, vol. 77(5), 2005, pp. 1216-1221.
Petersson, F. et al. "Free Flow Acoustophoresis: Microfluidic-Based Mode of Particle and Cell Separation", Anal Chem, vol. 79, 2007, pp. 5117-5123.
Petersson, F."Particle Flow Switch Utilizing Ultrasonic Particle Switching in Microfluidic Channels", 7th International Conf on Miniaturizing Chem and Biochem Analysis Systems, 2003, pp. 879-882.
Pregibon, D. et al. "Multifunctional Encoded Particles for High-Throughput Biomolecule Analysis", Science, vol. 315, 2007, pp. 1393-1396.
Princen, K. et al. "Evaluation of SDF-1/CXCR4-Induced Ca2+ Signaling by Fluorometric Imaging Plate Reader (FLIPR) and Flow Cytometry", Cytometry, vol. 51A, 2003, pp. 35-45.
Pui, P. et al. "Batch and Semicontinuous Aggregation and Sedimentation of Hybridoma Cells by Acoustic Resonance Fields", Biotechnol Prog, vol. 11, 1995, pp. 146-152.
Rao, G. et al. "Monodisperse Mesoporous Silica Microspheres Formed by Evaporation-Induced Self Assembly of Surfacant Templates in Aerosols", Advanced Materials, vol. 18, 2002, pp. 1301-1304.
Rens, W. et al. "A Novel Nozzel for More Efficient Sperm Orientation to Improve Sorting Efficiency of X and Y Chromosome-Bearing Sperm", Cytometry, vol. 33, 1998, pp. 476-481.
Ricks, D. et al. "A numerically stable global matrix method for cylindrically layered shells excited by ring forces", J Acoust Soc Am, vol. 95, 1994, pp. 3339-3349.
Rouleau, F. et al. "Electromagnetic scattering by compact clusters of spheres", Astron. Astrophys, vol. 310, 1996, pp. 696-698.
Rudnick, J. et al. "Oscillational instabilities in single-mode acoustic levitators", J Acoust Soc Am, vol. 87, 1990, pp. 81-92.
Saito, M. et al. "Microorganism manipulation and microparticle arrangement by the use of ultrasonic standing waves", SPIE, vol. 4590, 2001, pp. 26-37.
Saito, M. et al. "Ultrasonic manipulation of locomotive microorganisms and evaluation of their activity", J App Physics, vol. 92, 2002, pp. 7581-7586.
Saito, M. et al. "Ultrasonic trapping of paramecia and estimation of their locomotive force", Appl Phys Lett, vol. 71, 1997, pp. 1909-1911.
Saito, M. et al. "Ultrasonic waves for fabricating lattice structure in composite materials", SPIE, vol. 3786, 1999, pp. 179-190.
Samiotaki, M. et al. "Seven-Color Time-Resolved Fluoresence Hybridization Analysis of Human Papilloma Virus Types", Analytical Biochemistry, vol. 253, 1997, pp. 156-161.
Sato, M. et al. "Quantum mechanical representation of acoustic streaming and acoustic radiation pressure", Physical Review E, vol. 64, 2001, pp. 026311-1-026311-5.
Schmid, M. et al. "A computer-controlled system for the measurement of complete admittance spectra of piezoelectric resonators", Meas Sci Technol, vol. 1, 1990, pp. 970-975.
Schoell, W. et al. "Separation of Sperm and Vaginal Cells with Flow Cytometry for DNA Typing After Sexual Assault", Obstetrics and Gynecology, vol. 94, 1999, pp. 623-627.
Semianov, K. et al. "Measurement of Mammalian Erythrocyte Indices from Light Scattering with Scanning Flow Cytometer", Proc SPIE, vol. 5141, 2003, pp. 106-113.
Sethu, P. et al. "Continuous Flow Microfluidic Device for Rapid Erythrocyte Lysis", Anal Chem, vol. 76, 2004, pp. 6247-6253.
Shapiro, H. "Practical Flow Cytometry", Third Edition, Wiley-Liss N.Y. vol. 223, 1995, 24 pgs.
Shapiro, H. "Chapter 7: Parameters and Probes", Practical Flow Cytometry, 4th Edition, Jan. 1, 2003, 138 pgs.

(56) References Cited

OTHER PUBLICATIONS

Shapiro, H. et al. "Practical Flow Cytometry", Hoboken, NJ, John Wiley & Sons, Inc, 2005, 9-13.
Shvalov, A. et al. "Individual *Escherichia coli* Cells Studied from Light Scattering with the Scanning Flow Cytometer", Cytometry, vol. 41, 2000, pp. 41-45.
Shvalov, A. et al. "Light-scattering properties of individual erythrocytes", Applied Optics, vol. 38, 1999, pp. 230-235.
Simpson, H. et al. "Ultrasonic four-wave mixing mediated by an aqueous suspension of microspheres: Theoretical steady-state properties", J Acoust Soc Am, vol. 98, No. 3, 1995, pp. 1731-1741.
Skudrzyk, E. "Die Grundlagen der Akustic", Springer Verlag Wien, 1954, 202-205, pp. 807-825.
Slomkowski, S. et al. "New Types of Microspheres and Microsphere-related Materials for Medical Diagnostics", Polymers for Advanced Technologies, vol. 13, 2002, pp. 906-918.
Sobanski, M. et al. "Sub-micron particle manipulation in an ultrasonic standing wave: Applications in detection of clinically important biomolecules", Bioseparation, vol. 9, 2001, pp. 351-357.
Springer Reference, "Acoustic Contrast Factor Abstract", Referenced from Gorkov, L.P. (1962), 2014, 1 pg.
Steinkamp, J. et al. "Enhanced Immunofluorescence Measurement Resolution of Surface ANtigens on Highly Autofluorescent, Glutaraldehyde-Fixed Cells Analyzed by Phase-Sensitive Flow Cytometry", Cytometry, vol. 37, 1999, pp. 275-283.
Steinkamp, J. et al. "Dual-Laser, Differential Fluorescence Correction Method for Reducing Cellular Background Autofluorescence", Cytometry, vol. 7, Alan R. Liss, Inc. 1986, pp. 566-574.
Steinkamp, J. "A Differential Amplifier Circuit for Reducing Noise in Axial Light Loss Measurements", Cytometry, vol. 4, Alan R. Liss. Inc. 1983, pp. 83-87.
Stewart, C. et al. "Resolving Leukocytes Using Axial Light Loss", Cytometry, vol. 10, Issue 4, 1989, pp. 426-432.
Stoffel, C. et al. "Data Analysis for a Dual-Channel Virus Counter", Analytical Chemistry, vol. 7, Dept of Chemistry & Biochemistry, Univ of Colorado, 2005.
Stoffel, C. et al. "Design and Characterization of a Compact Dual Chanel Virus Counter", Cytometry, Part A, vol. 65A, Dept of Chemistry and Biochemistry, Univ of Colorado, 2005.
Stovel, R. et al. "A Means for Orienting Flat Cells in Flow Systems", Biophys J, vol. 23, 1978, pp. 1-5.
Takeuchi, M. et al. "Ultrasonic Micromanipulation of Small Particles in Liquid", Jpn J Appl Phys, vol. 33, 1994, pp. 3045-3047.
Takeuchi, M. et al. "Ultrasonic Micromanipulator Using Visual Feedback", Jpn J Appl Phys, vol. 35, 1996, pp. 3244-3247.
Thiessen, D. et al. "Principles of some Acoustical, Electrical, and Optical Manipulation Methods with Applications to Drops, Bubbles, and Capillary Bridges", ASME Fluids Eng Div Publ. FED, 1998.
Thiessen, D. et al. "Some Responses of Small Diffusion Flames to Ultrasonic Radiation", NASA, 2003, pp. 321-324.
Tolt, T. et al. "Separation devices based on forced coincidence response of fluid-filled pipes", J Acoust Soc Am, vol. 91, 1992, pp. 3152-3156.
Tolt, T. et al. "Separation of Dispersed Phases from Liquids in Acoustically Driven Chambers", Chem Eng Science, vol. 48, 1993, pp. 527-540.
Townsend, R. et al. "Modelling of particle paths passing through an ultrasonic standing wave", Ultrasonics, vol. 42, 2004, pp. 319-324.
Trinh, E. et al. "Compact acoustic levitation device for studies in fluid dynamics and material science in the laboratory and microgravity", Rev Sci Instrum, vol. 56, 1985, pp. 2059-2065.
Trinh, E. et al. "Experimental study of streaming flows associated with ultrasonic leviators", Phys Fluids, vol. 6, 1994, pp. 3567-3579.
Tuckermann, R. et al. "Trapping of heavy gases in stationary ultrasonic fields", Chem Phys Ltrs, vol. 363, 2002, pp. 349-354.
Tung, Y. et al. "PDMS-based opto-fluidic micro flow cytometer with two-color, multi-angle fluorescence detection capability using PIN photodiodes", Sensors and Actuators, vol. 98, 2004, pp. 356-367.
Tyson, D. et al. "Ruthenium (II) complex with a notably long excited state lifetime", The Royal Society of Chemistry, 2000, pp. 2355-2356.
Vainshtein, P. et al. "On the Drift of Aerosol Particles in Sonic Fields", J Aerosol Sci, vol. 23, 1992, pp. 631-637.
Vainshtein, P. et al. "The effect of centreline particle concentration in a wave tube", J Fluid Mech, vol. 306, 1996, pp. 31-42.
Van Hee, P. et al. "Strategy for Selection of Methods for Separation of Bioparticles From Particle Mixtures", Biotech Bioeng, vol. 94, 2006, pp. 689-709.
Verpoorte, E. "Beads and chips: new recipes for analysis—Elisabeth Verpoorte reviews particle handling in microchannels", Lab Chip, vol. 3, 2003, pp. 60N-68N.
Visuri, S. et al. "Microfluidic Tools for Biological Sample Preparation", 2nd Annual International IEEE-EMBS SPecial Topic Conference of Microtech in Med & Bio, 2002, pp. 556-559.
Wang, Z. et al. "Retention and Viability Characteristics of Mammalian Cells in an Acoustically Driven Polymer Mesh", Biotechnol Prog, vol. 20, 2004, pp. 384-387.
Ward, M. et al. "Fundamentals of Acoustic Cytometry", Current Protocols in Cytometry, Supplement 49, 2009, pp. 1.22.1-1.22.12.
Ward, M. et al. "Manipulation of Immunomagnetic Targets in Microfluidic Channel Flow", PhD Dissertation, Arizona State University, 2005, pp. 1-205.
Weiser, M. et al. "Interparticle Forces on Red Cells in a Standing Wave Field", Acustica, vol. 56, 1984, pp. 114-119.
Weiser, M. et al. "Extension of acoustic levitation to include the study of micron-size particles in a more compressible host liquid", J Acoust Soc Am, vol. 71, 1982, pp. 1261-1268.
Whitworth, G. et al. "Transport and harvesting of suspended particles using modulated ultrasound", Ultrasonics, vol. 29, 1991, pp. 439-444.
Whitworth, G. et al. "Particle column formation in a stationary ultrasonic field", J Acoust Soc Am, vol. 91, 1992, pp. 79-85.
Wu, Y. et al. "Diazo Coupling Method for Covalent Attachment of Proteins to Solid Substrates", Bioconjugate Chem, vol. 17, 2006, pp. 359-365.
Yagi, Y. et al. "Flow cytometry to evaluate theileria sergenti parasitemia using the fluorescent nucleic acid stain, SYT016", Cytometry, 41, 2000, pp. 223-225.
Yamakoshi, Y. et al. "Micro particle trapping by opposite phases ultrasonic travelling waves", Ultrasonics, vol. 36, 1998, pp. 873-787.
Yasuda, K. et al. "Concentration and Fractionation of Small Particles in Liquid by Ultrasound", Jpn J Appl Phys, vol. 34, 1995, pp. 2715-2720.
Yasuda, K. et al. "Dexoyribonucleic acid concentration using acoustic radiation force", J Acoust Soc Am, vol. 99, 1996, pp. 1248-1251.
Yasuda, K. et al. "Non-destructive, non-contact handling method for biomaterials in micro-chamber by ultrasound", Sensors and Actuators, vol. 64(1-3), 2000, pp. 128-135.
Yasuda, K. et al. "Particle separation using acoustic radiation force and electrostatic force", J Acoust Soc Am, vol. 99, 1996, pp. 1965-1970.
Yasuda, K. et al. "Blood Concentration by Superposition of Higher Harmonics of Ultrasound", Jpn. J. Appl. Phys, vol. 36, 1997, pp. 3130-3135.
Yasuda, K. et al. "Using acoustic radiation force as a concentration method for erythrocytes", J. Acoust. Soc. Am, vol. 102, 1997, pp. 642-645.
Ye, C. et al. "Preparation of three terbium complexes with paminobenzoic acid and investigation of crystal structure influence on luminescence property", Journal of Solid State Chemistry, vol. 177, 2004, pp. 3735-3742.
Yosioka, K. et al. "Acoustic Radiation Pressure on a Compressible SPhere", Acustica, vol. 5, 1955, pp. 167-173.
Yuan, J. et al. "Lanthanide-based luminescence probes and time-resolved luminescence bioassays", Trends in Analytical Chemistry, vol. 25, No. 5, 2006, pp. 490-500.
Yurkin, M. et al. "Experimental and theoretical sutdy of light scattering by individual mature red blood cells by use of scanning flow cytometry and a discrete dipole approximation", Applied Optics, vol. 44, 2005, pp. 5249-5256.

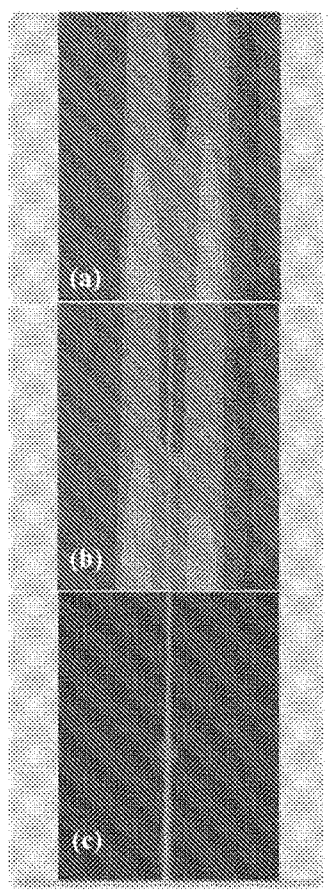
FIG. 5A
FIG. 5B
FIG. 5C
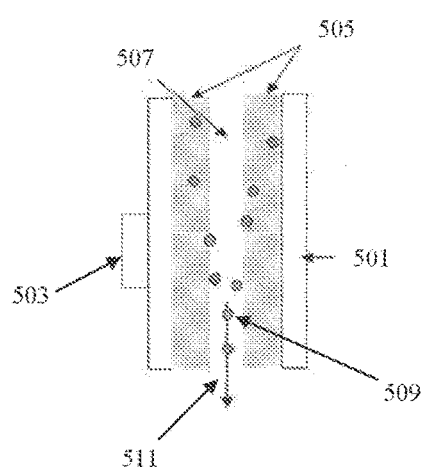
FIG. 5D

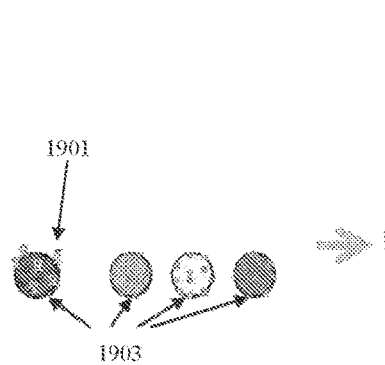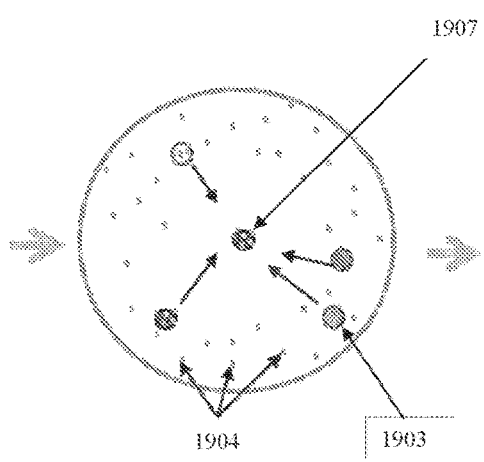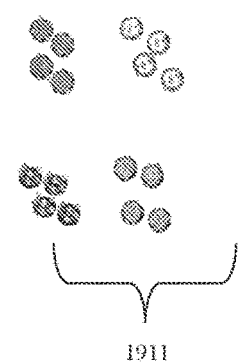
FIG. 19A
FIG. 19B
FIG. 19C

PARTICLE ANALYZING SYSTEMS AND METHODS USING ACOUSTIC RADIATION PRESSURE

CROSS-REFERENCE TO RELATED APPLICATIONS

This application is a continuation of U.S. application Ser. No. 12/239,453 filed Sep. 26, 2008, which is a continuation-in-part of PCT application no. PCT/US2008/059181 filed Apr. 2, 2008, and claims priority to U.S. application No. 61/026,082 filed Feb. 4, 2008, and to U.S. application No. 60/909,704 filed Apr. 2, 2007, which disclosures are herein incorporated by reference in their entirety.

This application is also related to the following applications filed on even date herewith: "Medium Switching Systems and Methods Using Acoustic Radiation Pressure," U.S. Pat. No. 8,227,257; "Particle Switching Systems and Methods Using Acoustic Radiation Pressure" U.S. patent application Ser. No. 12/239,410; "Particle Imaging Systems and Methods Using Acoustic Radiation Pressure," U.S. Pat. No. 8,134,705; and "Particle Fusing Systems and Methods Using Acoustic Radiation Pressure," U.S. patent application Ser. No. 12/239,483; "Kits for Systems and Methods Using Acoustic Radiation Pressure," U.S. patent application Ser. No. 12/239,501; "Particle Quantifying Systems and Methods Using Acoustic Radiation Pressure," U.S. Pat. No. 8,309,408 and the specifications and claims thereof are incorporated herein by reference.

BACKGROUND OF THE INVENTION

Field of the Invention (Technical Field)

Embodiments of the present invention relate to systems using acoustic radiation pressure.

Background

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Flow cytometry is a powerful tool used for analysis of particles and cells in a myriad of applications primarily in bioscience research and medicine. The analytical strength of the technique lies in its ability to parade single particles (including bioparticles such as cells, bacteria and viruses) through the focused spot of light sources, typically a laser or lasers, in rapid succession, at rates up to thousands of particles per second. The high photon flux at this focal spot produces scatter of light by a particle and or emission of light from the particle or labels attached to the particle that can be collected and analyzed. This gives the user a wealth of information about individual particles that can be quickly parleyed into statistical information about populations of particles or cells.

In traditional flow cytometry, particles are flowed through the focused interrogation point where a laser directs a laser beam to a focused point that includes the core diameter within the channel. The sample fluid containing particles is focused to a very small core diameter of around 10-50 microns by flowing sheath fluid around the sample stream at a very high volumetric rate on the order of 100-1000 times the volumetric rate of the sample. This results in very fast linear velocities for the focused particles on the order of meters per second. This in turn means that each particle spends a very limited time in the excitation spot, often only 1-10 microseconds. Further, once the particle passes the interrogation point the particle cannot be redirected to the interrogation point again because the linear flow velocity cannot be reversed. Further, a particle cannot be held at the interrogation point for a user defined period of time for further interrogation because focusing is lost without the flow of the hydrodynamic sheath fluid. Because of the very high photon flux at the excitation point, flow cytometry is still a very sensitive technique, but this fast transit time limits the sensitivity and resolution that can be achieved. Often, greater laser power is used to increase the photon flux in an effort to extract more signal but this approach is limiting in that too much light can often photobleach (or excite to non-radiative states) the fluorophores being used to generate the signal and can increase background Rayleigh scatter, Raman scatter and fluorescence.

Acoustic cytometers, using relatively large dimension flow channels, concentrate particles from the entire volume of the channel to a small acoustic trap in the center of the channel and can therefore offer both controllable flow and high particle analysis rates without resorting to highly concentrated samples.

BRIEF SUMMARY OF THE INVENTION

An embodiment of the present invention comprises a method for acoustically reorienting a fluid in a channel. This method preferably includes introducing into a channel a first fluid wherein the first fluid has a first acoustic contrast relative to a second fluid, introducing into the channel the second fluid wherein the second fluid has a second acoustic contrast that is different from the first acoustic contrast, applying acoustic radiation pressure to the channel, and acoustically reorienting the second fluid based upon the acoustic contrast of the second fluid. The method can acoustically reorient the first fluid and the second fluid relative to particles. The first fluid and/or the second fluid preferably move in laminar flow streams. The method can also further comprise assaying the particles or fluids to produce an assay. An assay is preferably produced by the method wherein the second fluid is a biological fluid selected from the group consisting of cell culture medium, serum, blood, bone marrow, semen, vaginal fluid, urine, spinal fluid, saliva, sputum, bile, peritoneal fluid, amniotic fluid, and aspirate from hollow organs, cysts and tissue. One of the fluids of the method can comprise a reagent. The reagent can be selected from a) an antibody or aptamer specific for a particle antigen; b) a ligand specific for a particle receptor; c) an enzyme specific for a particle substrate; d) a nucleic acid stain specific for particle nucleic acid; e) an antigen specific for a particle antibody, f) an analyte specific for a particle target; g) a secondary reagent specific for one or more of a-f; and h) any combination thereof. The method can optionally include passing a particle through a zone for collection of luminescence and collecting chemi, bio or electro luminescence from the particle. The particles can be focused with a radial acoustic field. The collecting of luminescence can occur between excitation pulses from a light source.

Another embodiment of the present invention comprises a method for acoustically manipulating a particle using radial acoustic focusing. This embodiment preferably comprises introducing into a channel a first fluid having a first acoustic contrast with a population of particles suspended therein, introducing into the channel a second fluid having a second acoustic contrast that is greater than or equal to the acoustic contrast of the first fluid, applying a radial acoustic radiation pressure to the channel, and acoustically focusing at least a portion of the population of particles from the first fluid to the second fluid. The first fluid and/or the second fluid preferably move in laminar flow streams. A portion of the population of particles can be acoustically focused relative to the first acoustic contrast and the second acoustic contrast. In this embodiment a subset of particles may be more than one size and a first particle size can be acoustically focused more quickly into the second fluid than a subset of particles having a second particle size. Particles useful as standards in flow cytometry having been acoustically separated by size and having an improved coefficient of variation after acoustic separation as compared to the starting population of particles wherein the particles are produced by the method of this embodiment. The first fluid of this embodiment can comprise a reagent that specifically binds at least a subset of the portion of the population of particles. The method can also further comprise non-dilutive sorting of the portion of the population of particles in the second fluid. The first and/or second fluid of this embodiment can comprise a reagent that reacts with at least some of the particles from the portion of the population of particles in the second fluid. The reagent can be selected from a) antibodies or aptamers specific for particle antigens; b) ligands specific for particle receptors; c) enzyme specific for particle substrate; d) stains specific for particle nucleic acid; e) an antigen specific for a particle antibody, f) an analyte specific for a particle target; g) a secondary reagent specific for one or more of a-f; and h) any combination thereof.

The method described above may also have the second fluid located at the center of the channel. In addition, the particles can be in the first fluid or the second fluid to a particle analyzer, e.g. a flow cytometer that is in line with the channel. Acoustically focusing in this embodiment can comprise acoustically focusing a subset of the population of particles with greater contrast to the second stream for collection and excluding a subset of the population of particles with a lesser contrast from collection. The population of particles in this embodiment may comprise an array of beads having a target specific for a pre-bound fluorescent analyte of interest and wherein the second fluid is suspected of containing non fluorescent analyte that is capable of binding specifically to its target on a bead from the array of bead and further comprising displacing the pre-bound fluorescent analyte with a non-fluorescent analyte when the bead is acoustically focused in the second fluid and analyzing the array of beads for fluorescence.

The method of the embodiment above can further comprise acoustically focusing the cell into a reagent loaded second fluid and providing to the cell an electric field that permeates the cell membrane to permit the reagent to cross into the permeated cell.

The method of the embodiment above may also comprise a reagent that binds to at least a portion of the subset of the population of particles to form a particle-reagent complex having an acoustic contrast different than the acoustic contrast of the portion of the population of particles not complexed with reagent. The particle-reagent complex is acoustically focused away from at least a portion of the population of particles not complexed with reagent.

The population of particles can be cultured cells, the first fluid can be cell growth medium in which the cells are grown and the second fluid can be new cell growth medium.

The method can further comprise capturing a particle of interest from the population of particles with a negative contrast particle and forcing the particle of interest and the negative contrast particle toward a wall of the channel away from a center of the channel.

The method can alternatively comprise producing an acoustic node outside the channel wherein the reorienting of the second fluid with the at least a portion of the particles therein is to the top surface of the channel near the acoustic node.

The method can additionally comprise introducing a calcium sensitive reagent into a cell, moving the cell through a channel, acoustically focusing the cell within the channel, exposing the cell to a reagent that may or may not induce a cellular calcium response, passing the cell through an interrogation site, and collecting a signal to determine calcium concentration in the cell. In this method, the cell is preferably acoustically washed and/or diluted prior to collection. This method can further comprise adjusting a flow rate to achieve a desired time of collection after the exposure to the reagent that may or may not induce a calcium response.

Yet another embodiment of the present invention comprises a method for imaging acoustically manipulated particles in an acoustic flow cytometer. This method preferably comprises introducing a fluid containing a population of particles therein to a flow cell, applying acoustic radiation pressure to the flow cell, acoustically focusing the population of particles within the flow cell to concentrate the population of particles, aligning some of the concentrated population of particles in the flow cell, interrogating some of the aligned population of particles at an interrogation site to obtain an optical signal from some of the population of particles to yield population statistical data, and imaging at least one of the population of particles to produce a high content image representative of the population of particles. The method can further comprise the step of correlating the population statistical data with the high content image to produce improved data content. The transit time of the population of particles may also be slowed during the interrogating step.

One embodiment of the present invention is a method for optimizing particle throughput in a particle analyzer for a user defined transit time with a given concentration of particles. This method preferably comprises the steps of determining optimal concentration of particles to achieve a user defined coincidence rate, adjusting sample concentration to achieve the coincidence rate, acoustically focusing particles in the particle analyzer, adjusting flow rate to achieve desired user defined transit time of the particles, and analyzing the particles at an interrogation point. The particle analyzer can be a flow cytometer or cell impedance analyzer.

Another embodiment of the present invention comprises a method of fusing an antibody producing cell with an immortal cell to produce a hybridoma cell. This embodiment preferably comprises acoustically focusing in a first channel having a first acoustic field an antibody producing cell capable of fusing with an immortal cell, acoustically focusing the immortal cell in a second channel having a second acoustic field, flowing the acoustically focused antibody producing cell and the acoustically focused immortal cell to a third channel having a third acoustic field that acoustically focuses the antibody cell and the immortal cell into close enough proximity to permit the antibody cell and the immortal cell to fuse, and fusing the antibody cell and the immortal cell together by a chemical or electrical means to form a hybridoma cell. A hybridoma cell line is preferably created by the method.

Yet another embodiment of the present invention comprises a method of analyzing particles with a particle analyzer. This method preferably comprises the steps of acoustically focusing particles to the approximate center of a channel having an electrolytic fluid therein, flowing the particles through a pore of the channel separating two electrodes between through which an electric current flows, and detecting the signal wherein the particles displace their own volume of electrolyte momentarily increasing the impedance of the pore to produce the signal. The electrolytic fluid of this embodiment is preferably of an engineered conductivity. In addition, a fluid for use in the method preferably has an engineered conductivity. The particles in this method are preferably blood cells.

A further embodiment of the present invention comprises a method of acoustically focusing particles in a plane. This embodiment preferably comprises transiting a fluid containing particles therein through a channel at a flow rate, adjusting the flow rate for a desired transit time through an excitation source, optically exciting the particles with the excitation source, detecting an optical signal from the particles, and analyzing the optical signal. This embodiment can further comprise disposing a substantially acoustically transparent gas-contacting membrane at a top surface of the flow channel wherein a pressure node is located outside of the channel at a gas interface.

Another embodiment of the present invention comprises a kit for acoustically focusing at least one particle. This kit preferably includes a container means having a first fluid, the container means having a population of particles therein wherein the population of particles are engineered for an acoustic radiation pressure apparatus, wherein the particles having an acoustic contrast greater than the first fluid and the first fluid has an acoustic contrast that is greater than water and wherein the first fluid comprises one or more engineered population of particles. In this embodiment, the first fluid preferably comprises a heavy salt. The heavy salt is selected from the group consisting of potassium bromide and cesium chloride. Alternatively, the first fluid can comprise an iodinated compound. The iodinated compound is selected from the group consisting of metrizamide, Nycodenz®, diatrizoate, and iodixanol. The first fluid can also comprise nanoparticles or sucrose, polysucrose, polydextran, and glycerol. The population of particles is preferably a material selected from polystyrene, acrylic, iron oxides, silica or any combination thereof. The acoustic contrast of the population of particles is preferably greater than a target acoustic contrast. The population of particles can comprise a first subset of the population and second subset of the population wherein the first subset of the population is different than the second subset of the population. The first subset of the population preferably has a probe specific for a first analyte and the second subset of the population preferably has a probe specific for a second analyte. The first analyte of this embodiment of preferably different from the second analyte. The first population of particles can labeled with a first signaling molecule having a first lifetime and the second population of particles can labeled with a second signaling molecule having a second lifetime.

Still another embodiment of the present invention comprises a kit for acoustic focusing. This kit preferably includes a container means having a first fluid, and a container means having a reagent for labeling a particle, wherein the particle has an acoustic contrast greater than the first fluid, the first fluid has an acoustic contrast that is greater than water and wherein the first fluid comprises one or more engineered particles engineered specifically for an acoustic radiation pressure apparatus. The particle of this kit preferably comprises a material selected from polystyrene, acrylic, iron oxides, silica or any combination thereof. The particle acoustic contrast is preferably greater than the reagent acoustic contrast. Alternatively, the particle can be a white blood cell, and the reagent is an antibody or fab fragment that specifically binds to a surface receptor on the white blood cell. The first fluid comprises heavy salt. The heavy salt is selected from the group consisting of potassium bromide and cesium chloride. The first fluid can alternatively comprise an iodinated compound. The iodinated compound is selected from the group consisting of metrizamide, Nycodenz®, diatrizoate, and iodixanol. The first fluid can alternatively comprise nanoparticles or one or more of the following sucrose, polysucrose, polydextran, and glycerol.

One embodiment of the present invention is a kit for reagents for use in an acoustic apparatus with two streams. This kit preferably includes a first fluid for use in a first fluid stream of the acoustic apparatus, a second fluid and a particle wherein the second fluid is used in a second stream, and instructions for acoustically focusing the particle in an acoustic flow cytometer. The first fluid preferably has an acoustic contrast that is less than the acoustic contrast of the second fluid and less than the acoustic contrast of the particles in the first fluid. The second fluid preferably has an acoustic contrast that is greater than the acoustic contrast of the first fluid and less than the acoustic contrast of the particles. The particle preferably binds a target. The particles preferably comprise a material selected from polystyrene, acrylic, iron oxides, silica or any combination thereof. The acoustic contrast of the particle is preferably greater than target acoustic contrast. The first fluid in this kit can be a wash fluid or a lysis fluid.

Another kit of the present invention is a kit for reagents for use in an acoustic apparatus with two streams. This kit preferably comprises a first fluid, a second fluid and a reagent for labeling a particle. The first fluid is preferably used in a first stream, and the second fluid is preferably used in a second stream. The first fluid preferably has an acoustic contrast that is less than the second fluid. The second fluid has an acoustic contrast that is greater than the first fluid. The particles in this kit can be a white blood cell. The first fluid can be a wash fluid or a lysis fluid.

Another embodiment of the present invention comprises a method for analyzing a particle in a long transit time flow cytometer. This method preferably comprises introducing a particle having a signaling molecule associated therewith to a particle analyzer having a laser interrogation light source, interrogating the particle having the signaling molecule associated therewith repeatedly with the laser interrogation light source having interrogation light source bursts of about 0.1 ns-100 ns wherein the burst occurs at a rate of about 0.01 MHz-2 Mhz to saturate or nearly saturate excitation of the signaling molecule, and collecting an optical signal from the signaling molecule and analyzing data to obtain information about the particle wherein the rest times are at least 25% of the lifetime for a non-radiative decay rate.

Yet another embodiment of the present invention comprises a method of measuring multiple analytes in a sample using an acoustic flow cytometer. This embodiment preferably comprises introducing a sample suspected of containing one or more targets of interest into the acoustic flow cytometer, measuring the presence of the one or more targets of interest with a first probe and a second probe wherein the first probe has a signaling molecule with a long optical lifetime emission spectra and the second probe has a signaling molecule with a shorter optical lifetime emission spectra relative to the first probe wherein the first probe and the second probe have a different specificity and wherein the signaling molecule with the long optical lifetime emission spectra and the signaling molecule with the shorter optical lifetime emission spectra have overlapping emission spectra and wherein the one or more targets of interest are measured in an acoustic flow cytometer, exciting the signaling molecule with a long optical lifetime and the signaling molecule with the shorter optical lifetime with a pulsed light source, measuring the signal of both the long and short lifetime signaling molecules and the signal of the long lifetime probe after the short lifetime probe signal has decayed, and calculating the contribution of each signaling molecule based on the combined signal of both molecules, the signal of the long lifetime molecule after the signal from the short lifetime molecule has decayed and the known lifetime curves of the signaling molecule.

The embodiment above can further comprise pooling an array of particle subsets, each subset having a predetermined amount of at least one light absorbing dye and a reactant specific for the analyte, exposing the array of particles to the sample containing the analyte, forming an analyte-particle complex, passing the analyte-particle complex through an interrogation site, determining the identity of each particle based on its axial light loss absorbance measurement, and determining the presence, quantity and identity of the analyte bound to the particle based on data specific to the formation of the analyte-particle complex. This method can also optionally comprise reacting at least one additional reagent to the sample prior to passage through the interrogation site and indicating the presence of the particle-analyte complex. The interrogation site of this embodiment preferably comprises at least one light source. The light source is preferably pulsed or modulated. The particle array preferably has an additional fluorescent label that is used as a reference for quantification of the analyte.

One embodiment of the present invention comprises an acoustic flow cytometer capable of measuring axial light loss. This acoustic flow cytometer preferably comprises a channel having an inlet for accepting a fluid sample stream of the analytes, an acoustic signal producing transducer coupled to the channel wherein the acoustic signal producing transducer produces an acoustic signal to the channel to induce within the channel acoustic radiation pressure capable of inducing an outer boundary surface displacement to concentrate the analytes within the fluid sample stream, optical equipment for analyzing the analytes wherein the optical equipment comprises a light source or light sources with one or more wavelengths for analyzing the analytes when the analytes pass through the one or more wavelengths, and a linear array detector(s) to detect absorbance from the analytes to determine characteristics of the analytes.

Another embodiment of the present invention comprises a method of fusing particle populations. This method preferably comprises the steps of acoustically focusing in a first flow channel with a first acoustic field a first particle population capable of fusing with a second particle population, acoustically focusing the second particle population in a second flow channel with a second acoustic field, flowing the acoustically focused first particle population and second particle population to a third flow channel with a third acoustic field that acoustically focuses the first particle population and the second particle population into close enough proximity to permit the particles to fuse, and fusing the first particle population and the second particle population by a physical, chemical or electrical means. This method preferably produces a fused particle.

Yet another embodiment of the present invention comprises a method for separating magnetic particles or magnetically stained cells. This method preferably comprises moving particles or cells with small enough magnetic susceptibility to avoid magnetic aggregation in the magnetic field of separation into a separation channel where they are drawn to a surface(s) in a region of gradient magnetic fields, magnetically moving the particles to a surface(s) where they continue to move in the direction of flow due to hydrodynamic forces, magnetically moving the particles through at least one additional laminar stream of fluid before reaching the surface(s), and moving the particles along the surface(s) in the magnetic field to a location where they can be collected. The surface of this method is preferably a magnetic wire or magnetically susceptible feature spanning the height of the flow channel. A method for analyzing magnetic particles or magnetically stained cells in a particle analyzer or the like preferably comprises flowing particles or cells with small enough magnetic susceptibility to avoid magnetic aggregation in a magnetic focusing field, into a channel where they are exposed to gradient fields and moving particles along the surface in the magnetic field such that they are focused into flow lines that can be analyzed downstream using optical detectors. The surface(s) of this embodiment are preferably magnetic or magnetically susceptible tapered features(s) that terminate prior to the analysis point. The particles are preferably magnetically moved through at least one additional laminar stream of fluid before reaching said surface.

One embodiment of the present invention is a method for fractionating particles. This embodiment preferably includes providing a fluid having particles therein, applying acoustic radiation pressure to the fluid, focusing the particles within the fluid into a single file line, moving the particles in a flow rate, applying acoustic radiation pressure to the fluid for a second time, focusing the particles based on size and acoustic contrast, producing at least two fluid fractions of the particles, and collecting at least one of the fractions. The method may further include adjusting the flow rate and/or the first or second acoustic radiation pressure such that particles with different physical properties are diverted to different fluid fractions. The particles of this embodiment are preferably focused into the single file line using an acoustic standing wave field. The acoustic standing wave field is preferably generated using a radial focusing device. The fluid of this embodiment is preferably drawn away from the sample prior to acoustic fractionation in order to steer the particles to a different part of the acoustic fractionating field. Particles in flow cytometry having been acoustically separated by size using this method are useful and have an improved coefficient of variation after acoustic separation as compared to the starting population. The coefficient of variation can be improved by >40% or even >80%.

A further embodiment of the present invention comprises a method for quantifying the amount of analyte bound to a particle in an acoustic particle analyzer. This method preferably comprises binding a particle having a known amount of calibration dye and a specificity for an analyte to the analyte having a lifetime related signal to form an analyte-particle complex, passing the analyte-particle complex through an interrogation light source, measuring the signal related to the binding event in an interrogation site, measuring an overlapping signal from the calibration dye, and calculating the amount of analyte present by comparing the analyte related signal to the signal from the calibration dye. The interrogation light source of this embodiment if preferably pulsed. The analyte having the short lifetime related signal comprises a ligand with a label associated therewith wherein the ligand binds with specificity to the analyte such that the particle and analyte and labeled ligand form a complex. The calibration dye preferably has a long lifetime and the lifetime related signal of the analyte is a short lifetime signal. Or the calibration dye can have a short lifetime and the lifetime related signal of the analyte is a long lifetime signal.

Still another embodiment of the present invention is a method for identifying and quantifying multiple analytes using coded beads from a pooled population of beads and fluorescence lifetime in a particle analyzer. This method preferably includes pooling an array of particle subsets, each subset having a predetermined amount of at least one short lifetime fluorescent label and at least one long lifetime fluorescent label and a reactant specific for an analyte, exposing the array of particles to a sample such that the analytes within the sample form an analyte-particle complex, passing the array of particles through an interrogation light source, determining the identity of each particle based on its lifetime curve, and determining the presence, quantity and identity of the analyte bound to the particle based on data specific to the formation of the analyte-particle complex. This method can further comprise reacting at least one additional reagent to the sample prior to passing the array of particles through the interrogation light source and indicating the presence of the particle-analyte complex. This method can optionally comprise measuring the lifetime curve of each particle using a single optical detector. The particle analyzer of this embodiment is preferably an acoustic cytometer. The particle array preferably comprises an additional fluorescent label that is used as a reference quantification of the analyte.

Another embodiment of the present invention includes a method for increasing the dynamic range of measurements in an acoustic particle analyzer. This method comprises passing particles capable of scattering or emitting an optical signal through an interrogation site, interrogating each particle with an intensity modulated excitation light source for producing the optical signal comprising scatter and emissions from the particles, collecting the optical signal, quantifying the strongest scatter and emissions signals from a low excitation level produced by the intensity modulated excitation light source, and quantifying the weakest scatter and emissions signals from a high excitation level produced by the intensity modulated excitation light source. The particle analyzer of this method is preferably an acoustic cytometer. The modulated excitation light source is preferably pulsed.

Yet another embodiment of the present invention is a method for increasing dynamic range measurement of a fluorescent bead having at least two fluorescent color labels in known quantities in a particle analyzer. This embodiment preferably includes the steps of passing a particle through an interrogation site, simultaneously measuring a first signal of a first detector sensitive to one wavelength band of light and a second signal of a second detector sensitive to a different wavelength band of light, and determining the ratio of each label to the other label based on the ratio signal rise time in the first detector relative to the second detector. The particle analyzer of this embodiment is preferably an acoustic cytometer.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 5A-5C illustrate the separation of micron sized polystyrene fluorescent orange/red particles from a background of nanometer sized green particles in a homogeneous fluid according to one embodiment of the present invention. FIG. 5D illustrates a clean core stream introduced alongside a coaxial stream containing fluorescent background according to an embodiment of the present invention.

FIGS. 19A-19C illustrate a diagram of an aptamer selection from a library, multiplexed beads or cells with target molecules incubated with aptamer library according to one embodiment of the present invention.

DETAILED DESCRIPTION OF THE INVENTION

Figure 1:
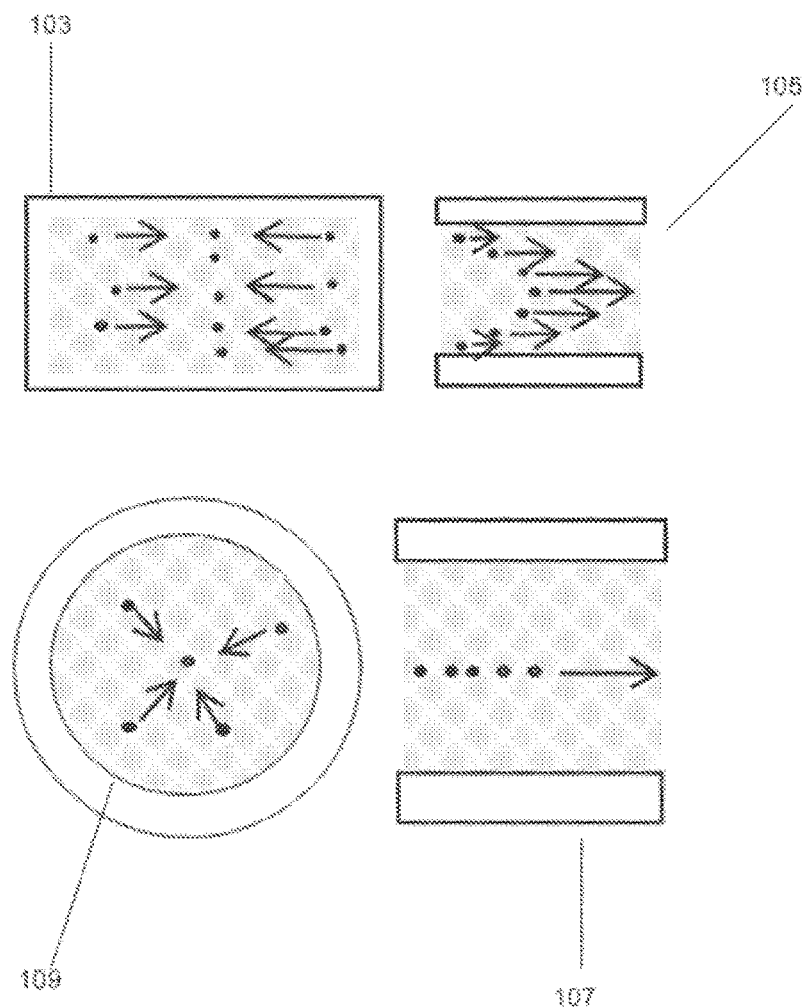
FIG. 1 is an illustration of field focused particles according to one embodiment of the present invention.

The present invention relates to systems using acoustic radiation pressure. Acoustic radiation pressure can be used to concentrate and align particles in fluids. This ability has many applications in the fields of particle analysis and sample preparation. As described herein acoustic radiation pressure is applied primarily to flow cytometry, reagents for use in flow cytometry and sample preparation for flow cytometry. Acoustic cytometers, using relatively large dimension flow channels, concentrate particles from the entire volume of the channel to a small acoustic trap in the center of the channel and can therefore offer both controllable flow and high particle analysis rates without requiring highly concentrated samples. Many of the sample preparation methods have wider application and a few of these embodiments are disclosed.

As used herein "acoustic contrast" means the relative difference in material properties of two objects with regard to the ability to manipulate their positions with acoustic radiation pressure. The acoustic force due to acoustic radiation pressure on a compressible, spherical particle of volume V in an arbitrary acoustic field (neglecting viscosity and thermal conductivity) can be written in terms of an acoustic radiation pressure force potential U:

$$U = \frac{4}{3}\pi a^3 \left[ \left(\beta_0 \frac{\langle p^2 \rangle}{2}\right) f_1 - \frac{3}{2}\left(\frac{\rho_0 \langle v^2 \rangle}{2}\right) f_2 \right]. \quad (1)$$

Here, a is the particle radius, $\beta_o$ is the compressibility of the surrounding fluid, and $\rho_o$ is the density of the surrounding fluid. The pressure and velocity of the acoustic field in the absence of the particle are described by p and v, respectively, and the brackets correspond to a time-averaged quantity. The terms $f_1$ and $f_2$ are the contrast terms that determine how the mechanical properties (compressibility and density) of the particle differ from the background medium. They are given by:

$$f_1 = 1 - \frac{\beta_p}{\beta_o} \quad (2a)$$

$$f_2 = \frac{2(\rho_p - \rho_o)}{2(\rho_p - \rho_o)} \quad (2b)$$

The subscript p corresponds to intrinsic properties of the particle. The force F acting on a particle is related to the gradient of the force potential U by:

$$F = -\nabla U \quad (3)$$

Particles will be localized at positions where the potential U displays a minimum (stable equilibrium). The acoustic contrast of a particle (or medium or fluid) is determined by the density and compressibility differences between it and the background medium or fluid as defined by terms $f_1$ and $f_2$ in Eqs. 2a and 2b. The relative magnitudes and signs of $f_1$ and $f_2$ determine the behavior of the radiation force potential U and thus determine the magnitude and direction of the acoustic radiation pressure force. As an example, if a particle and the background medium or fluid share the same density value ($\rho_p = \rho_o$), then $f_2$ is zero and the acoustic contrast is due only to compressibility differences in $f_1$. If both $f_1$ and $f_2$ are zero, then acoustic contrast is zero. Viscosity and thermal conductivity will also have effects on acoustic contrast, but theses are widely neglected in the literature. Equation 1 is generally sufficient to describe the acoustic contrast relationship for most samples of interest.

As used herein "a" means one or more.

As used herein "assaying" means a method for interrogating one or more particles or one or more fluids.

As used herein "assay" means a product, including but not limited to, an assay kit, data and/or report.

As used herein "flow cell" means a channel, chamber or capillary having an interior shape selected from rectangular, square, elliptical, oblate circular, round, octagonal, heptagonal, hexagonal, pentagonal, and triagonal.

As used herein "channel" means a course, pathway, or conduit with at least an inlet and preferably an outlet that can contain an amount of fluid having an interior shape selected from rectangular, square, elliptical, oblate circular, round, octagonal, heptagonal, hexagonal, pentagonal, and triagonal.

As used herein "acoustically focusing", "acoustically focused", "acoustically focuses" and "acoustic focusing" means the act of positioning particles within a flow cell by means of an acoustic field. An example of acoustic focusing of particles is the alignment of particles along an axis of a channel. The spatial extent of the focal region where particles are localized is determined by the flow cell geometry, acoustic field, and acoustic contrast. As viewed in the cross sectional plane of a flow cell, the shape of observed focal region can resemble a regular geometric shape (e.g. point, line, arc, ellipse, etc.) or be arbitrary. The primary force used to position the objects is acoustic radiation pressure. The acoustic systems of the present invention are sometimes referred to herein as flow cytometers, acoustic cytometers, flow cells or long transit time devices, however all such systems have acoustic radiation pressure.

As used herein "acoustically reorienting" and "acoustically reorients" means the act of repositioning the location of miscible, partially miscible, or immiscible laminar flow streams of fluid or medium within a device with acoustic radiation pressure. This technique utilizes differences in the mechanical properties (acoustic contrast) of separate laminar streams in a flow channel. When two fluids are brought into contact, a large concentration gradient can exist due to differences in their molecular makeup's resulting in an interfacial density and/or compressibility gradient (acoustic contrast between streams). For diffusion, time scales that are larger than the time scales of the acoustic excitation, the laminar flow streams can be acted upon with acoustic radiation pressure. Under the action of the acoustic field, the streams are reoriented within the flow cell with an acoustic field based upon their acoustic contrast.

As used herein "particle" means a small unit of matter, to include but not limited to: biological cells, such as, eukaryotic and prokaryotic cells, archaea, bacteria, mold, plant cells, yeast, protozoa, ameba, protists, animal cells; cell organelles; organic/inorganic elements or molecules; microspheres; and droplets of immiscible fluid such as oil in water.

As used herein "analyte" means a substance or material to be analyzed.

As used herein "probe" means a substance that is labeled or otherwise marked and used to detect or identify another substance in a fluid or sample.

As used herein "target" means a binding portion of a probe.

As used herein "reagent" is a substance known to react in a specific way.

As used herein "microsphere" or "bead" means a particle having acoustic contrast that can be symmetric as in a sphere, asymmetric as in a dumbbell shape or a macromolecule having no symmetry. Examples of microspheres or beads include, but are not limited to, silica, glass and hollow glass, latex, silicone rubbers, polymers such as polystyrene, polymethylmethacrylate, polymethylenemelamine, polyacrylonitrile, polymethylacrylonitrile, poly(vinilidene chloride-co-acrylonitrile), and polylactide.

As used herein "label" means an identifiable substance, such as a dye or a radioactive isotope that is introduced in a system, such as a biological system, and can be followed through the course of a flow cell or channel, providing information on the particles or targets in the flow cell or channel.

As used herein "signaling molecule" means an identifiable substance, such as a dye or a radioactive isotope that is introduced in a system, such as a biological system, and can be used as a signal for particles.

As used herein "inherently axially symmetric" means an object that displays a high degree of axial symmetry. Examples of inherently axially symmetric geometries include oblate circular cross section cylinders, elliptical cross section cylinders, and oval cross section cylinders, but not limited thereto.

Field based focusing of particles via magnetic fields, optical fields, electric fields and acoustic fields, enables the localization of particles without the need for sheath fluid. Focused particles can be flowed past interrogating light sources at whatever linear velocity is chosen using an adjustable external pumping system such as a syringe pump. Field based focusing also concentrates particles in the medium which allows for high particle analysis rates without the need to pre-concentrate samples. Field based focusing for flow cytometry, where particles are analyzed one by one, has been accomplished with dielectrophoretic and acoustic systems. This can be done using other fields, such as magnetic fields, optical fields or electrophoretic fields.

Field based focusing of particles relies on contrasts in physical properties between the particle being focused and the medium. For dielectrophoretic focusing, this relies on dielectric properties. For magnetic focusing, magnetic susceptibility and for acoustic manipulation this relies on acoustic properties, primarily density and compressibility.

Magnetic focusing of cells typically requires binding of magnetic material to the cells and dielectrophoretic focusing typically requires careful control of the media conductivity as well as very small dimensions for high field gradients. This makes acoustic focusing particularly attractive for many analytes as it typically does not require reagents to change the contrast of particles and can be performed in relatively large dimension channels with complex one or more media of highly variable conductivity and or pH.

Referring now to FIG. 1, a schematic comparison of planar microchannel focusing 103 and 105 and line driven capillary focusing 107 and 109. Planar focusing results in a two dimensional sheet of particles 102 with varying velocities arrows along the flow direction. Cylindrical line drive focusing places particles 102 in the center where they travel at the same rate single arrow.

Particle Manipulation in Acoustically Driven Capillaries

To calculate the acoustic force on particles within an ultrasonic standing wave, the acoustic radiation pressure force on a compressible, spherical particle of volume V in an arbitrary acoustic field can be written in terms of an acoustic radiation pressure force potential U (Gor'kov 1962):

$$U = \frac{4}{3}\pi a^3 \left[ \left(\beta_0 \frac{\langle p^2 \rangle}{2}\right) f_1 - \frac{3}{2}\left(\frac{\rho_0 \langle v^2 \rangle}{2}\right) f_2 \right]. \quad (1)$$

Here, a is the particle radius, $\beta_o$ is the compressibility of the surrounding fluid, and $\rho_o$ is the density of the surrounding fluid. The pressure and velocity of the acoustic field in the absence of the particle are described by p and v, respectively, and the brackets correspond to a time-averaged quantity. The terms $f_1$ and $f_2$ are the contrast terms that determine how the mechanical properties of the particle differ from the background medium. They are given by:

$$f_1 = 1 - \frac{\beta_p}{\beta_o} \quad (2a)$$

$$f_2 = \frac{2(\rho_p - \rho_o)}{2(\rho_p - \rho_o)} \quad (2b)$$

The subscript p corresponds to intrinsic properties of the particle. The force F acting on a particle is related to the gradient of the force potential U by:

$$F = -\nabla U \quad (3)$$

Particles will be localized at positions where the potential U displays a minimum.

According to one embodiment of the present invention a round or oblate cross-section capillary that acoustically focuses particles either along the axis of the capillary or along the capillary wall is tuned with an acoustic wave. The position of the particle within the capillary depends upon the value of its density and compressibility relative to the background medium as shown in the acoustic contrast terms $f_1$ and $f_2$ above.

A cylindrical geometry according to one embodiment of the present invention creates a radial force profile with radial restoring forces that hold the particles in a single stream line along the axis of the flow. This affords single file particle alignment along the axis of the capillary while using only a single acoustic excitation source. There are several benefits identified with the cylindrical (inherently axially symmetric geometries such as oblate cylinders, ellipses, etc.) for particle manipulation. The benefits include: higher throughput on the order of several ml/min versus several hundred μl/min per fluid channel. Fine positioning of blood cells along the axis of a capillary at flow rates of 0 to 5 mL/minute have been achieved in 340 micron diameter capillaries.

Figures 2A, 2B:
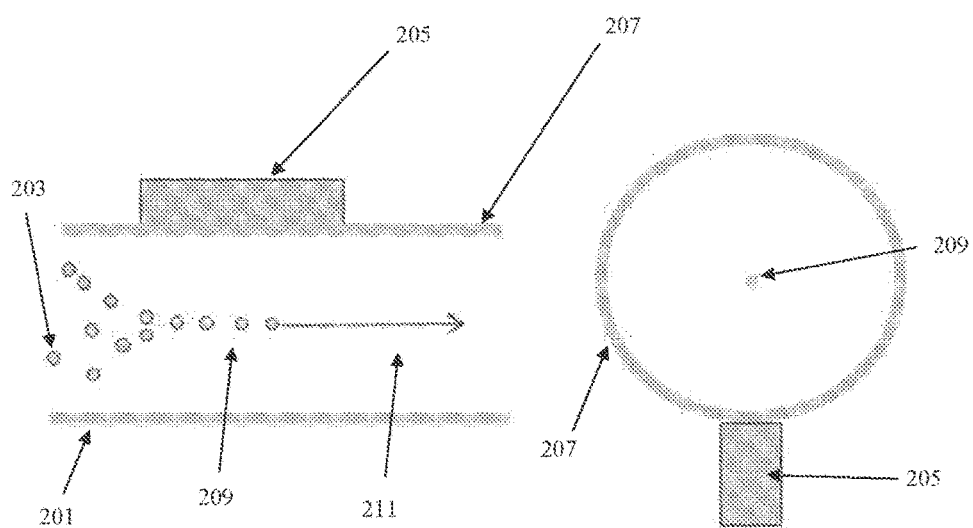
FIGS. 2A and 2B illustrate a single line acoustic focusing device according to one embodiment of the present invention.

Referring now to FIG. 2, a single line acoustic focusing apparatus is illustrated according to one embodiment of the present invention. FIG. 2 gives a side view A and axial view B of a cylindrical tube 201 acoustic focusing device that acoustically focuses particles 203 to a pressure minimum in the center of the tube 209 by transducer 205. The stream of particles is sent to analysis 211. Analysis includes any post focusing interrogation or further processing. The flow cell is not limited to a tube or a cylindrical shape.

The particles are maintained in a single velocity stream line that allows uniform residence time for similar size and acoustic contrast particles. This is important for any process for which reaction kinetics are important.

Radial force driven acoustic focusing of particles coupled with tight central focusing of a light source on the particles allows analysis of particles one by one as in a flow cytometer and simultaneous concentration of the particles. This type of analysis is much more powerful than a simple fluorescent readout step as it allows multiplexed identification and quantification of each particle/assay as well as single particle statistics.

Acoustic Manipulation of Background Media

According to another embodiment, a method for acoustically reorienting a medium provides that the medium within the device is acoustically manipulated in addition to the position of the particles. This embodiment utilizes differences in the mechanical properties (acoustic contrast) of separate laminar streams in a flow channel. As used herein, medium is used interchangeable with fluid.

Figure 3:
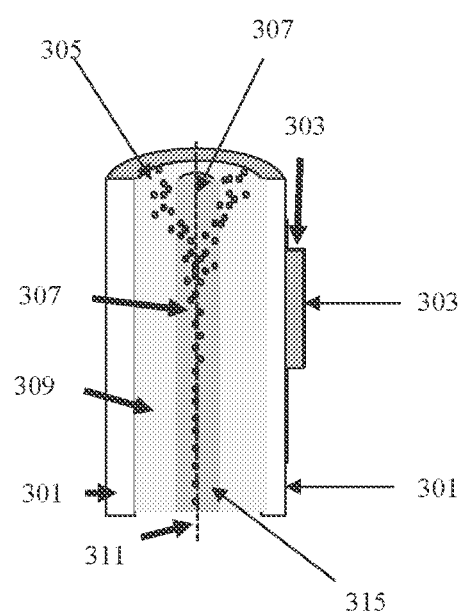
FIG. 3 illustrates a schematic of an acoustically driven flow cell focusing particles to the center of a flowing liquid stream across laminar flow lines according to one embodiment of the present invention.

Referring now to FIG. 3, a schematic of a line driven capillary 301 acoustically focusing particles to the center of a flowing fluid stream 311 comprising clean fluid 307 as the particles move across laminar flow lines 315 is illustrated according to one embodiment of the present invention. Particles in sample 305 are acoustically focused from sample stream 309 and can be tightly acoustically focused for single file analysis. Wash buffer 307 provides fluid stream in which particles are finally contained. Transducer 330 provides acoustic standing wave.

Figure 4A:
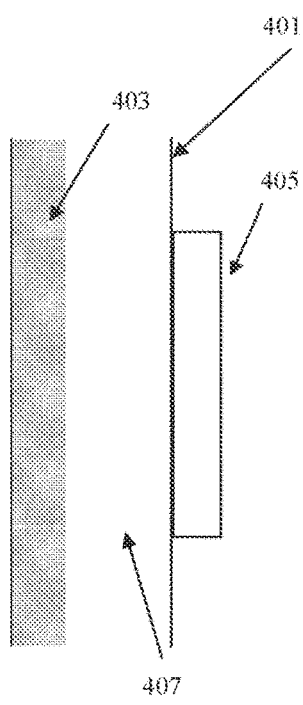
FIGS. 4A and B illustrate one embodiment of an acoustically driven flow cell with two laminar flow streams in contact.
Figure 4B:
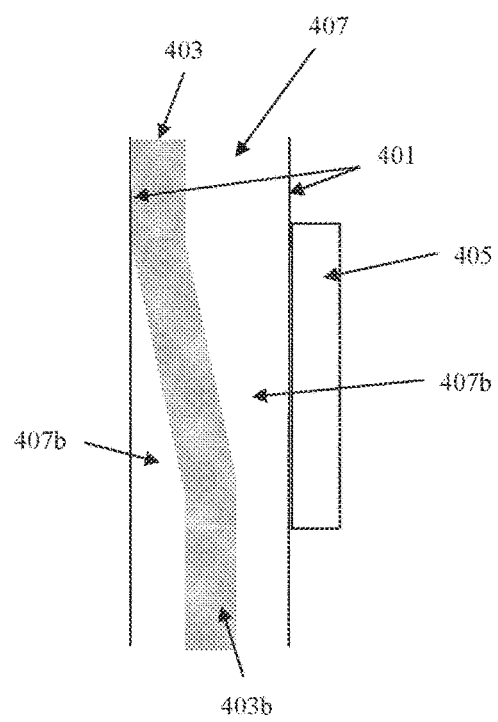

Referring now to FIG. 4, one embodiment of an acoustically driven capillary 401 and 405 with two laminar flow streams 403 and 407 in contact is illustrated in FIG. 4A. Upon activation of the acoustic field in FIG. 4B, the positions of the fluid streams are acoustically reoriented based upon the acoustic contrast of each stream. In one embodiment, the flow stream with greater acoustic contrast 403b is reoriented to the center of the acoustically driven focused capillary while the flow stream with lower acoustic contrast 407b is acoustically reoriented near the capillary walls. In FIG. 4A, the acoustic field is OFF and streams flow parallel down the channel. As illustrated in FIG. 4B, when the acoustic device is activated in a dipole mode, Stream 1 403a moves coincident with the central axis of the capillary partially displacing Stream 2 407b. Equations 1-3 approximate the stream that is more dense and/or less compressible is forced to the central axis position. Flow direction is downward on the plane of the page.

Equations (Eqs.) 1 and 2 describe an acoustic contrast that predicts the magnitude and direction of the acoustic radiation pressure force on particles in a fluid or medium. The force depends upon the differences in the density and/or compressibility of a particle relative to the density and/or compressibility of the background medium. Although this type of effect has traditionally been used to study particles, emulsions, and bubbles in fluids, it has also been applied to extended objects in fluids. For example, the acoustic radiation pressure force has been shown to effectively stabilize liquid bridges of silicone oil in water. It was observed that liquid bridges density-matched to a background water medium can be driven with modulated acoustic radiation pressure. The force results from a difference in the compressibilities (acoustic contrast) of the liquid bridge and background medium. Similarly, experiments using air as a background medium have proven the acoustic radiation force is effective for the manipulation of both small diffusion flames of natural gas and dense gases surrounded by air.

The effect shown in FIG. 4 takes advantage of differences in the composition of the laminar flow streams. The streams can be immiscible, partially-miscible, or miscible. When two fluids are brought into contact, a large concentration gradient can exist due to differences in their molecular makeups. For immiscible fluids, this interface is assumed to be infinitely narrow. For miscible fluids, the concentration gradient is a transient interfacial phenomena that relaxes over time due to diffusion and other transport mechanisms. For the description of acoustic processes, the concentration gradient is viewed as a density and/or compressibility gradient. For diffusion time scales that are much larger than the time scales of an acoustic excitation, the laminar flow streams can be considered isolated entities with different densities and compressibilities (acoustic contrast) that can be acted upon with acoustic radiation pressure. Multiple laminar stream systems have been developed where the flow streams are manipulated consistent with the density and compressibility relationships shown in Eqs. 1 and 2. Examples of these systems are illustrated herein.

It should be noted that Eq. 1 is approximated in the long wavelength limit, where it is assumed that the particle acted upon by the acoustic radiation pressure force is much smaller than the wavelength of sound excitation $\lambda \gg a$). It also ignores multiple scattering from the particle. (Contributions from wave reflections at the media interfaces to the resident acoustic field can also become considerable as the acoustic contrast between streams increases.) For this reason, it is assumed that Eq. 1 is not an exact description of the interaction of the acoustic field with the laminar flow streams in the devices described here. Acoustic radiation pressure induced manipulation of miscible laminar flow streams of diameter b in the limit where $\lambda \gg b$ is upheld, as well as for larger diameter streams where $\lambda \sim 4 b$, have been observed. Equations 1-2 serve as qualitative predictors for the location of the final stream position by defining a relationship between the relative density and compressibility of the streams within the flow channel. Corrections to the final shape of the streams due to shaping associated with acoustic radiation pressure and gravity will affect their final cross sectional geometry within the cavity, but the approximate position of the stream is still predicted by density and compressibility contrasts (acoustic contrast).

FIGS. 5A-5D illustrate the separation of micron sized polystyrene fluorescent orange/red particles from a background of nanometer sized green particles in homogeneous media according to one embodiment of the present invention. The time-averaged acoustic force scales with the volume of a cell/particle. Because of this it is possible to fractionate particles not only by acoustic contrast to the media but also by size. By flowing a clean stream in the radial center of a separation device however, it is possible to prevent the smaller particles from reaching the center before the point of axial particle collection. Furthermore, if the center stream has higher specific gravity and/or lower compressibility than the outer sample stream, the particles/cells with greater acoustic contrast than the center wash fluid will continue to focus to the capillary axis while particles/cells of lesser contrast will be excluded.

Referring now to FIG. 5A, polysciences fluoresbrite polychromatic red 5.7 μm latex particles are mixed with Polysciences 200 nm fluoresbrite green particles in the coaxial stream. A particle stream flowing through the capillary under epi-fluorescent illumination (FITC long-pass filter) with acoustic field off is illustrated. FIG. 5B is an activation of the acoustic field that acoustically focuses the 5.7 μm particles (which fluoresce yellow under blue illumination) to a line along the central axis of the capillary, leaving the 200 nm particles not acoustically focused and remain in their original flow stream. The 5.7 μm particles are like particles with like acoustic contrast. FIG. 5C shows green illumination with red band pass filter. The 5.7 μm particles fluoresce red while the 200 nm particles are not excited. FIG. 5D illustrates clean core stream 507 introduced alongside coaxial stream containing fluorescent background 505. Transducer 503 includes acoustic standing wave (not shown). Particles 509 are acoustically focused upon entering standing wave. The acoustically focused particles cross from sample stream 509 to core stream 507 and thereby are removed from sample fluid.

Figures 6A, 6B, 6C:
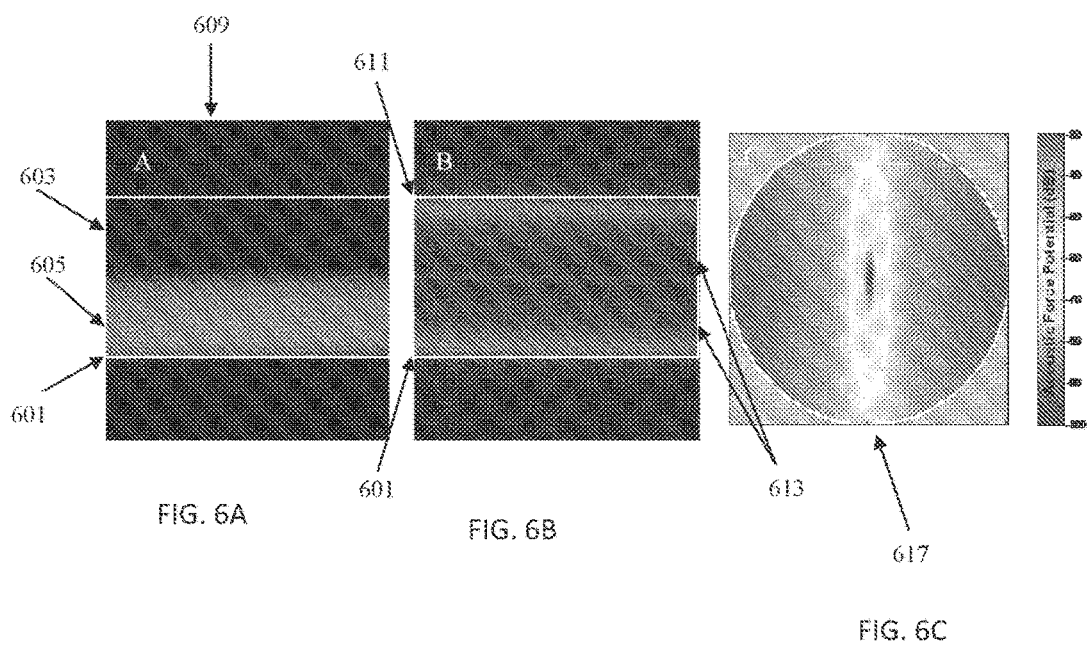
FIGS. 6A-6C illustrate particle separation across laminar flow boundaries for particles of different size according to one embodiment of the present invention.

Referring now to FIG. 6, particle acoustic focusing of particles across laminar streams and acoustic reorientation of medium is illustrated. FIG. 6A illustrates the fluorescence image of an optical cell coupled to the end of an acoustic focusing cell with acoustic field off. White lines are added to indicate edges of 250 μm flow cell. Excitation light passes through a 460 nm bandpass filter and emission is filtered through a 510 nm long-pass filter. Flowing through the bottom half of the flow cell is a mixture of 10% whole blood in PBS buffer spiked with 25 μg/ml of R-Phycoerythrin fluorescent protein (orange fluorescence). White blood cell DNA is stained with SYTOX green. At the top is 6% iodixanol in PBS buffer (dark).

FIG. 6B illustrates the same optical cell and media after acoustic field is turned on. The 6% iodixanol in PBS buffer acoustically reorients to center while the PBS/PE/blood plasma mixture is acoustically reoriented toward both the left and right sides of the cell (top and bottom in the figure). The white cells leave their original medium and are acoustically focused to the center where they are observed as a green line. Red cells also acoustically focus to this location but are not visible in the fluorescent image.

FIG. 6C illustrates MATLAB plot of the approximate acoustic force potential (Eqs. 1 and 2) for particles that are more dense/less compressible than the background. This is an axial view of an acoustically driven capillary with an extended source aperture (flow is into the page). More dense, less compressible particles/media e.g. cells and iodixanol/PBS medium, are acoustically focused/acoustically reoriented toward the center (dark blue region) and less dense and/or more compressible media e.g. PBS/PE/blood plasma mixture are acoustically focused/acoustically reoriented toward the left and right sides (dark red regions).

When separating particles or cells using heterogeneous media in which the wash stream fluid's specific gravity and/or compressibility (acoustic contrast) differs from that of the sample fluid stream, the separate laminar streams can be affected by the acoustic field. For example, if blood cells are to be separated from the protein in serum and the wash stream has higher specific gravity/lower compressibility, then the entire sample stream is pushed toward the center of the fluid cavity (e.g. capillary axis in an acoustically driven capillary). This condition is met when even very dilute blood in physiological saline is the sample stream and physiological saline is the wash stream. If however, the wash stream is made to have higher specific gravity/lower compressibility than the sample stream, but lower specific gravity/higher compressibility than the cells, the wash remains in the central core, the cells move toward the center of the cavity and the sample medium is pushed to the sides.

Modeling for the acoustic field distribution shows where the sample media should approximately be positioned for the case described above (FIG. 6C). Using Eq. 1-3, a potential minimum exists in the center of the capillary for particles (or approximately for flow streams) that possess higher specific gravity/lower compressibility. Conversely, particles (or flow streams) that possess lower specific gravity/higher compressibility will be positioned at the potential maxima in the figure as the sign is reversed in Eqs. 2. An interesting result occurs when a sample stream of lower density (and/or higher compressibility) is flowed along the axial center of the capillary and a higher density (and/or lower compressibility) fluid stream is flowed adjacent to it. The streams will acoustically reorient to comply with the potential shown in FIG. 6C. This kind of stream separation has not been demonstrated or reported in planar systems.

The ability to place samples in the central core stream and still separate the sample fluid from the cells or particles can be used to increase throughput. The acoustic force is strongest near the minimum potential U in FIG. 6C and the distance the particle must travel to the minimum is minimized.

The data in FIG. 6 shows that phycoerythrin in the acoustically reoriented streams is positioned further from the center of the flow stream than with the acoustic field turned off. This may be used to advantage in an in-line system designed to exclude free antibody or other species, for example, particularly for slow flow rates/long residence times where diffusion might otherwise significantly penetrate the wash stream.

Figure 7A:
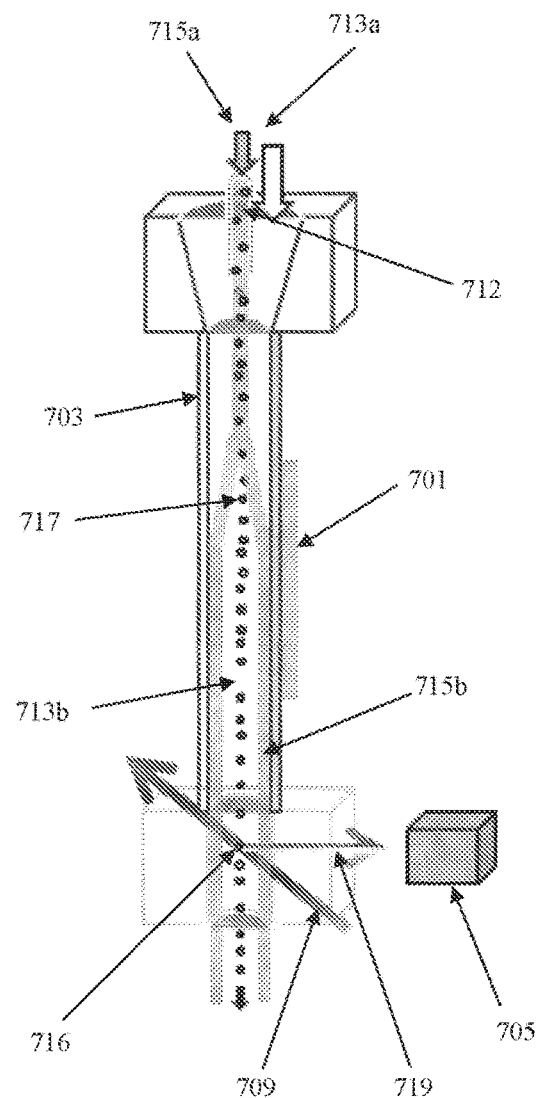
FIGS. 7A-C illustrate multiple embodiments of analysis in a flow cytometer like configuration for particles.
Figure 7B:
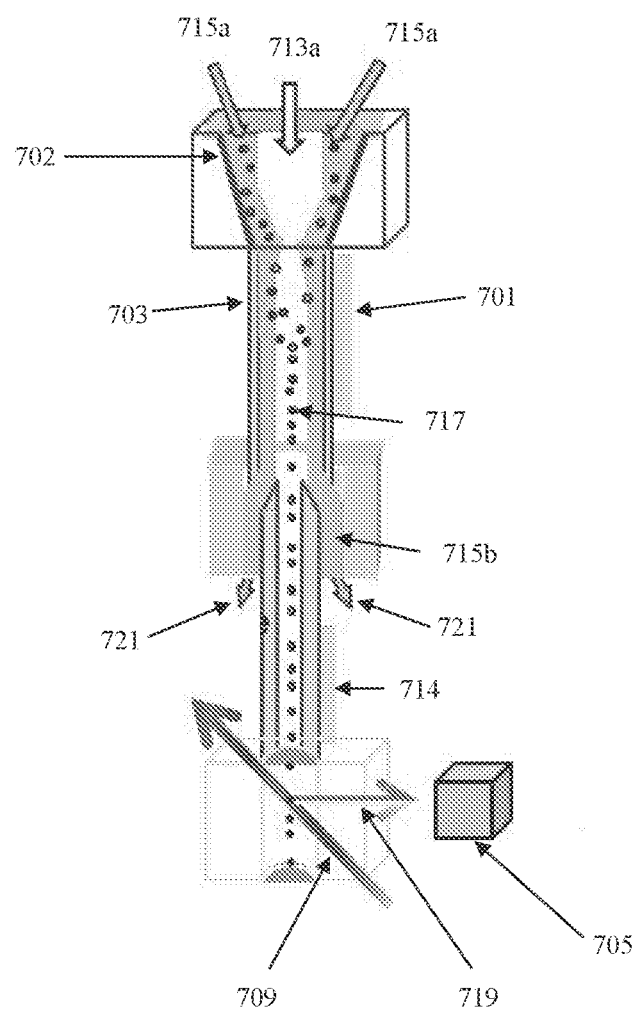
Figure 7C:
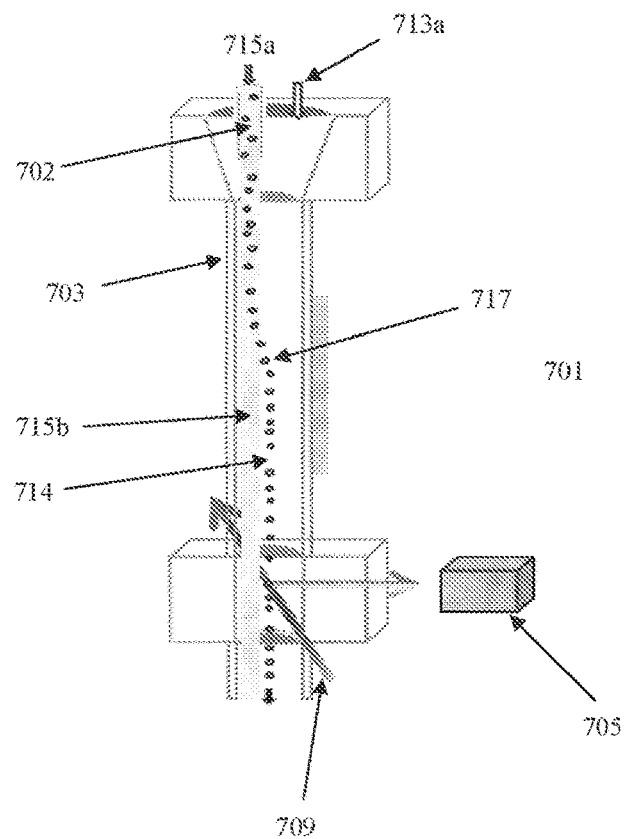

Referring now to FIG. 7, analysis in a flow cytometer like configuration where cells/particles are paraded through a tightly focused laser, illustrated such that the laser can be focused so that it does not excite the "dirty" media (FIG. 7A). Alternatively, the clean stream can be flowed independently through the optics cell (FIG. 7B). For this method clean media and target cells reach the detection region but the particles may need refocusing by a second focusing element. If the sample is injected slightly to one side of center and the stream is a small enough fraction of the total flow, the sample stream can be confined to one side of the optics cell (FIG. 7C). This is advantageous in flow cytometry for separating free vs. bound fluorophores in the analysis region.

Referring now to FIG. 7A, an embodiment of the present invention comprises sample 715a which is introduced into the system alongside wash buffer 713a. Particles 712 in sample 715, sample 715 and wash buffer 713 are introduced into capillary 703a. A line drive 701 on capillary 703 introduces acoustic standing wave (not shown) naming a user defined mode (dipole mode is this example). The sample 715a and buffer 713a are acoustically reoriented and particles are acoustically focused based upon the acoustic contrast of each. Acoustically focused particles 717 are transited to an interrogation point 716 where laser 717 impinges electromagnetic radiation. An optical signal from the interrogated sample 719 is detected by the detector 705. The detector may be a PMT array for example.

Referring now to FIG. 7B, sample 715 comprising particle 702 is introduced into the system. The sample 715a, wash buffer 713a and particle are introduced into capillary 703. An acoustic wave (dipole mode) is induced into the capillary 703 by a first acoustic wave inducing means 701 such as a PZT drive but not limited thereto as other acoustic wave inducing means will produce same standing wave. Acoustic focusing of particles 702 cause each particle to be acoustically focused such that each particle having high enough acoustic contrast will focus in a line 717. Sample buffer with a lower concentration of particles after acoustic focusing will be discarded to waste 721 buffer 713 and 717 particle will be transited to a second acoustic wave inducing means 714. Particles are interrogated with a laser 709. The optical signal 719 for interrogated sample is sent to detector 705.

Referring now to FIG. 7C, sample 715 comprising particle 702 and buffer 713 are introduced into the system. Sample 715 flow next to capillary wall 703 and buffer 713a flows against the opposite wall. Transducer 717 induces acoustic wave that acoustically reorients sample 715b, acoustically focuses particles 714 and acoustically reorients buffer 713b. The particles 714 are transited to the interrogation point for interrogation of the particles 714 and buffer 713b by laser 709. The optical signal from interrogated particle 714 and/or buffer 713b is detected by detector 705. The velocity of the sample stream, buffer stream, particles is controlled by pumping system (not shown) such that the velocity is variable between 0 meters/second to 10 meters/second in the forward, reverse or stopped direction. Particles are washed in an acoustically reoriented first fluid which replaces the second fluid to produce washed particles.

One aspect of one embodiment of the present invention provides for an acoustic particle focusing technology in a cytometer that is capable of both high particle analysis rates up to 70,000 particles/second and/or capturing images from user selected subpopulations of cells.

Another aspect of one embodiment of the present invention provides for a system and method to analyze more than one hundred thousand cells per minute using traditional flow cytometry measurements and periodically adjust the velocity of the focused stream to collect images of only those cells that meet user defined criteria.

A further aspect of one embodiment of the present invention provides for a system and method wherein a first and a second fluid are acoustically reoriented and wherein the second fluid suppresses non-specific binding of a reagent that binds to a population of the particles.

Yet another aspect of one embodiment of the present invention provides for a system and method wherein particles are acoustically reoriented from a first fluid to a second fluid. The second fluid has a higher concentration of particles suspended therein after acoustically focusing the particles as compared to the second fluid prior to acoustically focusing the particles. Acoustically focusing the particles preferably creates a line of particles through about a center axis of a channel that flows parallel to an axis of flow.

Figure 8:
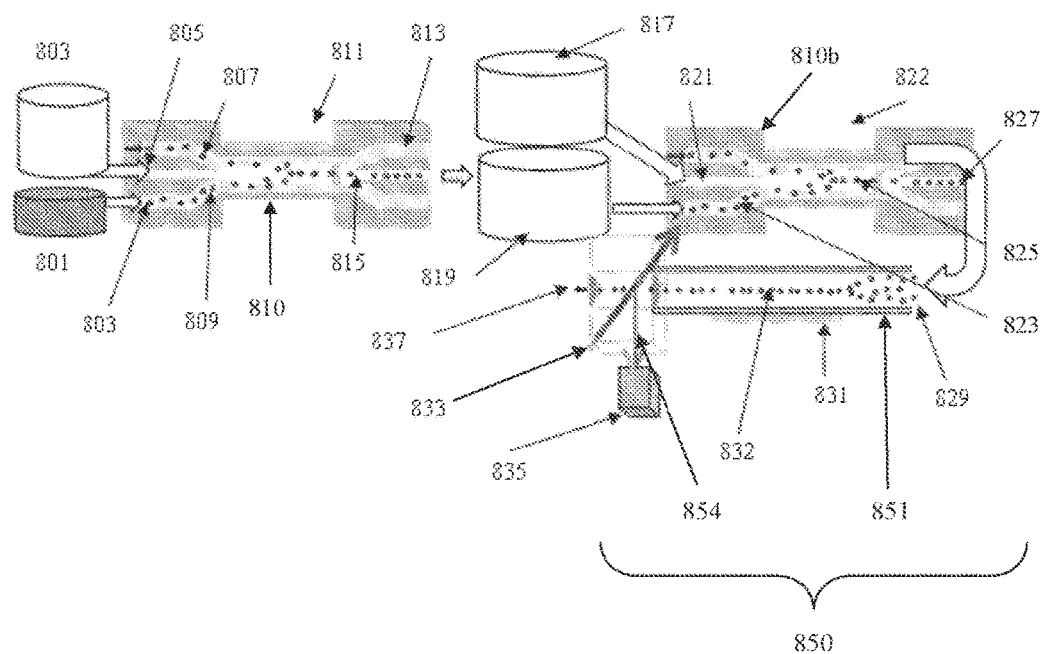
FIG. 8 illustrates a schematic of an acoustically focused flow cell in combination with an acoustic flow cytometer according to one embodiment of the present invention.

FIG. 8 illustrates an embodiment of the present invention comprising a schematic of an acoustically focused flow cell for acoustically orienting particles and flow streams prior to collecting the acoustically focused sample. The sample 801 is introduced into a flow cytometer 850 that contains a transducer 831 for acoustically focusing particles 832 prior to analysis. Sample container 801 comprising sample particles 803, 807 and 809 is introduced to a flow cell 810. A transducer 811 provides acoustic wave to flow cell 810 to produced acoustically focused particle 815. Wash or other reagent 802 in introduced to flow cell 810. Particles 809 and 807 are acoustically focused into stream 805. The acoustically focused particle 815 exists with the wash stream 815 and is collected at collection/incubation site 819. Wash stream 821 is introduced from wash 817. Flow cell 810b with acoustic field generator 822 receives particles 823. The particles are acoustically focused 825 prior to introduction into the focus cytometer 850. A transducer 831 provides to flow cell 851 acoustic field and particles are acoustically focused 832 prior to reaching an interrogation point 852. Interrogation light 833 impinges on particle. A signal 854 from impinged particles is sent to detector 835 for analysis. The particle flows through system to point 837 for collection. In this embodiment, sample particles 803, 807 and 809 preferably have a particle acoustic contrast that is different from the acoustic contrast of sample container 801.

Advantages of Controllable Flow

The ability to control the linear velocity of particles in a stream for a field focused system while maintaining high particle analysis rates in relatively large dimension channels enables improved analysis of particles and practical analysis of particles in ways that were previously not feasible.

By using lower linear velocities than conventionally used in flow cytometry and allowing each particle to spend longer times in the interrogation light, for example a laser, one can achieve the extremely high sensitivity seen in slow flow hydrodynamic systems without the drawbacks of clogging and low throughput. In addition, the utility of markers that are not typically used in cytometry because of fast transit times can be greatly increased. Among these markers are luminescence probes such as lanthanides and absorptive dyes such as cytological stains and trypan blue. Imaging of particles is also much more easily achieved by using slow flow or even stopped flow without resorting to specialized tracking technology like that used in imaging hydrodynamically focused particles (Amnis, Seattle, Wash.).

While nearly all labels currently used in cytometry would benefit from lower laser power to reduce photobleaching and non-radiative states and the longer integration of signal afforded by longer transit times, some that will benefit more than others are discussed herein. These include fluorophores/luminophores that have long lifetimes and or low quantum yields/extinction coefficients. Most chemi bioluminescent species also benefit tremendously from longer transit times as their energy is given off on time scales much greater than those used in conventional cytometry analysis. Long lifetime labels are for example labels with life times greater than about 10 ηs For example: labels with life time between about 10 μs to about 1 μs, labels with life times between about 1 μs to about 10 μs labels with life times between about 10 μs to about 100 μs, or labels with life times between about 100 μs to about 1 ms and above.

Figure 9:
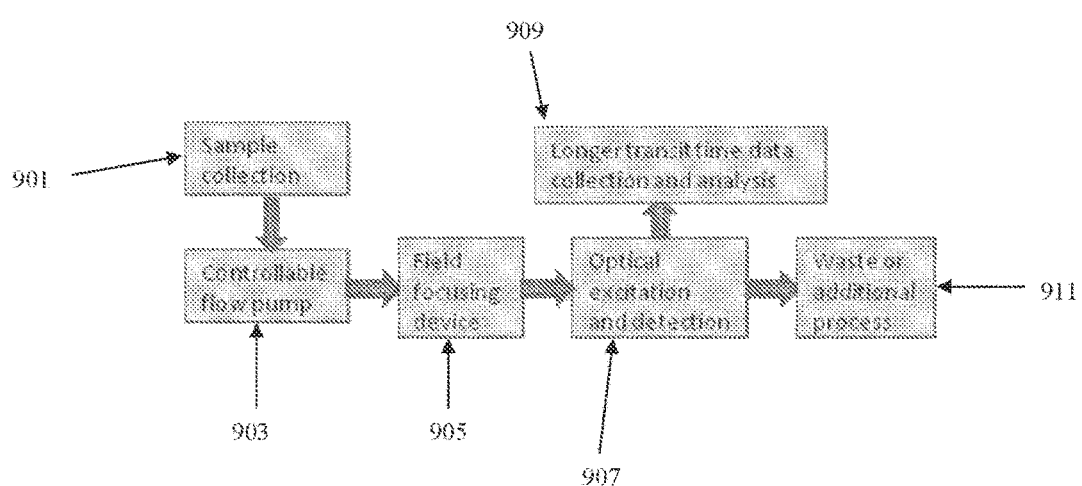
FIG. 9 illustrates a flow diagram according to one embodiment of the present invention.

One aspect of the present invention provides for controllable linear velocity ranging from 0 m/s to 10 m/s without compromising core diameter and particle concentration. In a preferred embodiment the linear velocity is in the range of about 0 m/s to about 0.3 m/s. In a more preferred embodiment the linear velocity is in the range of about 0.3 m/s to about 3 m/s. In a more preferred embodiment the range is between about 3 m/s to about 10 m/s. Referring now to FIG. 9, a flow diagram illustrating one embodiment of the present invention is illustrated. A field based means 905 focuses particles into a line or plane, preferably acoustically. The particles are transited through the system preferably by a pumping system 903 that can be adjusted to the desired flow rate for the desired linear velocities. A means for optical excitation 907 of the particles and a means for collection and analysis 909 of fluorescent/luminescent light given off by the sample comprising the particles. Average linear fluid velocity is given by the flow rate divided by the cross sectional area but particles will generally travel at nearly the same speed as the fluid lamina they are in. Particles focused to the center of a channel for most channel geometries used would travel about twice the average velocity. Preferably, the system provides possible pulsed or modulated excitation at slower rates, data systems to accommodate longer transit times and slower pulse rates and reduced waste that can readily be run again or transferred to another process 911 without concentration.

Slowing Linear Velocities—Single-Line Focused System

One embodiment of the present invention comprises a method to improve signal is by increasing the number of photons given off by a fluorescent/luminescent label by illuminating it for a longer time period with a continuous light source. and particles with a linear velocity of 0.3 m/s, this number increases over the prior art by about 10 fold. At this velocity and assuming an average of 100 microns distance between particle centers, about 3000 particles per second can be analyzed. It is the combined ability to focus particles and concentrate them that allows these long transit times for high particle analysis rates. If the velocity is further decreased to 0.03 m/s, 100 fold more photons would be given off and 300 particles per second could be analyzed.

In another example, semiconductor nanocrystals also referred to as quantum dots are highly resistant to photobleaching, so the gains predicted in the above example might not be so dramatic for other fluorophores that are prone to photobleach. All fluorophores however, are limited in continuous excitation by a power threshold that achieves "photon saturation" by exciting a maximum number of the fluorophores at any given time. Any more excitation photons will not produce any more fluorescence and will in fact decrease fluorescence by increasing photobleaching or exciting to non-radiative states. Often, one must balance excitation power with photobleaching rate and non-radiative state excitation such that the most fluorescence is emitted for a given transit time. In short, longer transit times will yield more photons for a given excitation power, but reducing light source power can further yield more photons per fluorophore during the analysis time. This is particularly important for high sensitivity applications in which very few labels may be bound to the target. Lower laser power also reduces fluorescent background, which can further increase sensitivity and resolution of particle populations.

Slower linear velocities can increase the signal from any label, but it also makes it practical to use dimmer labels and long lifetime labels that are not commonly used for lack of photon yield in short transit times. Lanthanide chelates, for instance, have very long Stokes shifts and very narrow emission wavelengths so they can be highly specific labels but they will emit relatively few photons over a short transit period. Nanoparticles using europium, for instance, may have lifetimes of about 0.5 milliseconds. In a field focused system, transit times can be slowed to milliseconds or more allowing several cycles of excitation and emission to be monitored. Downstream optics are not required.

Pulsed or Modulated Excitation

According to one embodiment of the present invention an excitation source is pulsed or modulated. Many commercial light sources are available to do this by affecting the light source itself and using digital or analog control. Methods such as chopper wheels and acoustoptic modules can also modulate the interrogation light source externally. For some applications it is also desirable to sync the detectors with the light source in time such that events can be correlated to excitation peaks or valleys. Correlating a Rayleigh scatter detector that detects light scattered from passing particles with the fluorescence detector(s) in time is one preferred method. Lock-in amplification can be used to help eliminate electronic noise at frequencies other than the modulation frequency but averaging to eliminate noise can be accomplished digitally if the data is collected in a digital format.

Using pulses with relatively long rest times that allow relaxation from triplet states can increase the overall fluorescence yield of fluorophores vs. equivalent power strong continuous wave excitation. This is again of particular importance to high sensitivity applications where only a few fluorophores are present. For a slow transit system, as in the present invention, particularly a field focused system, 67 pulses with microsecond timing can be monitored for a 0.3 m/s linear velocity for probes such as perCP where the triplet state is estimated to be about 7 microseconds. Pulsed or modulated light sources have the additional advantage of allowing phased locked amplification or averaging of time correlated data, either of which will reduce electronic noise.

Photobleaching of Undesired Fluorescence

One can take advantage of labels that have a high resistance to photobleaching by strongly illuminating a cell or particle having undesired fluorescence (often cellular autofluorescence) or the medium the particle is in, e.g. serum. The use of long transit times to accomplish this allows more photobleaching for a given excitation power. While in-flow upstream photobleaching is effective in a long transit time system, it can also be done in the present invention with a single light source in a long transit time system by examining the signal as the cell passes. The fluorescence of the less resistant species will decrease more quickly than that of the resistant specific label. This decrease not only increases specific signal to noise but the rate of decay can also be used to separate the non-specific signal from the specific signal by allowing a quantitative subtraction of the autofluorescence present. Quantum dots are an example of a good label for this purpose not only because of their high photobleaching resistance but because of their long Stokes shift. The Stokes shift can move the signal out of the primary cellular autofluorescence peak which improves signal to noise already but it also opens that spectral wavelength for use of an additional detector to monitor the auto-fluorescence. This by itself has been used to subtract cellular auto-fluorescence but the technique could be made more effective by also monitoring the decay rate. Decay rate can also be used to compensate bleed-through for different channels (colors) of fluorescence. If, for example a particle is labeled with both fluorescein and phycoerythrin and is excited with 488 nm light, the relative decay in the green and red channels can be used as a quantitative measure of how much fluorescein fluorescence is picked up by the red channel. This method improves compensation accuracy and eliminates the need for running compensation controls.

New Useful Probes

Lanthanide chelates, especially those using europium and terbium have dominated the time resolved probe market. These complexes are generally excited by wavelengths shorter than 400 nm but developments in these probes, e.g. Eu(tta)3DEADIT (Borisov and Klimant), have resulted in complexes that can be very efficiently excited by 405 nm light. This is significant because the low cost, high quality 405 nm diode lasers developed in the entertainment industry promise to lower the cost of violet excitation. Many other metal ligand complexes excited at a variety of wavelengths have high potential for use in longer transit time cytometers.

The list can be further increased by including luminescence resonance energy transfer (LRET) probes which general combine a long lifetime fluorophore like a metal ligand complex with a shorter lived dye. Lackowiz, Piszczek and Kang (2001) found that in such complexes it was possible to achieve a high quantum yield fluorophore by combining a low quantum yield metal ligand complex donor with a high quantum yield acceptor by combining a ruthenium ligand complex with short lifetime dyes.

These types of tandem probes are particularly useful in a long transit time cytometer because the long lifetime of the donor and the short lifetime of the acceptor combine to give a medium lifetime probe that would have too long a lifetime for a conventional cytometer but a short enough lifetime to increase throughput in a long transit time cytometer. For example, the ultra long lifetime of a terbium complex in a DELFIA™ assaying format has a lifetime of 1045 microseconds as compared with a Terbium fluorescein complex in a LanthaScreen™ assaying which has a lifetime of 160 microseconds. Lifetime can also be manipulated with changes to the metal chelating ligands (Castellano et at. 2000). With numerous possible metal ligand complex as donors and no limit to the number of acceptors many useful probes can be developed on the basis of spectral and lifetime properties. The multiplex idea can be carried even further using probes having several differing lifetimes e.g. short, medium and long that can be resolved individually by lifetime. A great advantage for the lifetime multiplexing scheme is that the same detectors can be used for overlapping colors, e.g. a fluorescein/terbium complex can be used in conjunction with plain fluorescein.

Qdots® although shorter lived than luminescent probes, have lifetimes that are long enough (~10-100 ns) to be well separated from most conventional fluorophores and short enough to be used in conventional cytometers but the practical use of lifetimes on this scale has been limited. Developments in high speed detectors, lasers and electronics make this more practical.

Other luminescent materials such as phosphors and up-converting phosphors have not achieved success in bioassaying, largely due to their large size. These materials might be very useful however in multiplex beadsets for cytometry. Their emissions can be distinguished using time resolved techniques and the up-converting phosphors can be excited using long wavelength lasers that would not excite most fluorophores used in assaying.

Secondary Reagents

Secondary reagents using ligands such as biotin, streptavidin, secondary antibodies and protein A and G will be of particular utility in inexpensive cytometers and long transit time cytometers. For instruments taking advantage of violet diodes, availability of violet excited dyes conjugated to the antibodies or other ligands necessary for assaying may be in short supply, so violet excited secondary conjugates will be very useful, e.g. Pacific Blue® or Orange® conjugated to streptavidin/biotin or protein A/G or anti-species specific or probe specific (fluorescein, PE, APC) secondary antibodies can all be used to increase the utility of an instrument with fewer lasers than are typically necessary to excite probes of choice. If, for example, assaying requires antibodies that are only available as unconjugated or conjugated to Fluorescein or PE or biotin needed to be performed in a violet only or a violet and red instrument, protein A or G or species specific secondary reagents can be used for unconjugated antibodies, labeled streptavidin for the biotin antibodies and anti-fluorescein or PE for the dyed antibodies. Qdots® are also excellent examples of violet excited labels that are typically used in a secondary format, usually streptavidin conjugates. Their broad excitation spectrum makes them particularly suited for a single violet laser system or a violet/red laser system where inter beam compensation can be minimized.

With acoustic washing, secondary labeling can be accomplished very quickly and easily by primary labeling, acoustic washing, secondary labeling and a second acoustic wash. An automated system or semi automated system to do this will reduce not only assaying time but operator error.

Secondary long-lifetime labels are particularly suited to a long transit time cytometer with modulated or pulsed excitation as they allow adding the lifetime parameter for analysis using commonly available antibodies/ligands.

Other Long Lifetime Methods

For bio/chemi/electro luminescence one can use a pulsed/modulated system that analyzes the level of luminescence in between pulses and subtracted this from the fluorescence for short-lived labels. This luminescence might be measured using reagents internal to the cell or can be membrane bound enzyme labels that interact with substrate added to the sample. Acoustic washing just prior to analysis could ensure that luminescence from the medium could be associated with the proper cell. Monitoring enzyme cleaved substrates in a more conventional manner after sorting is another possibility for drug discovery assaying but it can also be applied to low level marker assaying that require enzyme amplification for detection.

One embodiment of the present invention comprises a method for measuring chemi, bio or electro luminescence in an acoustic particle analyzer. In this method, particles capable of producing a chemi, bio or electro luminescence are moved through a channel and are acoustically focused using acoustic radiation pressure. The particles are then passed through a zone for collection of luminescence and collect light from the particle produced from chemi, bio or electroluminescence. In this embodiment, the particles are preferably focused with a radial acoustic field. Luminescence is preferably collected between excitation pulses from a light source.

Time-Resolved Fluorescence/Luminescence

Another embodiment of the present invention provides a method for circumventing background fluorescence using probes that continue to emit light for some time after the background fluorescence has substantially decayed. The advantages of slower linear particle velocity make the technique much more attractive. This method uses a modulated or pulsed laser as above but light is also collected and correlated in time to the excitation valleys where there is little or no excitation light. The longer time intervals that are not implemented in conventional flow cytometry cost much less with lower cost lasers and electronics, but their primary advantages lie in the ability of maximizing fluorophore output and to use very long lifetime probes such as lanthanide chelates and lanthanide energy transfer probes. Pulsing at the very slow (for flow cytometry) rate of a thousand times per second with a 10 microsecond pulse, would for a transit time of 10 milliseconds for example, allow 10 cycles of excitation and luminescence collection in which virtually all of the luminescence decay of a europium chelate could be monitored. This pulse rate with a conventional cytometer transit time would allow >90% of the particles to pass without ever being hit by the laser. If the pulse rate were increased to 100 kilohertz with a 1 microsecond pulse there would still be nearly 9 microseconds in which to monitor the lanthanide luminescence as most fluorophores have 1-2 nanosecond lifetimes and most autofluorescence decays within 10 nanoseconds. For some lanthanides specificity can further be increased by monitoring fluorescence of different emission peaks.

The most commonly used lanthanides, terbium and europium, are prime examples. For the Seradyn europium particles for example, their two primary emission peaks are at 591 and 613 nm. The ratio of these peaks (~13) is a highly definitive signature of this label. The peaks can be readily distinguished from each other as their bandwidth is so narrow (90% bandwidth for the 613 nm peak at 25 nm) an additional degree of specificity could also be achieved from tracking the kinetics of this emission as the 591 nm peak has a shorter lifetime than the 613 nm peak and the rate of change of the ratio would be extremely specific. In a preferred embodiment increasing luminescence of the label is monitored during subsaturation excitation pulses to monitor specificity. If the labels are not excited to saturation and if the dead time between the pulse is less than the fluorescence decay, each successive excitation cycle would increasingly excite more labels before the decay of other excited labels is complete. This gives an increasing trend in signal that is specific to the lifetime of the probe. With this method, it is not specifically the phase or lifetime that is being measured but the increase in the phase shifted emission. In principle, this can be done with other labels such as quantum dots but as their decay times are much shorter (10-100 ns), a much quicker pulse or modulation rate is required (.about.10-100 MHz). Careful attention must also be paid to the excitation intensity and formation of triplet states such that the specificity advantage is not lost by collection of fewer photons.

One of the primary sources of unwanted signals in flow cytometry and label based techniques in general is the specific fluorescence of unbound or non-specifically bound labels. For flow cytometry, squeezing the sample core size to a very small dimension and optical spatial filtering alleviate the problem of unbound labels to some degree, but ultrasensitive applications often require prewashing of the analyte species from the unbound labels. This is problematic if the labels are not of extremely high affinity as they may tend to dissociate from their targets once washing disturbs the binding equilibrium or kinetics.

Field based in-line particle washing is used to solve this problem. Laminar flow washing relies on the fact that only particles affected strongly enough by the field to move across the laminar boundary will enter the clean fluid. This generally leaves most of the labels behind. According to one embodiment of the present invention, the fluidics are constructed such that substantially clean fluid reaches the collection or analysis region. Some clean fluid is discarded with the waste in order to account for diffusion across the laminar boundary and insure high purity.

Figure 10:
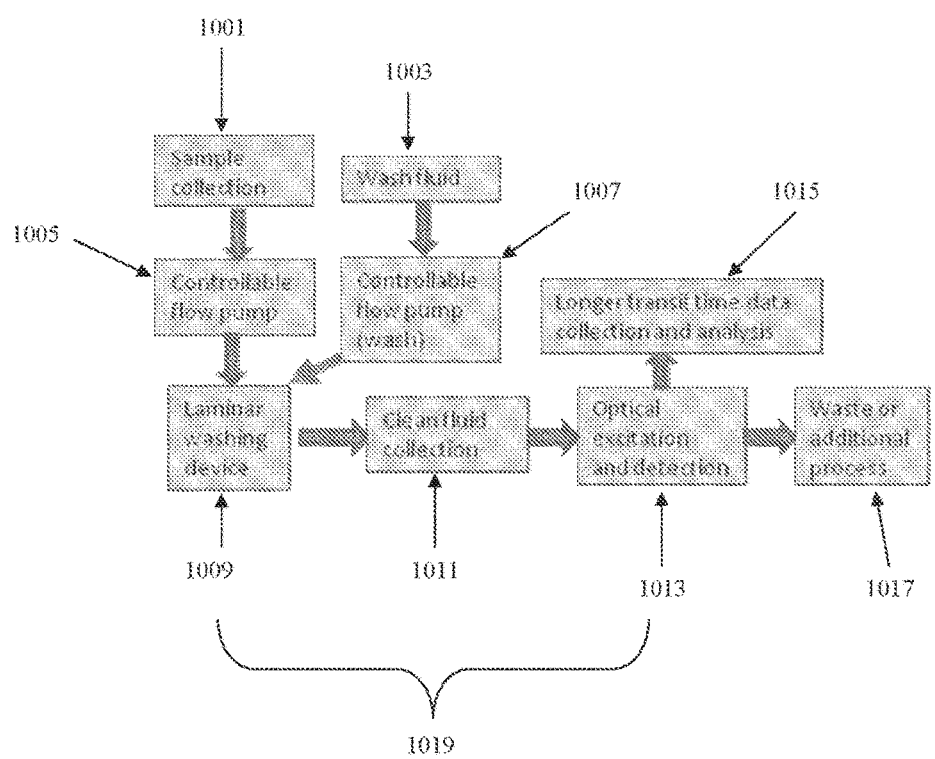
FIG. 10 illustrates the flow diagram in FIG. 9 modified to include in-line laminar washing according to one embodiment of the present invention.

Using in-line field based washing allows for very small time intervals between the alteration of binding kinetics and the analysis. By placing the wash step very close to the analysis point, washing can be achieved readily in fractions of a second. Even for relatively low affinity binding reactions, background reduced analysis can be done before significant dissociation occurs. This capability is of high importance for many applications where sensitivity is important, but binding affinity is relatively low. Many monoclonal antibodies, synthesized ligands and drug candidates fall into this category. FIG. 10 illustrates the flow chart in FIG. 9 modified to include in-line laminar washing. FIG. 10 comprises an additional pumping system 1007 used to introduce the wash fluid and fluidics which are modified to extract the cleaned particles after washing. Laminar wash devices can also be installed in series to increase purity or to process particles in different media, see example FIG. 8.

As illustrated in FIG. 10, an acoustic focusing device 1019 is modified with wash stream 1007 into which target particles can be focused. Washed particles can be analyzed within fractions of a second of being washed. For the planar device in FIG. 11, focusing is only in one dimension but this dimension can be stretched out over a large area to increase flow rates.

Figure 11:
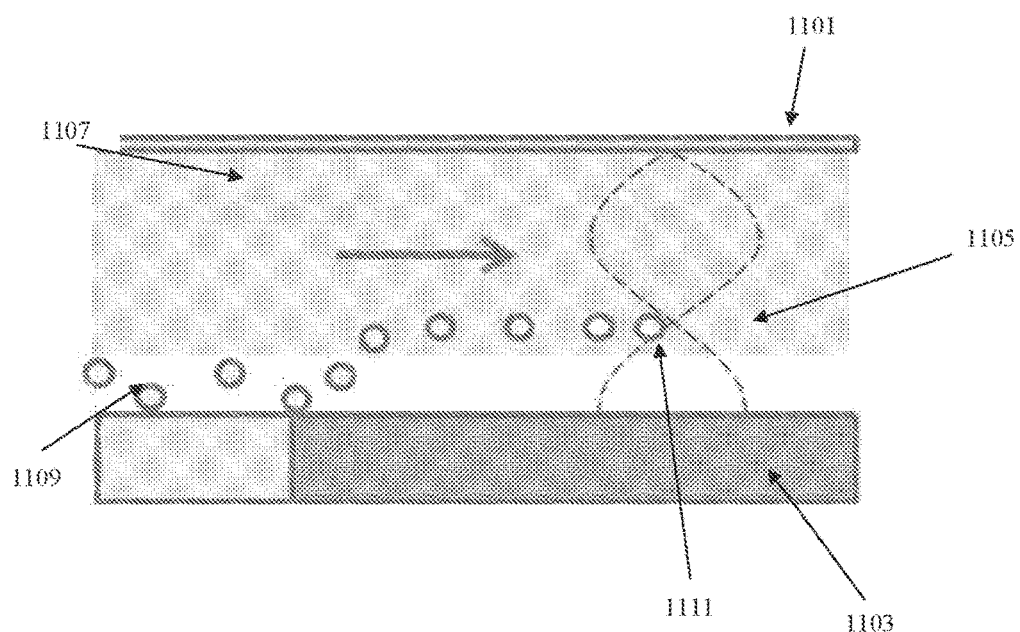
FIG. 11 illustrates field focusing of laminar wash fluid according to embodiments of the present invention.

FIG. 11 is a planar acoustic flow cell comprising laminar wash fluid 1107. Sample containing particles 1109 is introduced into flow cell 1101. An acoustic wave is introduced 1105. Particles are acoustically focused based on acoustic contrast. Channel tuning is dictated by height rather than width. This allows high width to high aspect ratio channels with higher throughput. Different standing waves can be used in accordance with FIG. 11.

Another embodiment comprises a planar acoustic flow cell wherein the acoustic node is located outside flow cell 1101. In this embodiment, particles 1109 are acoustically focused to the top of the flow cell where acoustic wave 1105 is introduced.

Multi-Color Analysis

Most of multiplexing in flow falls into two distinct categories. The first is often referred to as multicolor analysis in which several markers on or in cells are examined simultaneously in order to extract as much information as possible from the cells being analyzed. Probes of different spectral wavelengths are chosen such that there is maximal excitation overlap and minimal emission overlap and usually the markers that are known to bind the fewest labels will be given the brightest probes in hopes that all markers can be resolved. Tandem probes are useful such that one or two lasers could be used to excite many fluorophores with different emission spectra. In practice there is considerable spectral overlap between probes and a great deal of effort is expended on subtracting the signal contribution of these overlaps such that each individual probe is accurately quantified.

One embodiment of the present invention provides a system and method to produce greater signal to noise resolution of the specific signals and improved methods for isolating the different probes. First, the use of longer lifetime probes such as the narrow emission of quantum dots and of lanthanides can be better exploited to extract individual signals with less compensation. By using pulsed or modulated lasers, the fluorescence lifetime of the probes can be monitored to determine the individual contributions of different dyes. Even if there is fluorescence contributed to detection channels monitoring shorter lifetime probes, this fluorescence can be subtracted based on the quantity of time resolved fluorescence detected. In an embodiment, the increased signal generated for the longer transit times by using narrower bandwidth filters is utilized. These filters collect less light but do a better job of separating fluorescence signals from different probes. The band width can be made narrower than in conventional systems because there is more signal to spare. The narrow bandwidth approach collects the entire spectrum with a prism or grating and multi-element detectors. In this case the resolution of the spectrum dictates how much bandwidth per element is collected. Longer transit times make spectral collection much more practical.

Multiplexed Assaying

The second form of multiplexing in flow is the use of multiple bead populations to encode simultaneous assaying such that each can be distinguished from each other. Specific chemistry is placed on each population and then the populations are mixed in a single reaction vessel and are then processed in flow. The distinctive properties of each population such as size and or fluorescence color and or fluorescence intensity are then detected to distinguish the beads from each other. The assay on each bead must be distinguished from the bead's intrinsic properties and this is typically done by using a different color fluorescence for the assaying itself. These multiplexed soluble arrays may be used in diverse applications in accordance with the present invention including but not limited to immunoassaying, genetic assaying, and drug discovery assaying.

One type of soluble bead array uses two fluorescent dyes that are doped into the beads in varying concentrations to produce populations with distinct fluorescent color ratios. Between two colors and ten intensities an array of 100 distinct beads is made. It is sometimes difficult to resolve all of the beads due to variance in the beads and the detection systems. Longer transit times and the associated higher signal increase sensitivity and resolution. This means that for any color coded multiplex system more intensity levels can be resolved and lower concentrations of dyes or other labels need be used. Quantum dots are excellent for creation of soluble arrays owing to their narrow spectral emission and their ability to all be excited by a single laser. According to one embodiment of the present invention a system and method provides for longer transit times of particles having quantum dots. Beads may be made with much fewer quantum dots. This makes them less expensive with a lower background interference for assaying. It also makes for more resolvable intensity levels such that greater numbers of distinct beads can be made. A set using 4 colors of Q-dots and 5 intensities for example yields a set of 625 distinct beads. The same 4 colors and 10 intensities yields a set of 10,000.

A difficult problem in multiplexed arrays is distinguishing the coding fluorescence from assaying fluorescence. This is a particular problem when high sensitivity is required from a high intensity coded microsphere. The methods detailed above for multi-color analysis can all be used to make this easier. In particular, long fluorescence lifetime probes, including but not limited to lanthanide labels with quantum dot arrays and time-resolved fluorescence, may be used. Lanthanide labels are mostly excited by ultra violet light (europium 360 nm max absorption). This allows them to be used in conjunction with quantum dots and a single excitation source (e.g. 375 nm diode laser, pulsed or modulated for life-time applications). The lanthanides' very narrow spectral emission can also be effectively used for lanthanide based microsphere arrays.

By choosing dyes with different fluorescence lifetimes, arrays can also be made based on lifetime alone. If for example both a conventional short lifetime UV excited dye and a long lifetime lanthanide dye were impregnated at discrete concentrations into bead sets, both dyes can be excited by a pulsed/modulated UV source and the rate of emission decay would be specific for each discrete concentration. Neither dye would be excited by longer wavelength lasers, particularly the blue, green and red lasers most common in cytometry. This allows for monitoring assaying across a wide range of probe colors. In addition, this lifetime decay method can be implemented with a single photodetector and a simple filter to block scattered light at the UV excitation wavelength. The lifetime method can also be combined with other multiplexing methods such as particle size and or multicolor multiplexing to increase array size.

In another embodiment of the present invention, fluorescence is separated from luminescence by collecting light as the particle travels in and out of a continuous light source. Fluorescence is collected while the particle is illuminated and luminescence just after the particle has left the illumination. This can be done with properly spaced collection optics or over the entire space using a multi-element detector such as multi-anode PMT or a charge coupled device (CCD).

In another embodiment of the present invention, coupled with imaging optics, the CCD above, or another imaging detector can also perform time resolved imaging on focused particles. This is not done in flow cytometry. In fact any imaging technique that requires longer excitation and or emission exposure than is afforded in conventional hydrodynamic focusing is possible in a field focused system.

Figures 21A, 21B:
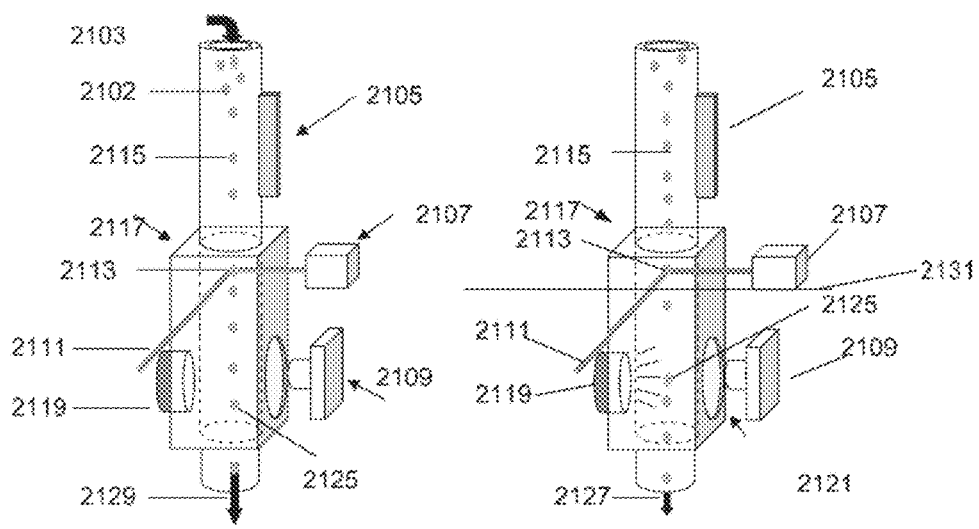
FIGS. 21A-21B illustrate a system and method for optical analysis of acoustically repositioned particles and a medium.

Referring now to FIG. 21A which illustrates an embodiment of the present invention, sample 2103 containing particles 2102 is introduced in the system. Line drive 2105 induces an acoustic wave and particles 2102 are acoustically focused based upon their acoustic contrast 2115.

Optics cell 2117 receives particles and interrogates each particle at an interrogation site where interrogation source 2111 impinges electromagnetic radiation upon particle. An optical signal 2113 from each particle and/or sample is collected by 2107.

The signal is analyzed and based upon user determined criteria and optical signal from a particle, a selected particle or group of particles is imaged by an imager 2109. The particle may receive an illuminating light from a light source 2119 for imaging. In FIG. 21A, no image is acquired and the flow rate 2129 remains unchanged.

The flow rate can be altered once a particle meeting a user defined criteria is detected at 2107. The particle at 2125 in FIG. 21B is moving slower than particle 2125 in FIG. 21A because the flow rate is decreased to acquire an image in FIG. 21B. The flow rate is decreased once a particle having the user defined criteria is detected at 2107. An image of the particle is acquired by imager 2109 and the image may be illuminated by an illumination source 2119. Once the image is acquired the flow rate remains decreased 2107. Alternatively, the flow rate is increased for improved particle throughput through the system.

Figure 22:
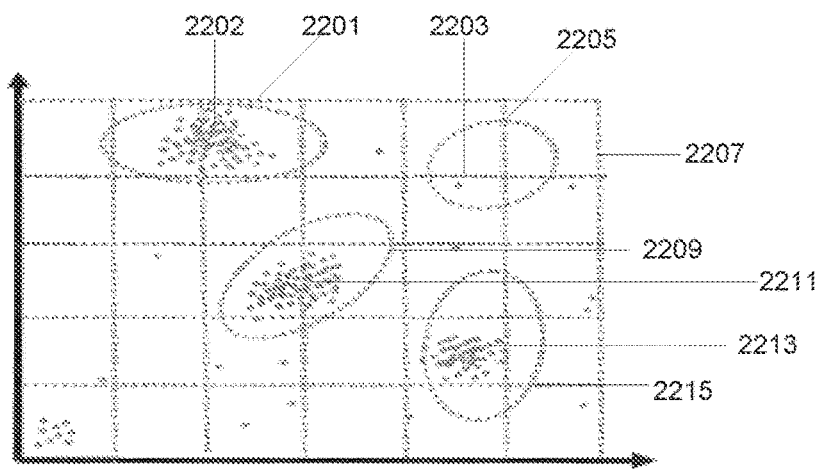
FIG. 22 illustrates a diagram of particle groupings with different parameters.

Referring now to FIG. 22, a bivariant plot of particles analyzed in a system as shown FIG. 21 is provided according to one embodiment of the present invention. Each particle within a group of particles 2202 are similar as to Parameter 1 and Parameter 2. Parameter 1 can be, for example, forward scatter, side scatter or fluorescence. Parameter 2 can be, for example, forward scatter, side scatter or fluorescence. The user defined threshold 2201 indentifies particles that meet a threshold for imaging. A particle having a value for Parameter 1 and for Parameter 2 that is greater or lesser than the threshold defined by the user triggers the imager and is imaged. If the particle meets the user defined criteria then the flow of the stream carrying the particles is reduced to a rate that allows the imager to capture an in-focus image of the particle or particles as the particle transits past the imager 2109 of FIG. 21.

Other detection thresholds 2205, 2209 and 2215 can be established for particles having similar Parameter 1 and/or Parameter 2 values.

Figure 23:
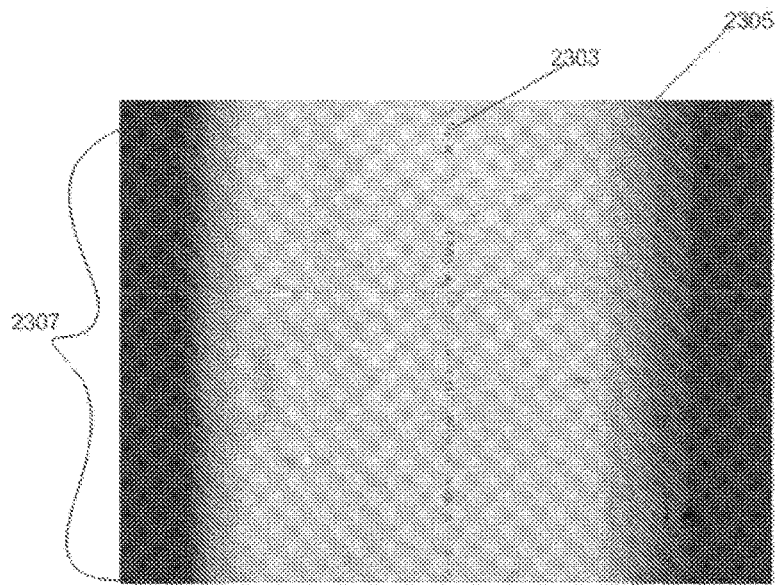
FIG. 23 illustrates an image of acoustically repositioned particles imaged by an imager.

Referring now to FIG. 23, is a photograph of blood cells 2303 are captured for a stream 2305 that is acoustically reoriented. The stream in the optics cell 2307 is slowed so the imager (not shown) can capture particles 2303 in focus. To create the image, a line-driven capillary of inner diameter 410 µm is truncated with an optical cell. The optical cell is a borosilicate glass cube with an interior circular cylindrical channel the same diameter as the inner diameter of the line-driven capillary. The frequency of excitation is approximately 2.1 MHz and the power consumption of the acoustic device is 125 milliwatts. The cells are lined up single file coincident with the axis of the capillary. In this image, flow is nearly static for imaging purposes, but our recent engineering advances in constructing line-driven capillary prototypes have proven fine focusing of 5 µm latex particles and blood cells at volumetric flow rates exceeding 5 mL/minute.

In a preferred embodiment of the present invention, a line-driven capillary is attached to a square cross-section quartz optics cell. The inner cavity of the optical cell is circular in cross section and has the same inner diameter as the line-driven capillary to extend the resonance condition of the fluid column thereby extending the acoustic focusing force into the optical cell. In operation, the particles are aligned along the axis of the capillary by the acoustic force and fluid flow transports them through the system. The particles first enter the analysis stage where an incident laser beam excites the particle and attached fluorescent markers. When a target of interest is identified by its scatter and fluorescence signature (user defined), the control system decelerates the flow velocity to a value appropriate for the required imaging resolution. A flash LED (wideband or UV) then illuminates the particle to capture the image. Once the image is captured, the system re-accelerates the flow in the original direction and analysis continues until another particle of interest is encountered.

To achieve the high analysis rates expected from a traditional flow cytometer analyzer, the embodiment will not capture an image of every particle analyzed in the system. Rather, the user will construct a sampling matrix of particles from gated subpopulations to define a set of particle images to be captured based upon their scatter and fluorescence signatures. With this hybrid approach, high particle analysis rates are achievable (in excess of 2000/s to search through large populations of cells while capturing only a representative set of high content images that are correlated with traditional flow cytometry parameters. Images will capture cellular morphology, orientation, and internal structure (e.g. position and number of nuclei) that will be available to the researcher to correlate with localized data distributions generated by the analyzer. The ability to control flow rate while maintaining particle focus along the axis of the flow stream in the acoustic system is the key component necessary for the selective particle imaging after sample analysis.

Fast coaxial flow streams are not required as with conventional hydrodynamically sheath-focused systems. This alleviates the need for differential pressure or flow based delivery systems reducing total system cost. One of the unique capabilities of acoustically driven flow cells is the ability to select the sample delivery rate. By not accelerating the particles with the coaxial sheath flow, particle transit times through the laser interrogation region of a flow cytometer are .about.20-100 times longer than conventional hydrodynamically focused systems. In comparison, higher sensitivity optical measurements can be made while retaining similar particle analysis rates. This enables the use of inexpensive optical components to lower system costs. Additionally, acoustically reoriented sample streams can be operated at slow fluid velocities or even stopped and reversed without degrading alignment of the particle stream within the flow chamber allowing rare targets to be repeatedly analyzed or even imaged.

Imaging is performed commercially in flow cytometry using imaging optic by fluid imaging. The fluid imaging uses deep focus optics without hydrodynamic focusing to take pictures of cells or particles, or even organisms as they pass through a rectangular imaging cell. The method has adjustable flow but it is limited to taking pictures of particles in focus so many are missed and magnification power and resolution is limited. One system uses hydrodynamic focusing coupled with electronic CCD panning technology that can track the flowing cells. The system is designed to keep cells or particles from being blurred. Imaging rates for this system are relatively slow (up to 300 cells/sec) but slower flow and the tracking technology allow long integration times that keep sensitivity high and allow good spatial resolution (up to 0.5 microns). Unfortunately, this technology is very expensive and is limited by the hydrodynamic focus.

Acoustic cytometry of the present invention, in which hydrodynamic focusing of target cells or particles is replaced or partly replaced by acoustic radiation pressure, adjusts the linear velocity of cells or particles transiting an interrogation laser while maintaining tight particle focus. Therefore, light from photoactive probes can be collected for much longer times than are normally possible in hydrodynamically focused cytometers without loss of precision from poor particle focus. Flow in an acoustic cytometer can even be stopped or reversed, allowing very long observation or imaging for resolution of spatial information.

One advantage that field focused systems have over hydrodynamic focused systems, is again the control of linear velocity while maintaining particle focus and high analysis rates. Greater transit times can be used all the way up to stopped flow. Pulsed flow is a viable option in field focused systems in which fluid delivery is triggered by upstream detectors such that cells or particles are stopped in the imaging region and flow is maximized when no particles are present. This method increases throughput while maximizing exposure times.

Another embodiment of the present invention provides a method to increase throughput in field focused systems with a planar focusing system such as that shown in FIG. 11. For this system, many particles can be imaged simultaneously. By using a wider field of view, some spatial resolution may be lost, but many applications do not require diffraction limited resolution. Controllable velocity can make this technique extremely sensitive and also easier to implement. Pulsed flow can also be used by taking images of particles/cells in batches: take a picture, then flush out the already imaged cells while replacing them with a new batch of cells.

The statistical power of the cytometer of the present invention and the spatial resolving power of imaging are combined when additionally imaging particles. This combination is very significant for numerous applications where cell morphology and or localization of markers are important. Fluorescence in-situ hybridization (FISH), cancer screening, intracellular and membrane protein/drug localization and co-localization are a few of the analyses that could benefit tremendously. Other applications such as industrial process monitoring or monitoring of environmental samples can also benefit.

Another application for imaging in flow is the use of spatially barcoded particles for multiplexed assaying. The microfluid method ensures that the particles align properly by using very small channel dimensions. The acoustic focusing preferentially orients such particles in the field making it possible to use much larger channels that are not prone to clogging.

Methods for Monitoring Cell/Particle Kinetics in Field Focused Particle/Cell Analysis Systems Another embodiment of the present invention provides for cell monitoring or particle reaction kinetics by the imaging methods above but these kinetics can also be monitored without imaging in field focused systems with long transit times. The transit times can be adjusted to monitor whatever process is of interest. The method lends itself very well to techniques that use light activated species such as caged fluorophores or ions, photoactivated GFP or photoactivated ATP or GTP. Such techniques are absent in flow cytometry due to the need for longer analysis times.

Kinetics Quantification

The quantification of kinetic parameters such as antibody binding constants and enzyme substrate cleavage rates can be quantified using in-line acoustic washing and analysis. By placing reactant of a known concentration in a laminar stream and acoustically transferring the reactive particles into the stream such that the time of exposure to each other is known, one can determine kinetic parameters using data collected from the beads in a cytometer. For example, a new antibody can be tested by switching antigen coated beads stained with fluorescent antibody with known constants into a stream containing a known concentration of the new antibody. The fluorescence of the beads relative to controls indicate the new antibody's ability to displace the known antibody. The time of interaction can be varied with flow rate. If the constants to be measured are longer lived, starting the reaction by prediluting with reagent and measuring fluorescence over the course of analyzing the whole sample is another alternative.

Microsphere beads are used for a myriad of applications in sample preparation and purification. Among the most common are nucleic acid separation, protein fractionation and affinity purification, cell isolation and cell expansion. Beads are generally separated from sample media by centrifugation or magnetic means. The microsphere beads can also be separated by acoustic means and are typically denser and less compressible than most biological materials. For these beads, acoustic washing with a fluid stream of high enough acoustic contrast to largely exclude sample materials while allowing central focus of the beads allows execution of protocols otherwise employing magnetic means and centrifugation. For many protocols, this allows cheaper non-magnetic beads to be used. It also provides for automation of steps that are typically carried out in sample tubes.

Magnetic and acoustic forces can also be used in tandem, allowing ternary separations of magnetic and acoustic beads or magnetically and acoustically labeled cells. Of course, magnetic beads can be used in a conventional manner and then be further processed or analyzed using acoustic sample prep and or an acoustic cytometer. This combination can be quite powerful as magnetic forces generally excel at quickly and conveniently separating targets from concentrated samples while acoustic cytometry excels at quickly processing dilute samples. Multiplexed magnetic bead arrays are a prime example of this where the convenience of tube preparation is combined with the power of acoustic cytometry analysis.

Example: Negative Contrast Particles Nucleic Acid Isolation

Negative contrast particles modified for nucleic acid capture are incubated with a lysed sample and flowed through the acoustic separator where they are forced to the outside walls. They are then washed with the acoustic field on and resuspended with the field off. Washing in this way can be repeated as many times as is desired. If the particles are of low enough acoustic contrast, they can also be washed with isopropanol and ethanol as required. Nucleic acid elution can be performed with the appropriate buffer and particles can be removed by simply turning on the acoustic field. Alternatively, further reagents can be added for nucleic acid amplification directly in the chamber, as the required thermal control if implemented.

Example: Microbe Isolation from Blood

The low level of microbes found in blood during sepsis poses many challenges to sample prep for concentration and isolation of the pathogen. Acoustic washing can be implemented in ways that solve many of these challenges. By flowing clean media down the center and flowing contaminated sample around the clean central core, smaller microbes can be effectively excluded from collection in the central core. The central collector removes blood cells and the outer collector, which at this point contains mostly platelets and the contaminating microbes, proceeds to a second separation in which a core dense enough to exclude platelets but not most microbes is used to collect and concentrate microbes. The collected sample can then be concentrated further or be sent to analysis and/or be cultured.

Electroporation

The possibility of washing cells into a medium for lysis or permeating membranes is possible using acoustic washing. This idea can also be applied to electroporation whereby cells are acoustically focused into a reagent loaded stream and are flowed through an electric field that permeates the cell membrane and allows reagent entry into the cell. The field can also be used for other reactions like electroluminescence.

The single line focusing possible in a line-driven system allows precise control of the field parameters that each individual cell is exposed to. It also enables post electroporation analysis and sorting. For example, a host of different cell types can be processed and then sorted on the basis of cell surface markers and cultured and or analyzed for the effect as single populations. Electroporation can also be performed without acoustic washing but may be preferable for conservation of reagents or limiting cell exposure to reagents.

High Resolution Continuous Field Flow Fractionation Using Pre-Focusing

Figure 25:
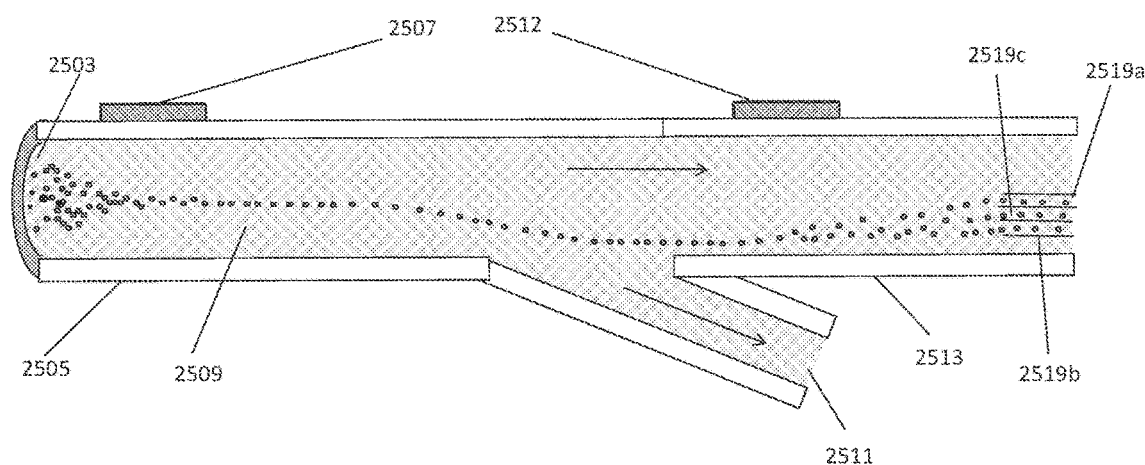
FIG. 25 illustrates a first acoustic focuser focusing particles in a tight, single file line and then a second acoustic focuser separating particles based on size.

According to one embodiment of the present invention acoustic fields are used to separate particles based upon one or more characteristics of the particles such as size, acoustic properties or a combination of both. The uniformity of separation conditions with respect to each particle contributes to the precision of the separation efficiency. The ability to separate into discrete populations becomes compromised if a particle flows more slowly than another or if the particle is exposed to a different gradient field than another. Referring now to FIG. 25, focusing particles in acoustic capillaries to form a single file line is illustrated. The method can be used to provide uniform distance and acoustic field exposure during a particle separation by first passing particles in a sample into channel 2503. Particles within the sample are moved to first acoustic focuser 2505 which focuses them in single file line 2509 with first transducer 2507. An initial concentration can be adjusted to minimize aggregate formation in the acoustic field and insure minimal particle to particle interaction. The line of particles can subsequently be fed into acoustic separator 2513 equipped with transducer 2512 and multiple exit bins 2519*a*, 2519*b*, 2519*c* for separation and collection. The position of line of particles 2509 can be adjusted as it enters the separator portion of acoustic separator 2513 by drawing fluid away or otherwise removing fluid through, for example side channel 2511. Both flow rate and power can be adjusted to accomplish the desired separation. If several fractions are desired, the collector portion of the channel can be constructed in layers or bins to extract different fluid lamina. This layered construction can also aid in automated operation of the separations by reducing the need to adjust for parameters that might affect separations such as viscosity. If, for example, the viscosity changes in a particular separation due to for example, temperature change, a particular desired fraction might end up in a different bin than expected, but it can then simply be collected from that bin. Particles according to this embodiment can have a coefficient of variation improved by >40% or even >80%.

The system and method of the present invention holds particular utility for separation of microspheres that tend to be more poly-disperse as their manufactured size increases beyond about 3 microns. It is not uncommon for even relatively uniform size standards to have coefficients of variation above 10%. This corresponds to a standard deviation of 0.6 microns for a 6.0 micron particle. Resolution of the separation of populations within this variation can be very fine when the particles are well separated such that they do not interact with each other. Given that each particle has similar density and compressibility, the acoustic radiation force is proportional to the volume of the particle. Therefore, the force on a 6.2 micron particle is about 10% greater than on a 6.0 micron particle while the drag force is only about 3.2% greater. This means that in a uniform acoustic field, if the 6.0 micron particle is forced by the acoustic field to move 1 mm in a fluid, the 6.2 micron particle will move about 1.08 mm. This is more than enough movement to separate these particles into different bins. If by using this process standard deviation for collected fractions in the above example is reduced to 0.3 microns this represents a 50% improvement. Reducing it to 0.1 microns represents about an 83% improvement.

FURTHER EXAMPLES

The invention is further illustrated by the following non-limiting examples.

Probes that Particularly Benefit from Longer Transit Time

Probes useful in accordance with the present invention and that are uniquely enabled by the present invention, include but are not limited to the following:

Dimmer Labels

Extinction coefficient less than 25,000 cm$^{-1}$ M$^{-1}$ e.g. Alexa 405 and 430 and or quantum efficiency less than 25% including but not limited to ruthenium, and Cy3.

Photobleach Susceptible or Triplet State Prone Dyes.

Lower Laser Power

Dyes that suffer from photobleaching including but not limited to blue fluorescent protein or triplet state quenching including but not limited to PerCP from medium power laser spots (>10,000 W/cm$^2$).

For ultra-high power laser (>50,000 W/cm$^2$, as often used in stream in air sorters). This utility expands to include most dyes including Phycoerythrin and fluorescein.

Longer Lifetime (Continuous Wave Excitation)

Lifetimes greater than 10 nanoseconds including Q-dots, Q-dot tandems, lanthanides, lanthanide tandem dyes, transition metal ligand complexes and phosphor particles. The longer transit time allows more cycles of excitation and emission, resulting in more overall photons emitted.

Longer Lifetime (Pulsed or Modulated Excitation)

The same class of probes as for longer lifetime CW excitation benefit but there is particular utility for luminescent probes including but not limited to lanthanides/lanthanide tandems and phosphors that have lifetimes in excess of the transit time in conventional cytometry (>10 microseconds).

Bioluminescent, Chemiluminescent

Any probe that produces light from a chemical process (including photoactivated processes) that takes longer to emit the majority of photons in a conventional cytometry transit time (>10 microseconds) including but not limited to luciferin/luciferase, Ca$^{+2}$/acquorin.

Radioactive Probes/Scintillation

For extremely slow transit >100 milliseconds per particle. These types of particles are not analyzed in cytometry (even slow flow) due to the long integration times necessary to gather enough photons.

Probes Resistant to Photobleaching with High Laser Power

Using very high laser power (>50,000/cm.sup.2) combined with photobleaching resistant probes including but not limited to dye loaded nanospheres, Q-Dots® or C-Dots® and very tight spatial filtering (as in confocal microscopy) high signal to noise ratio can be achieved. Long transit times of greater than 10 microseconds combined with a very tight acoustically focused "core diameter", the spatial filtering achieves superior signal to noise.

Dimmer Labels

Dimmer labels, i.e. those having low extinction coefficients and or low quantum yields will yield more photons with longer excitation times. Some dyes may have particular utility in certain applications including but not limited to UV excited dyes for multi-color analysis including but not limited to Alexa 405 and 430 or relatively dim long Stokes shift dyes including but not limited to APC-C7. Other dyes may offer more opportunity for developing assaying that normally use brighter labels including but not limited to using dimmer tandem dyes vs. phycoerythrin tandem dyes.

Also included in the category of dimmer labels are naturally occurring fluorescent species including but not limited to NAD(P)H. Some applications for monitoring of such low quantum yield species and slower transit time systems can make this easier with higher sensitivity and more importantly, greater fluorescence resolution between cells or particles.

Less Photostable Dyes

Lower laser power and longer transit time can increase the overall output such that dyes, including but not limited to fluorescent protein or BFP could become more useful in flow.

Probes Prone to Non-Radiative State Excitation

Fluorophores as diverse as Rhodamine Atto532 and green fluorescent protein or GFP can give off many more fluorescent photons before destruction when allowed to relax from long lived triplet states following intense laser pulses. There is greater emission for pulses with longer dead time corresponding to the dark time estimated for triplet states (.about.1 microsecond). This emission is also significantly greater than for the equivalent power of continuous wave excitation. In conventional flow, one could not use a system with such long dead times between pulses, particularly for probes requiring longer relaxation times such as PerCP (~7 microsecond triplet state lifetime). The present invention allows for these longer relaxation times.

Quantum Dots

With quantum dots, their long fluorescence lifetimes reduce the amount of light they can give off when their excitation time is limited. In a longer transit, field focused system however, as in the present invention this limitation does not exist. The long transit times can elicit very bright signals even from just a few Q dots. Another problem with Q dots is that they are made using toxic materials creating large volumes of potentially hazardous waste. With the present invention, fewer Q dots can be utilized and waste volumes in field focused systems are typically ~100-1000 times smaller.

Luminescent Probes

In general, any long lifetime probe will not emit photons as quickly as a shorter lifetime probe so the performance of nearly all such probes can be tremendously improved with longer transit times as more photons per label can be emitted. Also, lanthanides can be loaded at very high concentrations in nanoparticles due to the fact that they do not self-quench easily. This allows particle tags to be much brighter than tags in solution.

Lanthanides have fluorescent lifetimes on the order of microseconds to milliseconds with the most common europium chelates having a lifetime around 0.7 milliseconds. Such probes are used for extremely sensitive assaying in which background fluorescence is gated out in time from the luminescent signal by pulsing the light source and waiting to collect light the background fluorescence has decayed. This type of luminescent assaying are useful in the field focused, long transit time system of the present invention. Tandem lanthanide fluorophores or assaying that use lanthanide based energy transfer to conventional fluorophores such as the europium/allophycocyanin based TRACE™ system (Perkin-Elmer, Waltham, Mass.) and the terbium based Lanthascreen™ (Invitrogen, Carlsbad, Calif.) can also be implemented effectively in the present invention. The lifetimes are shorter when energy transfer to the other fluorophore is possible. The lifetimes are much too long to be practical in conventional flow cytometry.

Medium switching can be applied to luminescent reactions for which exposure to luminescence reagents is controlled in time. In addition, serial or parallel reactions designed for permeation or lysis of membranes in order to facilitate diffusion of chemi or bioluminescent species can be implemented with precise timing and nearly equivalent exposure of cells to reagents. For example, cells expressing luciferase can be transferred into a medium containing both lysing/permeation reagent and luciferin. As the membrane becomes permeable to the luciferin substrate the cell will begin luminescing.

This process can of course be extended to other procedures using cell permeation such as gene transfection or cell loading of other membrane impermeant molecules/constructs. This in-line permeation can be carefully controlled with regards to time exposure of cells to lysis reagents by transferring cells in and out of the reagents sequentially.

Absorptive Dyes/Axial Light/Less Absorptive Probes

Non-fluorescent absorptive dyes are used very commonly in microscopy but not in flow cytometry due to small signal to background. With increased transit time, integration is possible such that the signal to noise can be greatly increased. Additionally, advances in high speed linear array detectors make it possible to increase signal by spatial isolation of the axial (approximately 0 degrees relative to the excitation source) light loss. Such arrays can scan fast enough to suit a slow transit time system and can give information regarding not only axial light loss but several angles of light scatter.

With a slower transit time system, bead arrays using different color and concentration of absorptive dyes can be made practical for multiplex assaying. For multiplexing with more than one color, two lasers of different color are required such that differential color absorption can be observed. If the lasers are collocated, the detectors need to be made color sensitive unless the excitation is separated in time. One advantage of such arrays is that the absorptive dyes do not interfere significantly with fluorescence tagging. Alternatively, one laser can be used if absorption is combined with another parameter such as fluorescence. Still another embodiment uses absorptive dyes with a wide band excitation source such as an LED and at least two color sensitive detectors.

With much slower linear velocities (cells can even be stopped momentarily) imaging in flow for Pap smears becomes much easier such that both morphology and the information from absorptive dyes can be collected on a field focused system.

Radioactive Tracers

Radioactive labels are useful in the present invention due to the need for long exposure times. The exposure required is on the order of seconds. In particular, pharmaceutical screening assaying that use small molecule species or other species where a fluorescent tag might interfere with the specific action of the pharmaceutical candidate being tested can benefit from the present invention.

Bioluminescent and Chemiluminescent Probes

These probes can be extremely sensitive as their signal is created without background producing excitation light. The signal from such probes is integrated over times periods from 10 microseconds to 10 seconds or more, much longer than conventional flow transit times.

Raman Scattering Probes

The field-focused systems of the present invention allow signal integration and averaging of noise such that detection of Raman signals is possible.

Example 2

Acoustic washing of the sample can eliminate most or nearly all centrifugation steps in flow assaying (or other types of assaying that would benefit from sample washing prior to analysis). This not only saves tremendous amounts of technician time, but it also automates a tedious process that is prone to operator error particularly due to fatigue. It also reduces exposure of operator to potentially bio-hazardous materials.

Adjustable Concentrator/Washer

Acoustic concentration and washing can replace centrifugation operations for many assaying methods. It has many advantages including extremely clean and gentle separation and reduced operator variation. In addition it presents new opportunities for sample processing that cannot be achieved in conventional centrifugation. By adjusting the concentration ratios used in an acoustic washer, one can chose the output concentration of a sample. If for example, the sample's initial concentration is 105 particles per milliliter and the operator desires a final concentration of 106 particles per milliliter, the operator can select flow rates for the sample and collection channels that achieve a 10 fold concentration. This process can be automated such that the user need only enter a concentration factor. It can be further automated by adding a spectrometer on or off-line from the separator that determines initial sample concentration based on light scatter and calculates the necessary flow rates to achieve a concentration given by the operator. If a sample is too dilute for the separator to accomplish the desired concentration, it can also perform several concentrations in series. If for example the starting concentration is 103 particles per milliliter, the 10 fold concentration can be performed 3 times to achieve the desired concentration.

Immunophenotyping Wash

Depending on the protocol used, sample prep may include just one separation with one device or it might include a series of steps to automate a more complex protocol. FIG. 8 is a schematic of one embodiment of the present invention. In an automated system, cells and labels are added together and incubated initially. Then various steps including washing, lysis, fixation and concentration can all be accomplished using acoustic modules without centrifugation. For example, a first step includes the transfer of blood cells from serum to eliminate serum proteins and the wash medium can contain red cell lysing reagents. The next step includes transferring the remaining cells into a quench medium to stop lysis. This medium could contain staining antibodies or the cells could be concentrated into an incubation chamber where antibodies are added. After incubation cells would then be sent to analysis where they are washed in-line to eliminate background from unbound antibodies.

It is possible to add additional processes and or washing modules in order to automate further steps, e.g. adding more reagents, and/or provide for extra washes if necessary. The acoustic cytometer is coupled to the detector and can also be fitted with an in-line medium switcher if desired.

Figure 12:
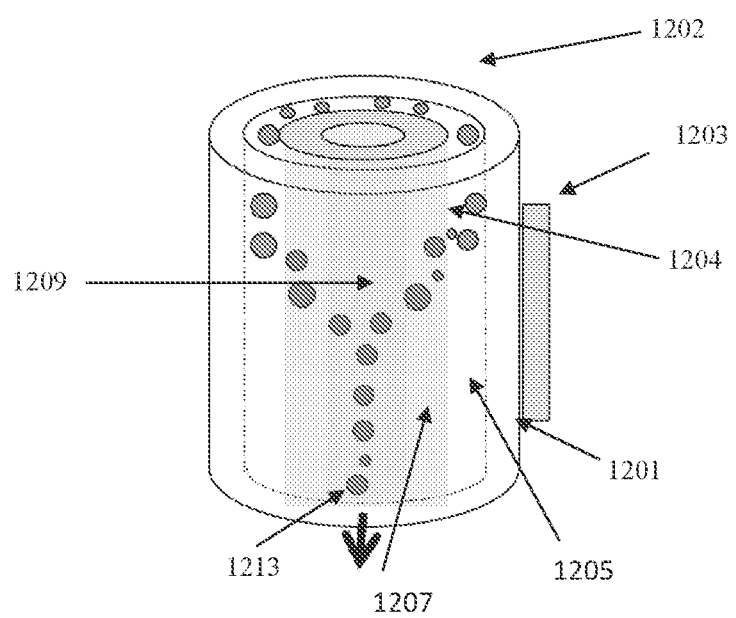
FIG. 12 illustrates a schematic of parallel fluid switching device according to one embodiment of the present invention.

While FIG. 8 illustrates a serial process using more than one separator, it is also possible to do "parallel" media changes in which more than one wash or reaction medium is flowed into a single separator and particles or cells pass sequentially through the media lamina as they move toward the center (FIG. 12). This concept can be extended to include a continuous gradient type of fractionation in which several fluids of incremental contrast are simultaneously injected into the separator. One can envision several complex protocols automated by adding more and more serial or parallel media changes or combinations thereof.

FIG. 12 illustrates a schematic of parallel medium switching device. Multiple media can be used in laminar layers. Sample 1205 is added to capillary 1201. Sample 1205 contains a first particle 1204 and a second particle 1202. A second medium is added to capillary 1201. A third medium 1209 is added to capillary 1201. A line drive 1203 induces acoustic wave and first fluid, second fluid, third fluid, first particle and second particle are acoustically focused/reoriented based upon the acoustic contrast of each. Acoustically focused particles flow out of the capillary 1213. The third fluid is preferably introduced into a channel, the third fluid having a third acoustic contrast relative to the first fluid and the second fluid. The third fluid may contain particles, and the third fluid preferably moves in a third laminar flow stream. The third fluid can have an acoustic contrast that is greater than, lesser than, or the same as the acoustic contrast of the second fluid. The third stream can also be acoustically reoriented based upon the acoustic contrast of the third fluid. A portion of particles that may be in the first fluid can be acoustically focused from the first fluid to the third fluid. This portion of particles preferably passes through the second fluid, wherein the second fluid is preferably a reagent stream. A portion of particles may also be acoustically focused from the second fluid to the third fluid.

Immunophenotyping Panels

In clinical immunophenotyping laboratories, assaying is often done on a single patient's blood in order to classify a particular disorder. The amount of assaying can be reduced by increasing the number of markers that can be assayed at once. Assaying is mostly performed with no more than 4 antibodies because of overlapping spectra for fluorescent tags. Controls for compensation in which each assaying is run without one of the four antibodies greatly increase the amount of assaying that must be performed and add a huge burden in terms of technician time, reagent consumption and analysis time. Performing the current panels without need for compensation promises to greatly streamline the process and performing larger compensation free panels of, for example 6 or more antibodies at once, can reduce assaying significantly.

Compensation is simpler for assaying with fewer colors but they can also benefit from a compensation free panel of antibodies. A very common example is a panel of anti-CD45, CD4, and CD8 antibodies which is used for CD4 positive enumeration of T-cells in AIDS progression monitoring. CD3 is often added or substituted in this panel to aid with identification of T-cells.

Table 1 below is an example list of assaying for four colors done for new patient classification of leukemia/lymphoma. This screen is used for diagnosis of new patients where the disease classification is not known. The four cell markers are listed on the left and the utility of assaying is listed at right. Typically analysis is done on a blue (488 nm) and red (635 nm) laser cytometer with each antibody having a different fluorochrome. A very common combination is FITC, PE, PE-Cy5® and APC. In an acoustic cytometer equipped with long lifetime analysis capabilities, one or more probes can be replaced with a long lifetime probe for which overlapping spectral signal can be subtracted based on temporal measurements. Long transit time can also be used to make up for lost photons if fluorescence filters are narrowed to prevent overlapping spectra. In a system equipped with a violet laser and a blue channel that is not otherwise used to detect a short-lifetime probe, auto-compensation for autofluorescence can be done on a cell by cell basis.

TABLE 1

| | |
|---|---|
| CD3<br>CD14<br>HLADr<br>CD45 | This antibody combination is designed to give a differential. CD45 vs SSC is used to define lymphocytes, monocytes and granulocytes. CD14 further defines monocytes while CD3 gives T-cells and HLADr identifies B-cells and NK cells. In bone marrow, progenitor cells are CD4 dim HLADr+ and etythroid cells or platelets are CD45 negative. |
| CD7<br>CD13<br>CD2<br>CD19 | This combination is used for three reasons. 1) Normal T-cells express CD2 and CD7. which are often expressed at abnormal levels by malignant T-cells. NK cell malignancy is usually CD7+CD2−. 2) CD2+CD7+CD13+ cells represent aberrant co expression of the myeloid antigen, CD13, on acute T lineage lymphocytic leukemias and lymphoproliferative disorders.<br>3) Co expression of CD2 or CD7 or CD13 with CD19 defines aberrant expression of these |

TABLE 1-continued

| | |
|---|---|
| | markers on B lineage malignancy. Finally, CD19 is often co-expressed on CD13 AML-FAB/M2 with a t(8,21) translocation. |
| CD5 Lambda CD19 Kappa | This combination is designed to resolve B-lineage lymphoproliferative disorders. Clonal excess of kappa or lambda on CD19 positive cells or CD19CD5 positive cells are explicitly defined. |
| CD20 CD11c CD22 CD25 | This combination is used to further characterize B-lymphoproliferative disorders and to define the degree of maturity of acute B-lineage leukemias. In addition, hairy cell leukemia. can be classified by its unique high expression of CD11c. Aberrant expression of the T-cell marker CD25 on B-cells is diagnostic for lymphoproliferative diseases when it is expressed. |
| CD5 CD19 CD10 CD34 | This antibody combination is designed to resolve the cells within the maturation of both T and B-cell lineages. The earliest T-cells are CD5+CD10+CD34+, which differentiate into CD5+CD10+ by losing CD34 and finally into mature T-cells that express only CD5. This combination can be used to evaluate the maturity of a T lineage acute leukemia, In a like manner, the maturation of the two distinct B-cell lineages: CD19+CD5− and CD19+CD5+ can be defined. The earliest B-cells co express both CD34 and CD10. As maturation occurs, they lose CD34; then CD10 to become mature B-cells. |
| CD15 CD56 CD19 CD56 CD34 | This combination is used to define aberrant antibody expression on hematopoietic malignancies. CD56 is expressed early on progenitor cells (CD34+CD56+) that may also co-express CD15. We have shown that in acute leukemia, co-expression of CD15, CD56 and CD34 is associated with the t(8,21) translocation, which results in a very bad prognosis. CD15 is also expressed on granulocytes and some B-cells. |

Table 2 below illustrates examples of assaying six color leukemia/lymphoma cells that utilize six labels to reduce the amount of assaying that must be run. Each assaying is numbered on the left, the top column is the fluorochrome used for each antibody and the specificity of each antibody is listed left to right underneath its respective fluorochrome label. In this table there is significant spectral overlap. Again by replacing fluorochromes with a long-lifetime reagents and narrow band reagents, minimal compensation antibody panels are possible.

TABLE 2

| | FITC | PE | PerCP-CY5.5 | PE-CY7 | APC | APC-CY7 |
|---|---|---|---|---|---|---|
| 1 | CD7 | CD4 | CD2 | CD8 | CD3 | CD45 |
| 1. | Kappa | Lambda | CD5 | CD10 | CD34 | CD19 |
| 2. | CD38 | CD11c | CD22 | CD19 | CD23 | CD20 |
| 3. | CD57 | CD56 | CD33 | CD8 | CD161 | CD3 |
| 4. | CD11b | CD13 | CD33 | HLADr | CD34 | CD45 |
| 5. | CD71 | CD32 | CD41a | CD16 | CD64 | CD45 |

Table 3 below shows an example of labels that accomplish compensation minimized results that do not require compensation controls. The instrument uses 405 nm and 635 nm pulsed diode lasers.

TABLE 3

| | Qdot ®545 | Qdot ®800 | EuropiumDEADIT | PerCP | APC | Alexafluor ®405 |
|---|---|---|---|---|---|---|
| 1 | CD7 | CD4 | CD2 | CD8 | CD3 | CD45 |
| 1. | Kappa | Lambda | CD5 | CD10 | CD34 | CD19 |
| 2. | CD38 | CD11c | CD22 | CD19 | CD23 | CD20 |
| 3. | CD57 | CD56 | CD33 | CD8 | CD161 | CD3 |
| 4. | CD11b | CD13 | CD33 | hLADr | CD34 | CD45 |
| 5. | CD71 | CD32 | CD41a | CD16 | CD64 | CD45 |

Temperature

Temperature can also affect specific gravity and therefore acoustic contrast. This feature can be manipulated by pre-cooling and/or pre-heating one or more of the input streams or by heating or cooling different parts of the separator so as to create a temperature gradient in the fluid stream.

Example 3

In-Line Red Cell/Cell Lysis

By incorporating a rapid red cell lysis reagent into the central wash stream, it is possible to lyse red cells in-line in a flowing separator. After lysis, the unlysed white cells can be quickly transferred to a quenching buffer in a subsequent separator. This operation can be performed in seconds, minimizing damage or loss of white cells. The second operation can also be used to exclude debris including lysed red cell "ghosts" that have decreased acoustic contrast resulting from the lysis process.

Concentration of Analytes/White Cells to Decrease Labels or Time

Often, staining of white blood cells for immunophenotyping is done in a small volume of blood prior to lysis. Alternatively, staining can be done after lysis but the sample volume and number of white cells must be carefully controlled in order to insure the proper immune-reaction. The acoustic wash system can be used to concentrate target cells or particles to a small volume for proper immunostaining. This feature is particularly valuable for samples with a low concentration of target cells as it allows a smaller staining volume and therefore less antibody. For example, such a system can be used to decrease the cost of assaying in CD 4+T cell counting for AIDS progression monitoring. It is also valuable for removal of native serum antibodies that might interfere with proper white cell staining, particularly when coupled with acoustic washing. It is also valuable for removal of native serum antibodies that might interfere with proper white blood cell staining, particularly when coupled with acoustic washing.

Acoustic No Lysis Protocols

Immunophenotyping in blood is sometimes performed without red cell lysis by triggering detection on fluorescence signals rather than scatter signals. In these protocols, whole blood is stained with appropriate antibody and fed into a cytometer without lysis, in some cases with virtually no dilution. An acoustic cytometer according to one embodiment of the present invention is capable of performing this type of assaying with higher throughput of between approximately 100-500 µl of whole blood per minute since the blood cells can be concentrated into a central core with very little interstitial space. The white blood cells in normal patients usually make up less than 1% of the total number of cells in whole blood so coincidence of white cells in the dense blood core is rare. Hydrodynamic focusing cannot form such a solid core and can therefore not pass as many cells through a given cross sectional area. An additional advantage to formation of such a core is that all cells in the core travel at the same speed allowing for uniform transit times through a laser spot. The no lysis protocol can be further improved by adding an acoustic wash step that transfers the blood cells away from free antibody and into clean buffer. This reduces fluorescent background and increases sensitivity. In addition, the clean buffer can be adjusted to have an index of refraction that closely matches the cell's index. This has the effect of reducing scattering of the laser by the cell core.

Figures 13A, 13B:
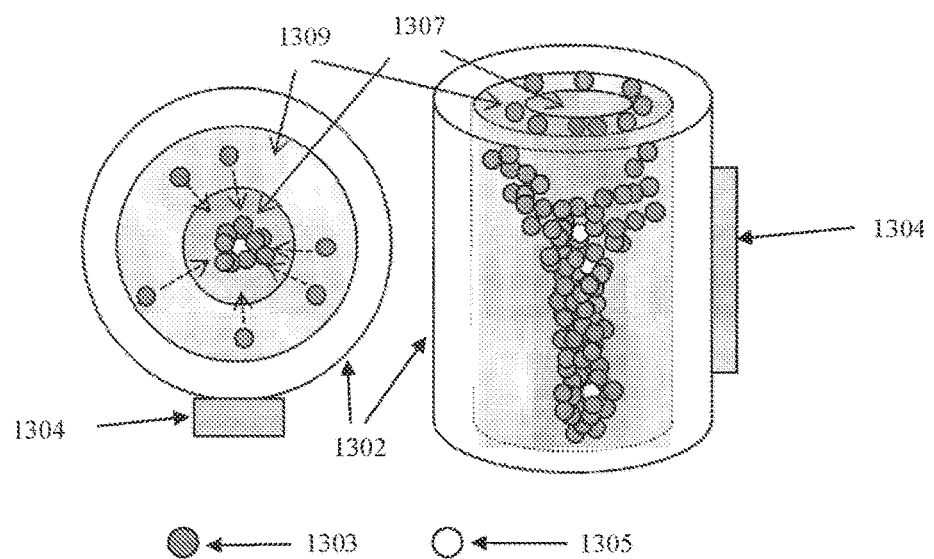
FIGS. 13A and 13B are schematics for stream switching of unlysed whole blood according to one embodiment of the present invention.

FIG. 13 is an illustration for stream switching of unlysed whole blood according to one embodiment of the present invention. Because of their relative low numbers white cells maintain separation in the rope like structure of focused blood. Capillary 1302 receives blood sample 1309 and wash buffer 1307 at different spatial locations of the capillary 1302. Red blood cell 1303 and white blood cell 1305 are acoustically focused and sample 1309 and wash buffer 1307 are acoustically reoriented upon activation of the transducer 1304 which produces an acoustic wave of a user defined mode within the capillary 1307. Cells are acoustically focused based upon their acoustic contrast.

Example 4

Urinalysis

Analysis of particles/cells in urine is a very common test used to screen and diagnose many conditions including urinary tract infections and urinary system cancers. Most commonly, particles/cells in urine are centrifuged to concentrate them and then they are examined using a microscope slide. This is time consuming, labor intensive and subject to operator error as well as error from the effects urine can have on cellular constituents.

Urine is a destructive environment for cells as it can have non-physiological osmotic pressures and pH as well as toxic metabolites. These conditions dictate a minimal post-collection delay for examination to avoid excessive degradation of cellular targets. This exposure can be minimized in an acoustic washing system by transferring the urine sample cells and particulates immediately into a cell friendly wash solution. The concentrating effect of the system is particularly well suited to urine processing where the cells and particulates tend to be of low concentration. Concentrated and washed fractions can be processed further as needed for a particular assaying. Reagents can be added, cells can be sent to culture or genetic analysis and/or an in-line analysis step can be added.

As urine density can vary widely, the wash fluid should be denser than the maximum density expected for the patient population tested (or compressibility should be adjusted accordingly). Urine sometimes contains mineral or other crystals that can be highly dense and a serial fraction that isolates these components with a very high density wash stream followed by a second, less dense wash to capture other components might be desirable in some cases.

Example 5

Coulter Volume Sensing/Electrical Measurements for Cells/Particles from Uncalibrated Solutions/Buffers By acoustically transferring cells or particles into a solution that is calibrated for conductivity, particle counting can be done in line without centrifugation or dilution. This is of particular value for dilute samples where such manipulation by centrifuge may be difficult. It also enables automated continuous monitoring of some process. Monitoring particles in municipal water supplies is a good example as particulates are a very small volume fraction and continuous water monitoring might be desirable. One can envision a continuously operational system that might trigger more analysis as particles of certain size and characteristic increase. After triggering, for example, DNA dyes for revealing if the particles might be a biological threat can be added to the washing core and the particles would be sent to cytometric analysis.

Figure 14:
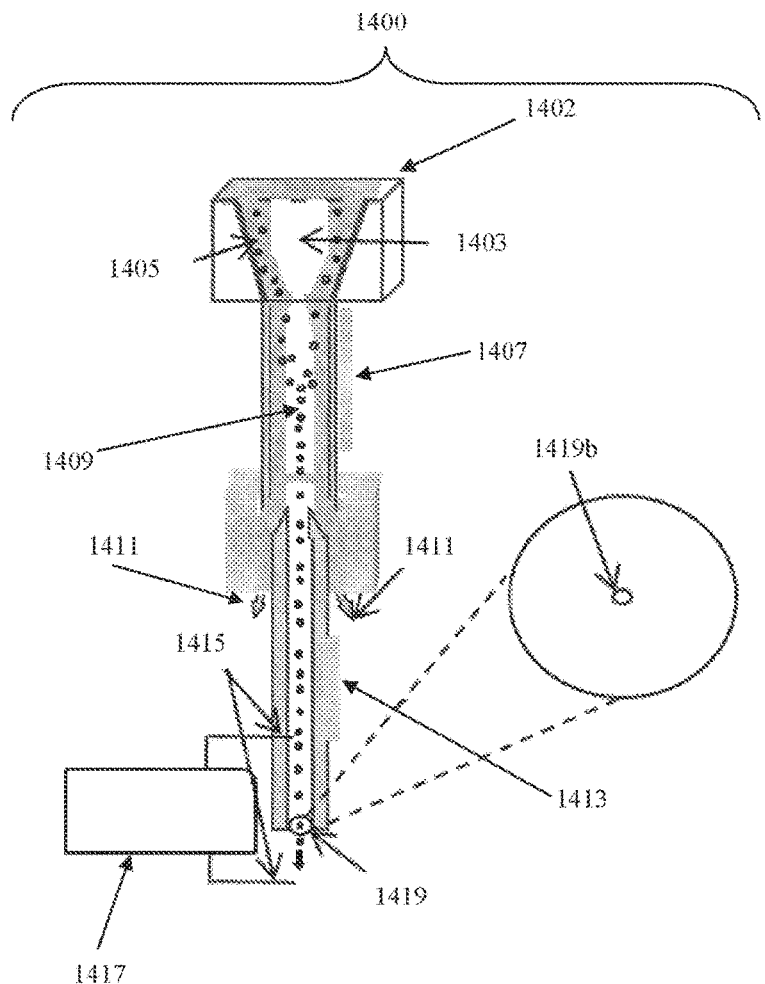
FIG. 14 is a schematic of an acoustic stream switching particle impedance analyzer according to one embodiment of the present invention.

Acoustic focusing by itself provides further advantage to pore based electrical measurements as it ensures that particles to be analyzed pass through the measuring orifice in its center (FIG. 14). This makes measurements more precise and allows for smaller particles to be analyzed in larger less clog prone pores. This way, an instrument can cover a wider range of particle sizes without changing pore size as is the common practice.

FIG. 14 is a schematic example of an acoustic stream switching particle counting device 1400. The design allows for in-line analysis of samples 1405 in unknown or unusable conductivity buffer 1403. Even without stream switching the acoustic positioning of particles 1409 improves performance over a broader range of particle sizes for a given instrument pore size 1419. Transducer 1407 provides an acoustic wave to the flow cell. Particles 1409 are acoustically focused to buffer 1403. Sample medium is discarded at 1411. Electronics detection 1417 detects signals at electrodes 1415 after particles pass from the second transducer 1413 to the detection pore 1419.

Example 6

Bead Based Reactions, Purifications and Assays

Polymer beads, including but not limited to polystyrene beads, are very useful in embodiments of the present invention. Having a somewhat similar (slightly higher) positive acoustic contrast to cells, they can be manipulated in similar fashion. Being hardier than cells however, they can be subjected to harsher environments that might damage or disrupt cells. For example, high salt environments can be used in bead based immunoassaying to reduce non-specific antibody binding. This can be done with cells as well but salinity and or exposure time must be limited if membrane integrity is required.

Beads of many different materials can be manipulated differently according to their acoustic properties. High specific gravity/low compressibility beads including but not limited to silica or ceramic beads can be acoustically focused through a high specific gravity central core that excludes the cellular debris in a lysis protocol. Negative acoustic contrast particles, e.g. silicon rubber, can be manipulated in opposite fashion such that they move to the outside wall of the capillary through a low specific gravity buffer, leaving cellular debris and uncaptured protein/nucleic acid behind in the center see (FIG. 15).

Figure 15:
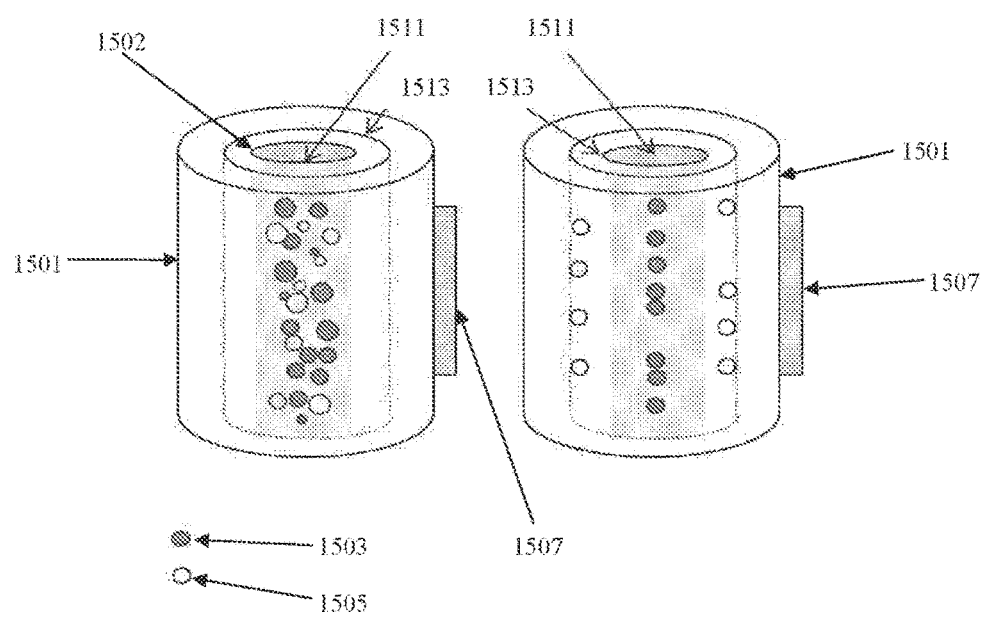
FIG. 15 is a schematic example of separation of negative contrast carrier particles from a core of blood sample according to one embodiment of the present invention.

FIG. 15 is a schematic example of separation of negative contrast carrier particles 1505 from a core of blood sample 1503 and 1511. The negative contrast carrier particles 1505 leave the core 1502 and pass through clean buffer 1503 before approaching the capillary walls 1501. A transducer 1507 induces an acoustic wave that acoustically focuses the negative contrast carrier particle to the capillary walls and focuses the blood all to the center. Other acoustic modes exist that make it possible to invert the image. Blood cells can be driven to the walls and negative contrast carrier particles to the central axis Example 7

Immunoassaying

Bead based sandwich immunoassaying benefit from acoustic wash in the same manner as immunostaining of cell surface markers. Centrifugation steps to eliminate excess antigen and reporter antibody are replaced with rapid in-line acoustic washing. The washed product is assayed in a conventional manner (e.g. bulk fluorescence, plate readers) or it is can be coupled to flow cytometry analysis, particularly if multiplexing using soluble bead arrays is desired. An apparatus useful to process samples for a plate reader provides all of the advantages of bead based assaying (inexpensive volume manufacture, better mixing and kinetics) with the existing infrastructure and easy calibration of plate reading assaying. Even enzyme linked assaying is carried out with the final amplification step being accelerated by active mixing with the beads.

Competitive immunoassaying can be performed very quickly by flowing the analyte in the center stream and pushing beads pre-bound with fluorescent antigen into the stream. As the fluorescent antigen is displaced by native antigen from the analyte medium, the change in fluorescence of both the beads and the background stream can be monitored in real time. The beads become dimmer and the background becomes brighter as the fluorescent antigen is displaced and diffuses out into the stream (see FIG. 16). As flow rate in an acoustic cytometer is adjustable, the flow rate should be adjusted to match the kinetics of the assaying such that close to maximum signal is achieved at the detection point. By moving beads into the analyte stream and acoustically concentrating them therein, these problems of diluting the analyte, limiting assaying sensitivity, and long analysis time are eliminated. In addition, individual bead detection allows multiplexing for simultaneous detection of multiple analytes. Examples of such multi-analyte testing include but are not limited to blood donor screening, and/or STD testing.

Figure 16:
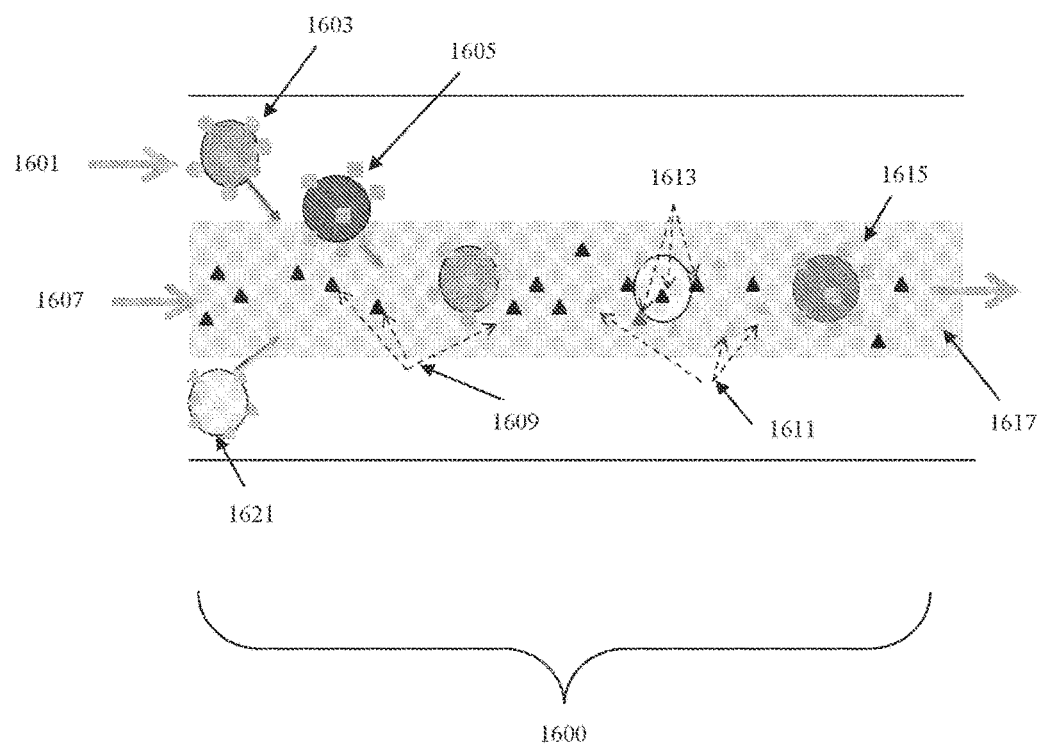
FIG. 16 illustrates a schematic example of multiplexed competitive immunoassaying in an acoustic wash system according to one embodiment of the present invention.

FIG. 16 illustrates a schematic example of multiplexed competitive immunoassaying in an acoustic wash system 1600.

Example 8

Staining of DNA/RNA Hybridized to Beads

Washing steps are eliminated for DNA/RNA prep and analysis as for protein analysis. Conventional labeling strategies using biotin or another linker are used with the final step being acoustic elimination of the reporter label prior to analysis. In addition, for native DNA or DNA without a linker, intercolating dyes are added to the wash stream in order to stain DNA hybridized to beads. Only double stranded DNA bound to beads are stained with this technique. This technique may be particularly useful for unamplified analysis of nucleic acid fragments (such as microRNA, plasmids or enzyme digested/mechanically fragmented genomic DNA).

These nucleic acids are extracted from a sample by hybridization combined with attachment of a high acoustic contrast label. The process includes hybridization of a probe with a linker including but not limited to biotin, followed by for example binding of streptavidin coated particles with high acoustic contrast including but not limited to silica, gold, or negative contrast silicone rubber. In this system, if multiplexing is desired, the probe itself may need to be coded in some readable fashion. Positive hits may only be recorded for signals that combined the coded fluorescence with signals from dyes intercolated into the hybridized nucleic acid.

Nucleic acids tests can be made more sensitive and specific if nucleic acid degrading enzymes are included in the transfer media (or a transfer medium in a previous step) and hybridized products are protected from degradation by protective modification of the DNA/RNA probes. In this way any nucleic acid not hybridized (including that non-specifically bound to beads) can be enzymatically degraded.

Example 9

New Cellular Analysis Tools/Applications

Acoustic manipulation of cells lends itself well to non-adherent cell line or cells that have been harvested from adherent culture. This combined with acoustic cell medium switching enables many new in-line manipulation techniques that enable new assaying, gentler and quicker handling of cells and lab automation.

Production of Fused Cell Lines

A critical step in the production of fused cell lines such as tumor cell/dendritic cells or B-cell hybridomas for antibody production is getting the different cell types to contact each other prior to fusion. Line driven acoustic focusing in conjunction with optimization of sample concentration can be used to line up the different types of cells in separate lines of optimal spacing. These separate lines can then be joined by flowing them both into another focuser that then joins the two lines. Electric fields can then be used to fuse the cells either in flow or not. If desired this line can then be further analyzed or sorted prior to culture.

Figure 24:
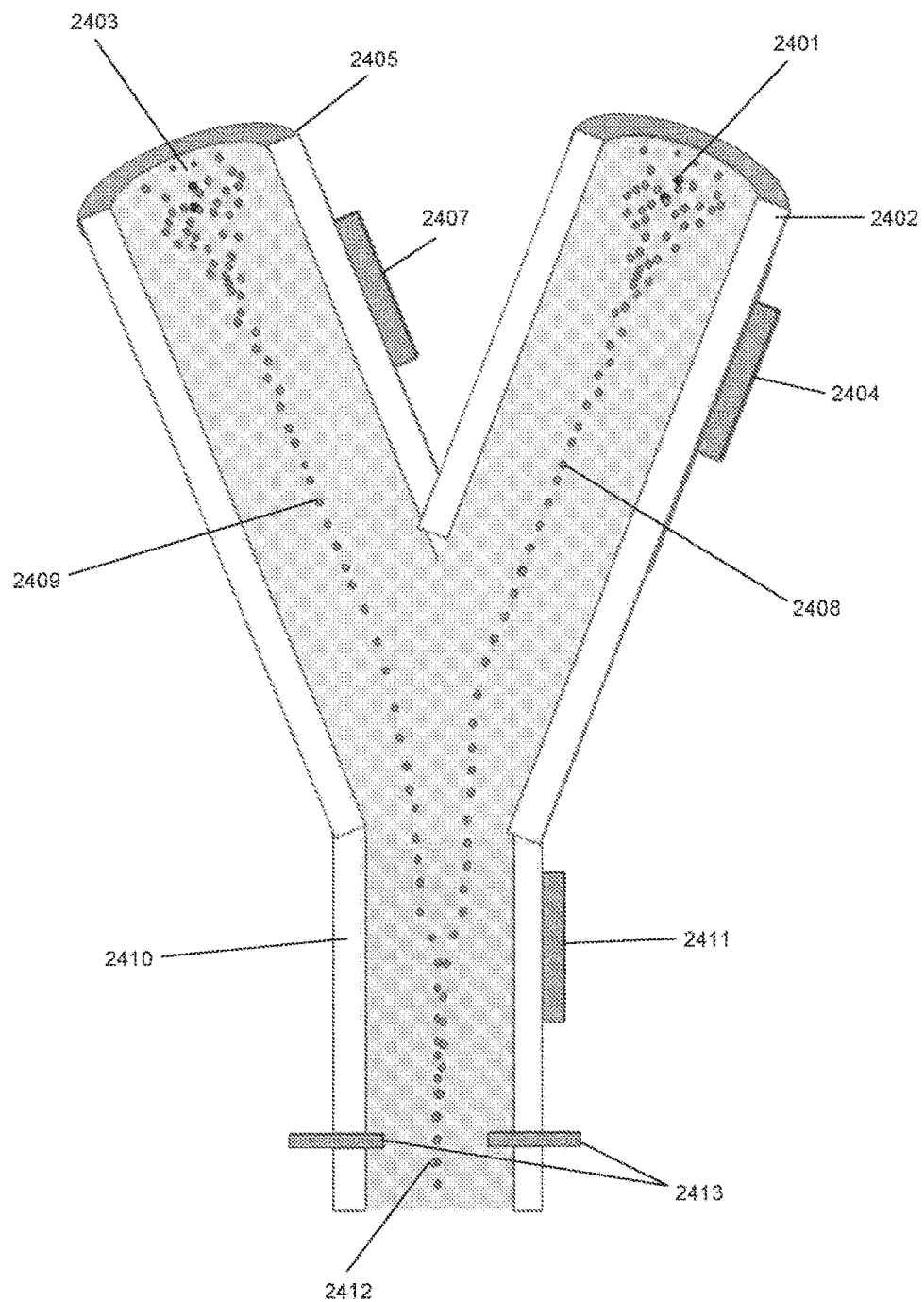
FIG. 24 illustrates acoustic positioning of particles for fusion or reaction.

Referring now to FIG. 24, acoustic positioning of particles for fusion or reaction is illustrated. First sample 2401 containing a first cell or particle type is adjusted to an optimal concentration for interaction with a second particle type. The sample is pumped through first acoustic focuser 2402 driven by a PZT transducer 2404 and the particles are acoustically focused into a line 2408 with particles having a spacing according to the sample concentration. A second sample 2403 containing a second particle type is similarly adjusted for concentration and then pumped and focused into a line 2409 in the second acoustic focuser 2405 driven by PZT transducer 2407. The flow from both samples is flowed into a third acoustic focuser 2410 driven by PZT 2411 such that each focused line of particles flows parallel to the other. When the acoustic field from the acoustic focuser 2410 is switched on, the two separate lines of particles focus to form a single line where particles from sample 1 and sample two can interact. Acoustic Bjerknes forces in acoustic focuser 2410 act to bring close particles into contact. Downstream, after particles are in contact, the pass through an electric field produced using electrodes 2413. The electric field acts to fuse cells and the fused cells 2412 may be collected for culture or sent to another process such as analysis or triggered sorting. This device is useful for production of fused cells such as antibody producing hybridoma cells and can be applied to any process requiring interaction between suspended particles.

The method is not limited to fusing cell lines but can be applied wherever close interaction of particle populations is desired. Another important example is fusing aqueous drops in oil. In this case, the carrier medium is oil and the particles are the water droplets. Each drop population can be loaded with different reagents that interact upon fusion of the droplets. The droplets can also then be analyzed or sorted in flow. Other examples include exposing cells to beads with reactants as in T-cell activating antigens or exposing macrophage or monocytes to bacteria or other particles for phagocytosis.

Another embodiment of the present invention comprises joining three or more acoustically focused streams of particles in the same fashion by flowing them all into a single acoustic focuser where they are brought into close proximity be the acoustic field.

Still another embodiment of the present invention uses two acoustic focusers. The first focuser focuses the first particle population and feeds the line of particles into the center of a second acoustic focuser. The second population of particles is then fed around the axial edges of the second focuser and is acoustically focused into the center where they join the first line of particles.

Flow Through Affinity Harvesting of Cell Products

Affinity purification of cell products such as antibodies is typically accomplished using columns. Bead based methods using centrifugation or magnetic batch separation are also available. Acoustic separation can be used to accomplish this in a flow through fashion using affinity beads. For example, specific affinity beads such as those coated with an antigen of interest or protein A or G for capture of the Fc region of antibodies would be incubated and mixed with spent medium or anti-sera to capture antibodies. The beads can then be concentrated and collected in a flow separator and washed if desired. The wash medium may be formulated to discourage non-specific binding, e.g. high salt. The collected beads are then exposed to conditions which disrupt the specific binding after which they are again collected on a flow through separator where they can be recycled for the next purification. If desired the specific binding disruption can be accomplished in flow if minimal exposure to these conditions is desired. This is done by in-line acoustic medium exchange with the dissociating medium. The dissociated product is collected independently from the beads and processed as necessary, e.g. ammonium sulfate precipitation for antibodies or other proteins.

Harvesting of Cells or Particles

When the product to be harvested are the cells themselves, an acoustic separator can be used to concentrate and collect the particles with an axial collector or if the concentration of cells is high enough it can aggregate the cells into a continuous flowing line or line of clumps that can be fed into a collection vessel where flow is slow enough to allow settling by gravity or removal by other means. This method would be particularly useful for filterless continuous collection of microalgae for biodiesel production.

Harvesting of Lysis Products from Cells or Particles

If the cell or particle must be broken or lysed to harvest the material of interest, acoustic separators may be employed to separate lysis debris from the material and may also be used in-line to initiate lysis. Microalgae lysates are a special case where the product of interest, algael oil is separated and focused to the outside of the capillary and cellular debris and residual water goes to the center. If an appropriate lysis fluid is used, a simultaneous algae collection, lysis and algae oil step can be performed in which harvested algae are fed into one stream and lysis fluid fed into the other. Debris, lysis fluid and culture medium are collected in the center and oil is collected to the outside.

Example 10

Radio Ligands/Drug Candidates

The ability to leave the original medium behind allows the combination analysis of long exposure time indicators such as radioactive ligands or drug candidates with single cell analysis and sorting techniques. For example, a radio labeled drug candidate can be added to a single well with several different cell types. Cell types incorporating positive and negative controls, including but not limited to cells from a parent line that have not been modified to contain the receptor of interest and cell lines with known activity. Relative cell size and granularity can be examined and multiple color analysis can be used to extract many parameters from each individual cell. Each cell type can be identified with cell specific fluorescent antibody combinations or with fluorescent fusion proteins/gene reporters, including stably expressing lines. A wide variety of intrinsically fluorescent reporter proteins and reporter protein systems that become stained with additional reagents may be used in the present invention. Many other reporters can be used to indicate cell conditions including but not limited to growth phase, pH, lipid related toxicity, etc. Receptor expression levels and internal fusion protein expression levels can be monitored, FRET interactions can be tracked. In short, any fluorescent parameter that can be monitored by flow cytometry can be utilized in the present invention. The multiplexed cell sample is washed in-line acoustically leaving excess radio ligands behind. The cells are then analyzed individually using acoustic flow cytometry and the analysis is sorted as to individual cell populations by fluorescence activated cell sorting (FACS). The collected population is then radioassayed for the amount of drug that remains with each population FIG. 17. If desired the cells can be acoustically transferred directly to a scintillation medium. With an acoustic flow cytometer, this process of washing, analyzing and sorting can be accomplished in fractions of a second, leaving little time for bound drug molecules to dissociate from cells. This process is particularly useful for drug candidates or other ligands that cannot be readily labeled with fluorescent or other large reporters without affecting activity.

Figure 17:
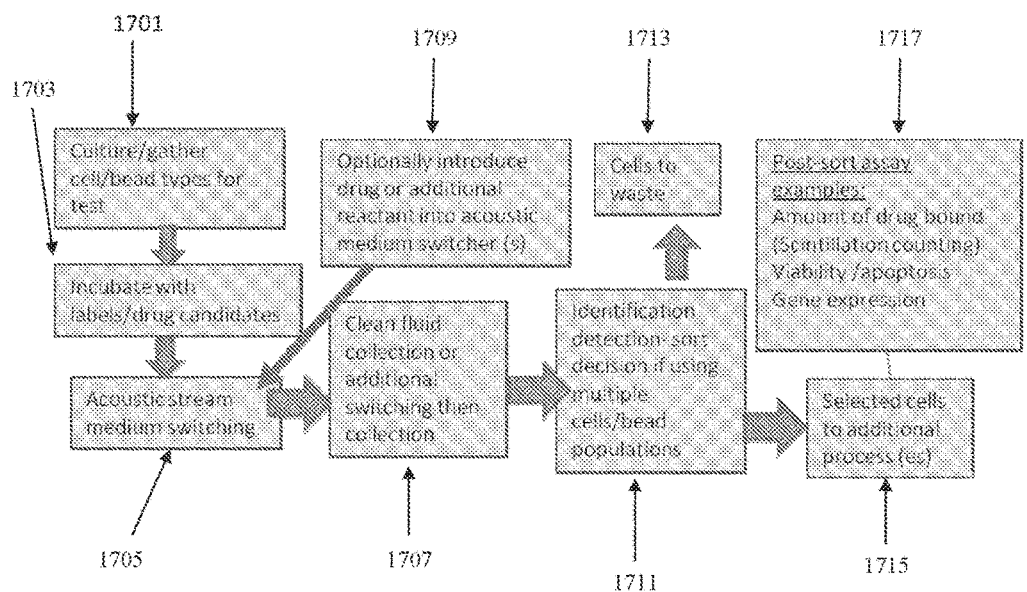
FIG. 17 illustrates a flow chart for high throughput/high content screening using acoustic fluid switching according to one embodiment of the present invention.

FIG. 17 illustrates an example flow chart for high throughput/high content screening using acoustic medium switching. Cells or particles 1701 are incubated with labels and or drug candidates of interest 1703 after which they are sent to the acoustic focuser/stream switcher 1705 where they are separated from excess drug/ligand. Optionally a different reactant 1709 can be placed in the new medium such that cells/particles interact with it during acoustic separation. Additional acoustic switch steps can be added in serial as in FIG. 8. Cells are then collected 1707 for analysis and or sorting 1711. Unwanted cells/particles can be sent to waste 1713 while selected particles are sent to additional analysis or processes 1715. Some useful examples of such processes are listed in 1717.

Of course, the acoustic washing process can be used with most any reporter and is of particular utility for any application where the concentration of ligand should be maintained up until just prior to analysis. The process can also be extended to any ligand/drug candidate that can be assayed after analysis. If, for example, a library of proteins is synthesized with a sequence that allows fluorescent staining, the staining can be done after washing and sorting to determine how much was bound to the sorted population.

If only one cell population is used, sorting is not necessary, but data collected from the single cell analysis is useful in determining virtually any other parameter that can be monitored by fluorescent acoustic cytometry, e.g. number of live/dead or apoptotic cells.

Example 11

Calcium Activation

Acoustic washing of the present invention can be used to simultaneously simplify and improve calcium activation assaying or other ion probe assaying in flow cytometry. Calcium activation studies are normally done by preloading target cells with calcium sensitive reagents, washing away excess reagent and other media components that contribute to background fluorescence, exposing the cells to a calcium activator or drug compound under test and monitoring the cells for changes in optical signal. The assaying is often done quickly after the washing step in order to keep the concentration of the reagent within the cell high. "No wash" assaying has been developed to improve precision by maintaining equilibrium between intracellular and extracellular reagents but other reagents are used to reduce background such as probenecid which inhibits active transport of the reagent outside the cell or quencher dyes which reduce the fluorescence of extracellular dyes.

With acoustic washing, reagents and fluorescent media can be rapidly removed just prior to analysis, eliminating the need for quenchers or transport inhibitors. Washing need not be done prior to adding the calcium sensitive reagent. For example, cells may be maintained in a culture medium if desired and minimizes the use of other reagents that might interfere with the activator or the cell response is minimized. The calcium activator or test compound can be added to the acoustic wash solution or it can be added just prior to the acoustic wash depending on the users desired measuring time point. The reagents for use in an acoustically washed calcium activation assaying is then simply at least one calcium sensitive reagent and an acoustic wash buffer engineered to have an acoustic contrast higher than the cell sample medium. Examples of calcium probes are the Indo series, Bis-Fura, Fura series and FuraRed™, Bis Fura, MagFura series, BTC, Calcium Green™, Calcium Orange™, Calcium Crimson™, Calcium 3™, Rhod™ series and X-Rhod™ series, Magnesium Green™ and Oregon Green™ BAPTA series. A second calcium indicator can be added to increase dynamic range measurements in a cell or a non-calcium dye can be added for reference. Combinations of dyes with reciprocal changes in fluorescence upon calcium activation have also been used to do ratiometric measurements with non-ratio-metric dyes, e.g. fluo-3 and Fura Red. Calcium indicators can be supplied in a number of different forms including cell membrane permeant AM esters and dextran conjugates designed to block internal cellular sequestration.

One embodiment of the present invention comprises a method for measuring cellular calcium concentration in an acoustic particle analyzer. This embodiment preferably introduces a calcium sensitive reagent into a population of cells to be analyzed. The population of cells is then moved through a channel wherein the population is acoustically focused in the channel. The population of cells is exposed to a reagent that may or may not induce a cellular calcium response. The population of cells is then preferably passed through an interrogation point and collecting signal to determine calcium concentration in the cell. In this embodiment, the population of cells can optionally be washed prior to analysis and/or diluted prior to analysis. The flow rate of this embodiment is preferably adjusted to achieve a desired time of analysis after the exposure to the reagent that may or may not induce a calcium response.

The power of flow cytometry to distinguish individual cells makes the prospect of engineering different cell types with the intent of simultaneously testing them for drug candidates or other activators very attractive. Each cell type can be engineered with different receptor types or receptor expression levels and can be uniquely identified using characteristic markers or other reporters. Different cell types can then be simultaneously mixed together and tested for response. Positive and negative controls can also be combined with various cell types being monitored.

The process can also be implemented in-line such that the ligand or an additional ligand(s) are serially injected into the core stream and the cells interact with the injected ligand. This is particularly useful for fast kinetic processes and can be combined with a kinetic analysis technique such as calcium sensitive fluorescence dye response. If radio labeled ligand is used, an additional in-line wash step might be required to eliminate the free ligand before sorting. Alternatively, a parallel system can be used where the cells pass through a layer of the ligand into the clean wash (see FIG. 12). In this system, interaction with the ligand will only occur as the cell passes through the ligand layer. Even if no radioligand is used, this medium switch method can be used to extract high information content as above in combination with calcium response or other kinetic analysis. The ability to adjust flow rates as desired enables tuning of each assaying to reach analysis at the desired time course. Kinetic response for a population of cells or beads can also be monitored by ramping flow rate up or down such that cells arrive at different times during the response curve.

A sensitivity problem for calcium response measurements lies in the ability to analyze quickly enough and for long enough after the calcium flux inducing ligand is added to catch and integrate the peak response of the cell population involved. The stimulant must be quickly mixed with the sample during analysis and analyzed cells end up with very different exposure times. With the acoustic media switching method of the present invention it is possible to precisely adjust flow rates such that cells arrive at analysis when desired and that they are monitored long enough to collect more signal. The method also insures that each cell in the population is exposed for the same length of time to the same concentration.

In addition to fluorescent parameters, any of these medium switch methods can also be combined with acoustic flow cytometric imaging which can provide additional valuable spatial fluorescence/luminescence information, morphology and spatially relevant absorbance information. The ability of the acoustic cytometer to drastically slow flow rates or even stop for a triggered event allows for high resolution imaging and high resolution spectroscopy, owing to the ability to integrate detection light for longer.

If cell population data is more important than individual cell data, many of the assaying protocols above can be performed in systems with simpler optics. Instead of probing single cells, a population can be monitored just after processing in a fluorescent/scintillation/luminescent plate reading device. Alternatively, reactions can be monitored inside the capillary by collecting light at either end.

Example 12

Low Affinity Drug Candidates/Ligands

Low affinity fluorescent ligands can be used in higher concentration as cells can be transferred from the high fluorescent background of excess ligand just before analysis in a time frame that does not allow significant dissociation. At high concentrations where non-specific binding of low affinity ligands may interfere with accurate analysis, acoustic washing into high salt buffers helps to favor specific reactions while accelerating non-specific dissociation.

Example 13

Multiple Ligands/Compounds and Serial/Parallel Processes

Much of biology and chemistry depends on the interaction of several different species of molecules or ligands. Acoustic medium switching provides a rapid and convenient means to expose cells or particles to a series of different compounds/ligands in rapid succession. This can be done in series and/or in parallel. It can also be readily modified to include changes in reactants or reactant concentration if the system is equipped to inject different media in the core streams or lamina of the devices.

Serial reactions can be performed for drug/ligand discovery in much the same way as shown in FIG. 11.

This can also be done in a triggered fashion in order to save resources. If for example a drug target is identified as a hit for inhibiting cell activity, it is then desirable to confirm the health and viability of the cells to exclude acute cytotoxicity of the compound. In this case, any "hits" can be diverted to a system performing viability testing. Alternatively of course, viability testing can be done simultaneously if a separately distinguishable health/viability marker is used.

Example 14

Enzyme Reactions

Enzymes are a special class of molecules that can be placed either in the original sample or in the medium that cells or particles are switched into. If cells or particles are acoustically transferred away from the enzyme, this will serve to stop an enzymatic reaction. If they are transferred into a medium containing enzyme, this will start the reaction. Enzymes are used for many protocols in sample prep, including but not limited to degradation of cell walls or unwanted nucleic acid. They are also used to detect or amplify detection of specific molecules including but not limited to fusion protein labeling or ELISA. They are also used as drug screening tools, e.g. candidates are monitored for their ability to block or inhibit the activity of specific enzymes. All of these applications are implemented in acoustic medium switching. In the last application for example, beads coated with fluorescent or FRET or quenched fluorescence enzyme substrate can be switched to a stream containing enzyme that was treated with a drug candidate. The fluorescence of the beads and the diffusing fluorescent substrate cleaved by the enzyme can be monitored much in the same way as described previously for the competitive immunoassaying (FIG. 16).

Example 15

Acoustic Medium Exchange for Bio/Chemical Synthesis, Bioreactors and Other Industrial Processes Bio/Chemical Synthesis Methods using cells or beads for sequential processes that require medium exchange can benefit greatly from the speed and automation possibilities of acoustically transferring particles across different media. Compounds synthesized on the surface of beads for example, can be transferred from medium to medium through the synthesis protocol. Another example is transfer of cells through media containing different growth factors designed to promote expression of a protein of interest in a sequential protocol.

Bioreactors

Ultrasonic concentration can be achieved, including but not limited to, antibody production using hybridomas and flocculation of microalgae for biodiesel production. The high-throughput, low-power capabilities of the round and elliptical radially concentrating systems described herein make these systems attractive for production scale bioreactor processing. The ability to perform media switching provide an additional benefit to many of these processes.

In antibody production, for example, spent antibody containing medium must be extracted from the valuable hybridoma cells, preferably without harm to the cells. Batch methods tend to produce higher concentrations of antibody but toxic metabolites generated during growth and centrifugation followed by resuspension of cells can be harmful to cells. This method also requires greater technician time and poses more contamination risks than continuous culture methods which use membranes or permeable capillary fibers for metabolite removal and nutrient replenishment One embodiment of the present invention provides for acoustic medium switching to transfer cells directly into fresh medium at optimal cell growth times. If a second incubation chamber is used to begin a new culture, cultures can be continuously grown in a hybrid batch/continuous mode in which spent media is harvested while new media is seeded at optimal cell density. Excess cells can easily be removed from confluent cultures and dead cells can be removed acoustically as their acoustic contrast is lower. A simple light scatter detector can also be incorporated into the acoustic concentration device to monitor cell growth (see FIG. 18).

Figure 18:
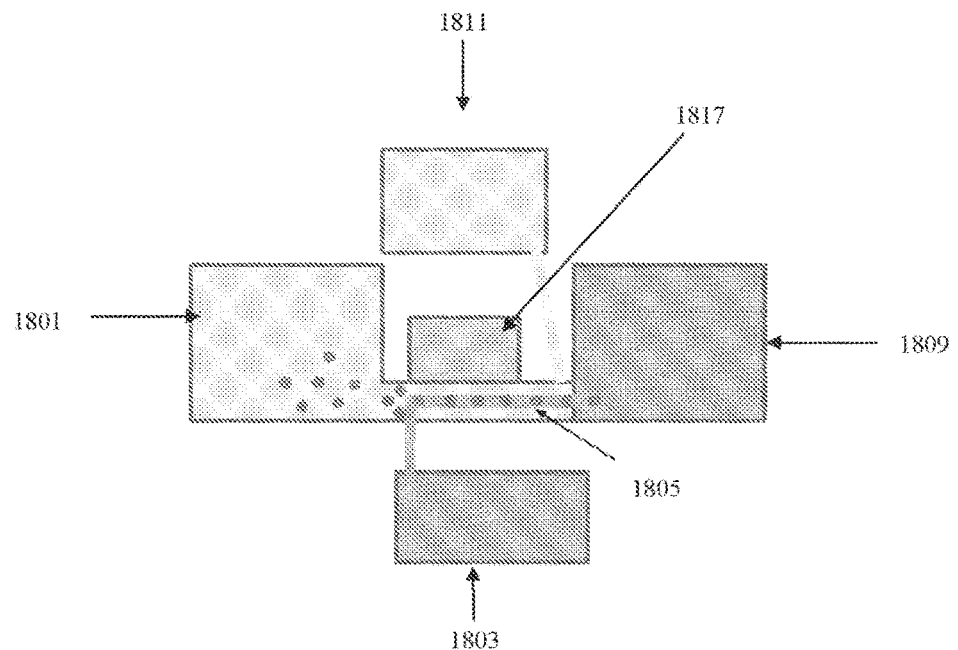
FIG. 18 illustrates a schematic example of a two chamber culturing/harvesting vessel using acoustic washing to harvest a spent medium and place cells in a fresh medium according to one embodiment of the present invention.

FIG. 18 illustrates a schematic example of a two chamber culturing/harvesting vessel using acoustic washing to harvest spent media and place cells in fresh media according to one embodiment of the present invention. The optical detector is used to non-invasively monitor cell growth at any time. Cells are cultured in chamber 1801 and periodically sent to be acoustically focused in the switching channel 1805. There they are examined for cell density/growth by the optical detector 1807. When growth and product production goals are met and the media is spent cells are sent through the channel 1805 and valves are activated to allow fresh media from the reservoir 1803 to be flowed along the axis of the channel and spent media to be harvested in a chamber 1811. The cells are focused into the fresh medium and transferred to the second culture chamber 1809 were the process can be repeated in reverse such that cells are cultured in the chamber 1809 and transferred into fresh media in the chamber 1801.

Any process requiring separation of viable cells to be recycled can be similarly implemented. Examples include but are not limited to cells, bacteria or yeast producing other secreted proteins, biofuel producing cultures such as ethanol and butanol producing yeast or bacteria. The acoustic separation process has been shown to be gentle on cultured cells and it enables automated continuously producing closed systems.

The high-throughput capabilities of round or oblate systems can also be put to good use in the harvesting of cells. For example, oil producing micro algae can be readily concentrated many fold at high flow rates with the process being readily scaled up by using multiple capillaries. The relatively large size of micro algae also permit high throughput for larger diameter, lower frequency capillaries.

Example 16

Bead Based Affinity Purifications

The utility of acoustic medium switching is not just limited to cell culture. Beads with selective coatings for the product of interest can also be envisioned in which for example the antibody is bound to protein A or G in an immunoreaction and is washed acoustically into a clean buffer where it can be removed and concentrated into the final product. This process can again be used for separation in further processes such as biotinylation or fluorescent conjugation.

The system can be further extended for use in ligand library selection (e.g. aptamer or phage selection). The process also benefits from acoustically washing into a high salt or modified pH core where bead to ligand (e.g. aptamer or phage) affinity can be controlled to select the highest affinity ligands from a library. In this system the method of multiplexed fluorescent sorting can be applied to greatly increase the number of targets tested in a library, thereby saving time and utilizing expensive libraries to their fullest (see FIG. 19).

FIG. 19 illustrates a diagram of an aptamer selection from a library. FIG. 19A illustrates multiplexed beads or cells 1903 with target molecules 1905 incubated with aptamer library 1901. FIG. 19B illustrates in-line acoustic medium switching used to separate beads/cells 1903 from unbound aptamers 1904. Flow is into the page. Salt and or pH of the wash core (center circle) can be adjusted to select for higher affinity aptamers. Serial washes can be performed to increase purity. FIG. 19C illustrates beads 1903 and 1905 are sorted and the DNA/RNA 1901 bound to pure populations is amplified and process is repeated with the amplified aptamers. Subsequent rounds would focus on individual target molecules but other beads or cells might still be used to identify cross-reactivity of aptamers.

In general, beads with acoustic contrast to a medium can be used as an alternative to magnetic beads for virtually any purification process that magnetic beads are used. Beads used in acoustic separation can generally be made cheaper than magnetic beads. Larger magnetic beads also tend to clump together in a magnetic field and this can trap undesired materials. While few things in biological separations are magnetic and this gives magnetic beads a specificity advantage, the same can be said for negative acoustic contrast beads. Medium switching can also be accomplished for laminar flow systems with magnetic beads. There is utility in combining methods as well, particularly if more than binary separation is required. Three populations can be separated for example, if both negative and positive acoustic contrast particles were combined with magnetic particles.

Example 17

High Speed Valve Sorting

Acoustic medium switching of the present invention provides sorting of in-line washed cells and particles. While an acoustic medium switching module can easily be used with a conventional hydrodynamically focused flow cytometer, this new capability is made even more powerful by sorting methods that can be implemented in a sorting acoustic cytometer. Conventional cytometer sorting can be divided into two groups of instruments, droplet sorters and valve sorters. Most sorting tasks are performed by droplet sorters as they are generally much faster. Valve sorting cytometers do have advantages as they are gentler on delicate cell populations, they are less expensive and tend to operate more reliably without operator intervention. The shortcomings of conventional valve sorting cytometers include relatively slow sorting rates of 300-500 cells per second and dilution of sample with sheath fluid. Dilution with sheath fluid is also an issue for droplet sorters, but this is less problematic as the method allows capture of cells in very small droplets which can be diverted to tubes containing whatever medium is desired. The acoustic cytometer does not require sheath, so the dilutive can be eliminated. Also, since no sheath is required, sorting can be done in a sequential manner without further dilution of sample. For relatively rare cells, this enables a high speed initial valve sort that captures a cell of interest along with other cells for every sort decision. This enriches the ratio of desired cells and lowers the overall population in the sorted fraction. This sorted fraction can then be run again at a slower rate that will enable high purity of cells. If for example, cells are analyzed at a rate of 30,000 cells per second and the valve sort were capable of sorting at 300 cells per second, each initial sort decision should contain an average of about 100 cells. If these 100 cells are then transferred to a second sorter (or the same sorter after the initial sort) at a slower flow rate, the individual cell of interest can then be sorted with high purity. For an acoustic cytometer this repeated sorting can be done without additional sheath dilution and can even be done in an instrument that reanalyzes and resorts in-line (see FIG. 20). Dual or multistage sorting can be accomplished in-line because refocusing of cells or particles after the first sort can be accomplished using another acoustic focusing capillary. A conventional sorter would require a second sheath which would greatly increase fluidic complexity while continuing to dilute the sample.

Figure 20:
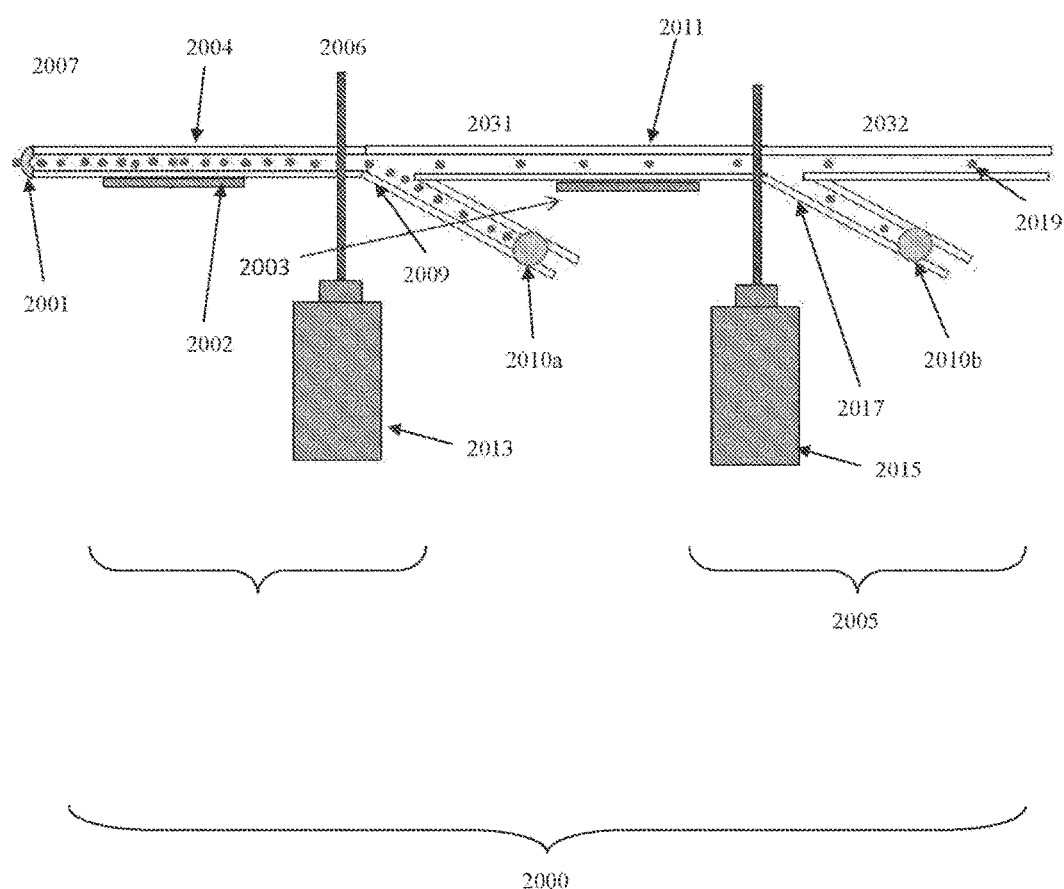
FIG. 20 illustrates an example of a dual stage acoustic valve sorter according to one embodiment of the present invention.

FIG. 20 illustrates an example of a dual stage acoustic valve sorter 2000. This design enables in-line non-dilutive high speed sorting of rare cell populations. While similar "pre-sorting" strategies using repeated serial valve sorts are executed in conventional sorters, the hydrodynamic focusing of these instruments results in serial dilution. Sample 2001 comprising particle 2007 is introduced into part 2001 of system 2000. A first acoustic focusing system 2002 induces an acoustic wave in channel 2004. Interrogation source 2013, for example a light source interrogates the sample and/or particle at an interrogation point 2006. Particle of interest is sorted at 2009 and the unwanted particle is directed to waste 2012 paste valve 2010a. The kept particle or particles are directed or flowed in the stream to the second transducer 2002 where a second acoustic wave can be induced into the channel. The acoustically focused particle 2011 is interrogated at an interrogation point with a light source 2015 and optical information may be collected. A particle can be sorted to waste 2010b or sent for analysis or collection in the system 2019.

An alternative approach enabled by sheathless cytometry is the triggered capture of target cells. In this method a cell population can be analyzed at high speed and when a cell with the correct profile is identified, flow is stopped and the individual cell is collected.

In order for the many benefits of acoustic focusing to be fully realized, it is desirable for particle rates to be maximized for competitive throughput with conventional cytometers. This can be accomplished by adjusting sample concentration in the acoustic cytometer by prior dilution, in-line dilution or acoustic washing or a combination of these methods. For dilute samples, acoustic cytometry already has a distinct advantage, but this can be leveraged further by acoustic pre-concentration or washing prior to analysis.

Prior Dilution

The simplest method for reducing coincident rates in a large diameter acoustically focused channel for concentrated samples is to dilute the sample prior to processing such that the optimum concentration of particles is presented for analysis. Diluting the sample prior to processing gives the user tremendous flexibility in the initial concentration of samples that can be used with the instrument while insuring that the optimum rate of particle analysis for a given flow rate is achieved. Prior dilution can only be used in conventional cytometry for very concentrated samples before decreasing throughput. The particle analysis rates in an acoustic cytometer can be kept high not only because of the concentration effect but because systems have been developed that are capable of very high sample throughputs on the order of several milliliters a minute. It is the high volumetric sample rate possible in acoustic systems that makes this method fundamentally different from prior art methods.

Example 18

For a 300 micron diameter acoustic focusing capillary, a 10 microsecond transit time through the interrogation laser, and a particle rate of 10,000 particles/s, a concentration of about $2.8 \times 10^5$ cells/ml or less is required to achieve a mean event rate of less than one in ten time windows. According to Poisson statistics, this corresponds to a probability of about 1% that a time window will contain more than one event meaning about 10% of events will be coincident. This sample is less than half the concentration than the example above for a conventional cytometer where particle rate was limited to 100 particles per second. The volumetric flow rate required for this 10,000 particle/s rate example is about 2.1 ml per minute. An acoustic cytometer can maintain similar precision of focus to the slow sample rate of a conventional cytometer for cell sized particles at this greater volumetric flow rate.

For an acoustic cytometer with a 300 micron diameter, a concentration of about $2.8 \times 10^5$ cells/ml is optimal for maximum throughput with about 10% coincident events. For larger particles or larger laser beams or if fewer coincident events are desired, a user might choose to reduce coincident events by decreasing concentration. Samples run on an acoustic cytometer with a flow rate of 2.1 ml/min can be diluted up to 210 fold before more time is needed to process the sample than for a conventional cytometer running with a sample rate of 10 µl/min. Thus, with simple up-front dilutions, an acoustic cytometer can operate at higher throughput than a conventional cytometer for concentrations up to about $6 \times 10^7$ cells/ml. For higher concentrations, throughput cannot be increased beyond the maximum particle rate of a given instrument.

The $6 \times 10^7$ cells per ml concentration sample can be conventionally processed at a maximum rate of 1000 cells/s. An input rate of approximately 10 µl/min is typically diluted about 20 fold to reach the optimum concentration for an acoustic cytometer. By running at 2 ml/min, particles are analyzed at nearly 10 times the rate of a conventional cytometer. If a user prefers to take advantage of longer transit times through the laser, a sample could be slowed to 0.2 ml per minute where it would have similar particle analysis rates to the conventional cytometer but with much longer transit times.

Prior dilution of samples with concentrations greater than an optimal concentration for a given acoustic cytometer allows the use of nearly any concentration of starting sample and it allows pre-treatment of buffers in any number of ways including adding reagents or changing acoustic contrast, dissolved gas content or temperature. It also conveys other valuable assaying benefits. Among these are background reduction from unbound labeled ligands and decreasing the minimum size sample required.

Background Reduction

When staining cells or particles with fluorescent antibodies or other ligands, it is desirable to bind as much of the ligand to the target as possible while leaving as little as possible in solution. The remaining labeled ligand causes fluorescent background that reduces the signal to noise ratio during analysis.

It is usually advantageous to do the staining in a small concentrated volume to favor binding kinetics. Simply diluting the sample reduces the concentration of unbound antibody and therefore the background signal during analysis. Dilution is not generally performed in conventional cytometry because it decreases particle rate thereby increasing analysis time. For many samples in cytometry, the cell concentration is already greater than a typical optimum concentration for an acoustic cytometer.

After staining, centrifugation followed by resuspension in a new buffer or medium is often performed to eliminate unbound ligands. This can still be done for an acoustic cytometer but it can also be coupled to dilution by simply adding more buffer. This process makes the unbound ligand concentration even less than with centrifugation alone.

Sample Size

Conventional cytometers usually require volumes on the order of a few hundred microliters to function properly and often some of the sample cannot be analyzed when the level runs low. Even newer cytometers with smaller sampling capabilities boast a minimum sample volume of 10-25 µl. Using dilution, nearly any starting volume is possible in an acoustic cytometer of the present invention. For example, the 210 fold dilution factor mentioned above makes a 1 µl sample into a 210 µl sample which can easily be processed with an acoustic cytometer using standard sample tubes.

One embodiment of the present invention comprises very small samples in microtiter plates. Well plates typically only have a maximum volume up to about 20 µl so dilution of a 1 µl sample can only be done up to 20 fold. If however, diluent is fed to the well while the sample is being fed to the cytometer, a higher fold dilution can be accomplished.

Kinetic Dilution

The rapid volumetric processing rate of an acoustic cytometer of the present invention also allows dynamic experiments on time scales that conventional cytometers cannot achieve. If a diluent containing a reagent(s) or drug candidate is mixed with a sample just prior to analysis, processes triggered by this reaction can be monitored for the entire sample over a very short time period. If for example a 10 µl sample of cells with a starting concentration of $2 \times 10^6$ cells per ml is primed with probes for monitoring calcium activation, and 90 µl of diluent containing a calcium activator or test compound is added just prior to analysis, the entire sample can be analyzed in an acoustic cytometer in approximately 6 to 30 seconds at a flow rate of 1 to 0.2 ml/min. For the same sample in a conventional cytometer, it would take at least 60 seconds to analyze with no dilution at the cytometer's top, less precise sample rate.

One advantage of the large dilution that is allowed in acoustic cytometry of the present invention is that rapid mixing can easily be accomplished. This ensures that all cells have equal exposure to the reagent and the cell reaction over time can be more accurately monitored.

Combining Pre-Dilution with in-Line Dilution

While prior dilution has many advantages, it is also sometimes desirable to combine predilution in the present invention. One example is when a large volume of concentrated sample must be processed from a small sample tube. A 1 ml sample with $2 \times 10^7$ cells per ml needs to be diluted in a conventional cytometer 100 fold to achieve a 10% coincidence rate and this requires a 100 ml sample volume. With an acoustic cytometer, it is possible to drastically change the in-line dilution from nothing to ratios of diluents to sample similar to conventional hydrodynamic focusing without degrading the precise focus.

A variable diluent can be employed with pre dilution such that virtually any combination of acceptable coincidence is achieved. For the example above, if a 10 µl sample tube were available, 10 fold predilution could be combined with 10 fold in-line dilution, or 5 fold pre-dilution might be employed with 20 fold in-line dilution to accomplish the same thing.

The sample inputs can be configured in a number of ways for in-line dilution. If the sample flows in the center of the flow cell for acoustic focusing, and the diluents surround it coaxially, some of the benefit of unbound probe dilution will be lost but the in-line diluents will keep the sample from contacting the walls and will also force particles into starting positions in the flowed where the acoustic gradient is higher. This allows greater throughput and better focusing of smaller particles.

In-line acoustic washing of particles can also be employed to the same effect if the sample fluid is of lesser acoustic contrast than the diluent's fluid. In this case, depending on the initial flow configuration, the sample fluid itself moves toward or is maintained at the walls of the focuser, while the particles or cells are retained at or are moved to the central focus.

Combining Analysis with Off-Line Acoustic Washing/Concentration

In another embodiment of the present invention, analysis can be done after acoustic washing and/or acoustic concentration is performed offline. In an acoustic washer/concentrator cells or particles can be concentrated many fold while discarding most (concentration) or nearly all (washing) of the original medium. This is of course of particular utility when the original concentration is sub-optimal for the desired particle analysis rate, but it is also of great utility for samples with very high background or for samples that require a high degree of background reduction.

Once a sample is washed or concentrated, it can then be diluted or not depending on concentration and desired particle coincidence vs. analysis rate. It is often difficult or impractical to keep careful track of the precise concentration of a sample so a user may employ an aid such as a spectrometer to determine concentration based on light scatter. Alternatively, another embodiment of the present invention includes an on-board spectrometer that can calculate the proper dilution and possibly also execute the dilution automatically. Still another embodiment of the present invention, allows a user to take a portion of the sample or a diluted portion and run it on the instrument to determine concentration and dilution prior to the main analysis.

Transit Time Advantage

For a conventional cytometer, transit times through an interrogation laser are usually about 1-6 microseconds. With an average event rate of 0.1 per unit time, 10 microseconds corresponds to an analysis rate of 10,000 particles per second. For acceptable coincidence and an event rate of 1000 particles per second, an acoustic system of the present invention can accommodate transit times of 100 microseconds, a range that greatly improves photon statistics and opens the field of application for the longer acting photoprobes.

Assaying for cells, particles and microbes can be improved using acoustic focusing with the pre-dilution method, in-line dilution method or in-line or offline acoustic concentration or washing method or combinations thereof. Both assaying with higher sensitivity/resolution and novel assaying made practical by acoustic cytometry greatly expand the capability of analysis in flow.

General examples of assaying that can use acoustic cytometry according to embodiments of the present invention include, but are not limited to cell sorting, apoptosis analysis, cell cycle studies, fluorescent protein detection, cell proliferation assaying, immunophenotyping, antigen or ligand density measurement, gene expression or transfection assaying, viability and cytotoxicity assaying, DNA/RNA content analysis, multiplex bead analysis, stem cell analysis, nuclear staining detection, enzyme activity assaying, drug uptake and efflux assaying, chromosome analysis, membrane potential analysis, metabolic studies and reticulocyte and platelet analysis among others. Assaying can be improved using acoustic focusing fluid reorientation or a combination thereof using an acoustic cytometer with the additional steps of adjusting to the desired optimal throughput concentration through prior dilution, in-line dilution and or acoustic washing and selecting the appropriate transit time for best results. In addition, an acoustic cytometer that has slow or stopped flow imaging capabilities provides additional flexibility and advantage. Additionally, off-line concentration can improve throughput where cell concentrations are sub optimal. Off-line acoustic washing can also replace most centrifugation steps or can be added as a background reducing step.

Non-Compensation Protocols

An embodiment of the present invention comprises a method for reducing compensation in an acoustic cytometer. This embodiment includes flowing particles with at least 2 fluorescent labels through the acoustic cytometer and collecting fluorescent signals from the particles as they pass an interrogation point. Then overlap from different color fluorescent labels is reduced by using at least one fluorescent band filter with a narrowed band pass such that signal from at least one fluorescent label emission is reduced. The transit time is then slowed by reducing the flow rate such that at least as many photons are collected from the reduced signal as when the wider band pass filter is used with a faster transit time. Assaying of this embodiment preferably uses at least 2 fluorescent labels and can run without running compensation controls and without compromising results.

Analysis of Microbes

Analysis of very small particles and cells is a considerable challenge for conventional cytometry. Quantities of proteins and DNA are on the order of 3 orders of magnitude smaller then for organisms such as bacteria. The longer transit times in acoustic cytometry improve microbe analyses by improving the photon statistics of these dim measurements. This improvement provides for many new methods of microbe analysis in an acoustic cytometer that could not commonly be measured in conventional cytometers.

Reductions in instrument cost that are made possible by acoustic cytometers also make routine counting and live/dead type analyses of microbes much more accessible to more researchers.

Low cost analysis for mammalian cells may be done with the present invention, beyond counting and viability such as apoptosis and cell proliferation.

Methods for Increasing Dynamic Range

Increasing dynamic range can be important for assaying in which there is a wide range of signal intensity, there are increasing numbers of distinguishable populations in a bead set and using detectors that have a more limited dynamic range. Photo-multiplier tubes are dominant in cytometry. They have a wide dynamic range but lower quantum efficiency than some lower dynamic range detectors including but not limited to avalanche photodiodes (APDs). Multi-pixel APD devices known as silicon PMTs may also be used in the present invention.

With the long transit times in an acoustic cytometer, greater dynamic range is available than in fast transit time systems because of the added dimension of time. Two lasers of different power and different spatial location may be used to analyze the same particle twice. The stronger laser is used to quantify the dim particles while the weaker laser is used for stronger particles. For a longer transit system, a similar increase in dynamic range can be realized by using a single weaker laser, increasing transit time and measuring pulse area (integrated signal from photons). Alternatively, instead of, or in addition to, measuring peak height, the rate of signal increase or decrease of the pulse can be measured. For a large signal, if this information is taken prior to detector saturation, the expected brightness can be calculated rather than measured. This method is particularly useful for beadsets with set ratios of coding labels as the ratio(s) of rate increase can be used to decode the population without regard to intensity. Also, an extremely wide range of staining concentrations can be used without saturation of the detector.

The longer transit times also make increased dynamic range from a single modulated or pulsed system more practical. In a modulated system, dim particles are measured at peaks and bright particles are measured at valleys. To use a single laser for a pulsed system both stronger and weaker pulses need to be administered at different times. For a pulse rest method, this is practical for long transit times but not short transit times where the rest period is a significant fraction of the transit time. In a pulsed system, peak intensities can be very high and can damage certain types of photodetectors, so care must be taken in photodetector selection.

Still another method for increasing dynamic range is decreasing the color bandwidth of filters. The most common example of this is a linear detector array in a spectrometer used in conjunction with a dispersive element including but not limited to a grating or prism. While this limits the number of photons per detector and therefore decreases precision due to photoelectron statistics, it allows brighter signals without saturation and can also be used to reduce compensation requirements in multi-color assaying and reduce signal to noise by collecting a higher ratio of signal light to background light. If for example one constructed assaying using AlexaFluor® 405 and Qdots®: 545, 585, 655 and 800, there would be some spectral overlap of fluorophores but uncompensated detection can be used if some narrow band pass filters were to be used.

Multi-Parameter Detection

Acoustic cytometry according to systems and methods of the present invention not only adds to dynamic range but it can add dimensions to assaying multiplexing by allowing enough time for other optical phenomena to be monitored, including but not limited to luminescence and/or chemi/bio/electrical luminescence. With the previous example, if a metal ligand complex including but not limited to europium chelate is a sixth label and a pulsed light source, the first five colors can be monitored just after the pulse and the Europium can be measured throughout its decay lifetime of several hundred microseconds. The narrow primary emission of the europium at 613 nm overlaps some with the emission spectra of the 585 and 655 Qdots® but it would not be detected in these channels if a narrow emission bandpass filter is applied to the Qdot channels. With this combination, six colors are possible with virtually no compensation. In general, long emission fluors can be automatically compensated for even if there is bleed over because relative contributions can be determined on the basis of time and can be subtracted appropriately. Given the complexity of controls and computing power required in typical six color flow assaying, an embodiment of the present invention provides for compensation free or minimal compensation reagent kits, even down to two colors.

Assaying is often processed in a single sample, multi-parameter detection can have great utility. Short lived fluorescence intensity beads can be used as an assaying identifier and long lived fluorescence lifetime as a reporter. With longer transit times and optimized throughput, there are many useful applications. If, for example several shorter lived probes are incorporated into a beadset with varying intensities, the number of possible combinations is such that the beadset can compete with conventional high density nucleic acid arrays. With luminescent reporters, very high sensitivity is possible even with highly fluorescent beads. Additionally, the combination of Qdots® and metal ligand complexes can be efficiently excited with a single violet source including but not limited to a 375 nm laser diode.

Autofluorescence Correction

Auto-fluorescence is often a problem for sensitive detection of small numbers of labels. It has fairly broad emission and can spill over into many channels. In multi-colored applications, it adds another parameter that must be compensated outside of the multiple labels to be used. Just as longer transit times can help improve coefficients of variation for labels with better photoelectron statistics it can also help reduce variance from background such as auto-fluorescence. The net result is that signal to noise ratio is improved as the variance of both signal and background is narrowed.

Auto-fluorescence subtraction has been demonstrated using two lasers. The first laser excites auto-fluorescence above the wavelength of the excitation laser, and the signal detected above that wavelength is used to estimate the auto-fluorescence contribution expected for the primary detection laser. Auto-fluorescence can be done with a system having a violet laser and a blue laser. It can also be done with a system that has only a violet laser or is using a violet laser to excite more than one color, if there is a separate color band to monitor the auto-fluorescence. Only the blue fluorescence channel is monitored, and expected contribution in other channels is subtracted. For pulsed or modulated systems with long lifetime probes, the short lived contribution of the auto-fluorescence combined with the initial output of the long lifetime probe is measured. Fluorescence of the long lifetime probe after the auto-fluorescence has decayed is also measured and back calculated to determine the auto-fluorescence contribution in all channels.

Example 19

Four color assaying with only auto-fluorescence compensation can be performed using four different Qdots®: 525, 585, 655 and 800 and a single violet diode laser. These Qdots® have very little spectral overlap and can be easily separated. If a second laser, including but not limited to an inexpensive diode such as 650 nm or 780 nm is added, other combinations that are virtually compensation free can be added with even more colors. For example, Qdots® 525, 565, 605, 705 and AlexaFluor750 which is excited very efficiently at 780 nm can be added. The 800 Qdot® is not chosen in this case as it has some excitation at 780 nm. For this five color combination, narrow band filters are used to prevent overlap between Qdots®. If elimination of compensation is not critical, similar strategies for employing low cost diodes can be used effectively with more conventional dye combinations such as pacific blue AlexaFluor405®/Cascade Blue® and pacific Orange® off the violet diode and APC and APC AlexaFluor®700 off a 650 nm diode. Alternatively, 473 nm DPSS blue lasers are reasonably inexpensive when they have RMS noise levels of a few percent or more. The long transit times afforded by an acoustic cytometer enable noise integration that can make these lasers attractive. These lasers can then be used in place of the most common 488 nm wavelength lasers where they are capable of exciting the most common fluorophores. Green DPSS modules e.g. (532 m) are even less expensive and less noisy and can be used to excite PE and its conjugates more effectively than even the 488 nm wavelength. In a system where emissions off of each laser are kept distinct, either by spatial or temporal separation, one can use several colors from each laser. If the pulse/rest method is used, lasers can be co-located and fired in sequence. Fluorophores that have little absorption in bands that are being pulsed are still able to rest. If, for example, the rest period is one microsecond and four different lasers are used with 10 ns pulses, each laser is triggered every microsecond with a pulse of a different wavelength hitting the target every 250 ns. A second low power pulse for each laser can be used to extend dynamic range (brightest signals are quantified from the low power pulse, dimmest from the high power pulse). Using lasers at 405 nm, 532 nm, 650 nm and 780 nm four colors and autofluorescence can be monitored with virtually no compensation: 405 nm-autofluorescence and Pacific Orange, 532 nm-PE or Cy®3, 635 nm-AlexaFluor®647 and 780 nm-AlexaFluor®790. There is some excitation of PE at 405 nm and some excitation of AlexaFluor®790 at 635 nm so slight compensation might be required. If compensation need not be eliminated, several colors can be excited off of each laser. With lasers collocated but separated temporally, one can use the same detectors where dye emissions from fluorophores excited by different lasers overlap.

Many of the 405 nm violet laser diodes are typically high quality with low noise. Since these diodes can be obtained inexpensively with high pulsed powers, they useful for implementing high power pulses with long rest times. The diode wavelength of the 405 nm violet laser can be very useful with or without pulses when coupled with long transit times. It is very efficient for excitation of quantum dots which is useful for many-colored assaying. This, coupled with narrow band emission filters, is useful for assaying with little or no need to compensate.

Example 20

Method for Luciferase Mediated Gene Detection in an Acoustic Cytometer

Another embodiment of the present invention provides form bio or chemiluminescence in an acoustic cytometer and the detection of gene expression, for example, using luciferase as a gene reporter. While gene expression detection can be accomplished with other means such as fluorescent protein expression, bio/chemi luminescence adds an additional parameter that can be separated in time from this or other flow cytometry fluorescence parameters. Light generated by the reaction of gene expressed luciferase and its substrates luciferin (or coelenterazine for *Renilla* luciferase) does not require external excitation and is therefore free of autofluorescence excited in the cell, flow cell or detection optics. This also makes luciferase especially useful for detection of low level gene expression where signal to noise is especially important. In general, cells expressing luciferase are loaded with luciferin which is generally cell impermeant except for specialized reagents such as caged DMNPE luciferin which can be loaded into the cell by incubation. They are then supplied ATP which completes the light producing reaction. For DMNPE luciferin can be uncaged using UV light.

Using an acoustic cytometer with a pulsed excitation system, it is possible to sensitively monitor the chemiluminescence between laser pulses. Standard fluorescence flow cytometry parameters can be collected as desired to determine cell characteristics including cell surface markers, detection of fluorescent protein gene expression, calcium activation, nucleic acid analysis and so forth.

Luciferase Antibodies and Secondary Reagents

Luciferase can also be conjugated to antibodies and secondary reagents like protein A and G. Avidin and streptavidin recombinant protein A and streptavidin luciferase fusion proteins have also been developed. These reagents can be used to label cellular antigens or bead bound targets in order to add an additional parameter for analysis in acoustic cytometers. With an acoustic wash containing luciferin and ATP, systems with pulsed lasers can detect the luminescence between pulses and subtract this quantity of light from overlapping spectra of fluorophores used to measure other targets. This is especially useful for multiplex beads sets that rely on fluorescence for coding. It is also especially useful for measuring low levels of antigens on cells with high autofluorescent background. In addition, luciferase can be used in conjunction with any laser combination or even in the absence of lasers as it does not require excitation light.

Materials for Engineered Acoustic Media

According to another embodiment, methods of acoustic washing particles and reorienting fluid utilize media formulations that have higher acoustic contrast than the sample medium. For many biological samples the medium is buffered saline, often with protein, detergents or other additives. Many media with higher acoustic contrast than physiological saline have been developed for use in density gradient separations by centrifugation. The functional constituents of these media are salts and proteins combined with additives used to increase specific gravity without undue increase in salinity. Commonly used examples include sucrose, polysucrose, polydextran, glycerol, iodinated compounds like amidotrizoate, diatrizoate, iohexol (Nycodenz®), iodixanol, ioxaglate, iopamidol, metrizoate, metrizamide, and nanoparticulate material such as polymer coated silica (Percoll® for example). In applications where high salinity is not a problem, the primary constituent is a heavy salt such as cesium chloride or potassium bromide.

For acoustic separations density and osmolarity are important but additional parameters such as compressibility and viscosity are more important than for centrifugation media. This makes the priorities for formulation of acoustic separation media different. Viscosity is of higher concern than for centrifugation as higher viscosity dissipates more acoustic energy relative to lower viscosity. Therefore, compounds that contribute to high viscosity are not preferred unless required by the application. In general sucrose/polysucrose, glycerol and dextran fit into this category. Nano silica coated with polyvinylpyrrolidone is also highly viscous and fluorescent as well. Preferable compounds to be added include the iodinated compounds above and are preferably selected not only on the basis of contribution to viscosity and osmolarity but also on compressibility. Metrizamide, Nycodenz®, diatrizoate and iodixanol are useful for altering the acoustic contrast of a fluid.

In preparations where physiological osmolarity is desired but short term loss of physiological ions will not be important, a heavy salt, such as cesium chloride but not limited thereto, can be substituted or partially substituted for other salts such as sodium chloride. Cesium chloride provides a benefit not only because it is an innocuous and relatively heavy but because it reduces viscosity of the medium. A cesium chloride solution with physiological osmolarity has about 3% lower viscosity than a comparable sodium chloride solution. This is an advantage for acoustic separations according to one embodiment where higher viscosity absorbs more acoustic energy.

Cesium chloride is useful for acoustic separations that can tolerate high salt such as separations of fixed cells and beads. High salt acoustic wash buffer combined with additives such as protein and surfactant or detergent can be used to minimize nonspecific binding in both protein and nucleic acid assaying. One preferred embodiment uses cesium chloride and a Pluronic® non-ionic surfactant such as Pluronic® F68. The Pluronic® has very low auto-fluorescence and is therefore well suited to flow analysis.

Beads with Lifetime Auto-Calibration

A difficult problem for assaying in flow cytometry is absolute quantification of analytes from instrument to instrument and day to day or even minute to minute. Differences in laser power and fluctuation, PMT adjustments and degradation and flow alignment are among the worst culprits in variability. Absolute quantification must typically be done using calibration beads that excite and emit in the same channels as the analyte to be detected. An alternative to this procedure can be accomplished in an acoustic cytometer with lifetime discrimination capability using beads loaded with a known amount of long lifetime fluorescent dye (preferably greater than 1 microsecond). The long lifetime dye is excited simultaneously with the analyte probe and after short-lived fluorescence dies down (typically 1-100 $\mu s$), the remaining signal of the long lifetime probe can be used to calculate the signal of the analyte probe. The initial signal of the long lifetime probe is calculated from the known lifetime curve of the dye and is subtracted from the combined fluorescence peak of the analyte probe and the long lifetime dye. Alternatively, if the analyte is probed with a long lifetime dye the bead reference dye can be short lived. Absolute calibration is easiest when the analyte and reference dye are excited by the same laser and detected by the same detector so the probes need to be selected with this in mind. The commonly used lanthanide chelates are generally UV excited so their utility is limited in systems with visible lasers. Other suitable candidates include but are not limited to metal ligand complexes using metal ions such as europium, terbium, samarium, iridium, ruthenium, neodymium, ytterbium, erbium, dysprosium, platinum, palladium, and gadolinium. The excitation, emission and lifetime properties of metal ligand complexes are dictated by the metal ion and its ligand. Coupling different ligands to different ions and/or modifying ligand structure has been and continues to be heavily researched. A wide variety of possibilities are available for tuning of lifetime and excitation and emission wavelengths.

In one embodiment of the present invention, reference beads can be formulated for any of the systems described previously by combining compatible optical parameters. For example absorptive dyes can be used for coding while a short-lived fluorescent dye is either used for reference or detection and a long-lived dye is used for reference or detection. A UV excitable short lifetime dye including but not limited to Pacific Orange®, or a quantum dot and long-lifetime probes including but not limited to terbium chelates or europium chelates or tandems thereof, are good choices for single source excitation of the reference and detection components. Absorptive dyes can be selected from a wide list of non-fluorescent species but they preferably absorb in spectral regions away from the reference and detection probes excitation and emission such that even very heavily dye loaded beads do not absorb the excitation or emission light. Good choices would absorb in the infrared or near infra-red region. Low cost diode lasers in this spectral range make this choice even more attractive. In this spectral region it also works well to use fluorescent dyes including but not limited to AlexaFlour®647 and AlexaFluor®790 for their absorption properties only since the emission wavelengths do not interfere with the coding and detection regions.

Another use is quantum dots as coding labels and terbium or europium chelates for detection with either one of the quantum dots as a reference or another organic UV excitable dye as reference. In this case the AlexaFluor®405, for example, can also function in the detector role. Qdot®545 can be used in conjunction with terbium chelate and Qdot®625 can be used in conjunction with europium chelate. Many combinations are useful with a single violet excitation source.

Still another example of reference beads that can be formulated for any of the systems described previously uses Ruthenium ligand complexes for the reference and a common fluorophore for the reporter such as PacificBlue® or PacificOrange® or Qdots® with violet excitation and or fluorescein/AlexaFluor®488, PE/PE conjugates or PerCP/PerCP conjugates with violet or blue excitation. The ruthenium ligand reference of this embodiment of the present invention has relatively broad band emission and is well excited by both violet and blue lasers. It can therefore be monitored in the same channels as many common fluorophores. Using different colored analyte reporters simultaneously is also possible and permits either simultaneously monitoring more than one analyte on one bead or increasing the size of the multiplex array by using differently tagged reporters for different analytes. A 20 analyte array can be made for example using a single coding color (e.g. Qdot®800) of 10 different intensities if 2 reporters are used (e.g. PacificBlue® and PE). The single color array can be expanded to 40 elements if for example 2 colors of reporters are monitored from each laser.

As DNA content in cells in resting phase can be very consistent, antigenic markers on cells can also be quantified relative to a fluorescent DNA stain by using pulsed excitation and measuring the overlap in signal over time with long-lifetime probes used to stain the antigenic markers. Effects not related to excitation that might cause variation in the DNA stain fluorescence relative to fluorescence of the antigenic probes should be minimized. These include temperature, pH and dye loading effects.

Referencing to a DNA stain can similarly be done with long-lifetime DNA probes and short lifetime antigenic probes given an appropriate DNA stain.

Lifetime coding can also be combined with lifetime reference if the emission colors or the excitation of the long-lifetime elements can be well separated. If for example, terbium chelate and a short lifetime UV excited dye are used for coding and ruthenium is used for reference, UV excitation light can be used for coding while violet and or blue light is used for reference and analyte detection.

One embodiment of the present invention comprises a method for quantifying an amount of analyte bound to a particle in an acoustic particle analyzer. This method preferably includes manufacturing a particle having a known amount of calibration dye with a long lifetime and a specificity for an analyte. The analyte is bound to the particles and passes the particle through an interrogation zone with a pulsed or modulated laser. The short-lifetime fluorescent signal which relates to the binding event in the interrogation zone is measured and the overlapping fluorescent signal is measured from the long lifetime reference probe. The amount of analyte is then preferably calculated by comparing the analyte related signal to the signal from the known amount of reference label. The analyte related signal is preferably generated by binding a fluorescent ligand specific for the analyte to the analyte such that the particle and analyte and fluorescent ligand form a complex.

Another embodiment of the present invention comprises a method for quantifying the amount of analyte bound to a particle in an acoustic particle analyzer. In this embodiment, a particle is manufactured having a known amount of calibration dye with a short lifetime and a specificity for an analyte. This analyte is bound to the particle and passes the particle through an interrogation zone with a pulsed or modulated laser. A long lifetime fluorescent signal that is related to the binding event in the interrogation zone is measured and the overlapping fluorescent signal from the short lifetime reference probe is also measured. The amount of analyte is then calculated by comparing the analyte related signal to the signal from the known amount of reference label. The analyte related signal of this embodiment is preferably generated by binding a fluorescent ligand specific for the analyte to the analyte such that the particle and analyte and fluorescent ligand form a complex.

Environmental and Industrial Applications

In one embodiment of the present invention, acoustic concentration and washing can be used for sample treatment and analysis in a range of environmental and industrial samples, particularly where particles of interest are rare and require significant concentration to acquire a statistically meaningful population. The ability of acoustic concentrators to function as "filterless filters" that are not subject to clogging and periodic replacement requirements makes them very attractive in many applications. Analysis of microbes from municipal water supplies is a prime example. Specific nucleic acid probes and other microbe specific probes are used to confirm the presence of microbes in water samples but pre-concentration before staining is necessary to limit the amount of staining reagent and to process enough volume to be statistically significant. Similar microbial testing is done for a multitude of industrial products and foods from juice, milk and beer to mouthwash and these analyses can also benefit tremendously from acoustic concentration. Acoustic washing can be employed to separate environmental and industrial analytes from reagents such as the staining probes for more sensitive measurements and can also be used to replace the original sample medium with fluids containing different reagents or compositions. Acoustic washing using electrolyte buffer for impedance analysis is of particular utility for virtually any sample including those listed above which does not have the required conductivity for analysis. In an acoustically focused imager, analysis can extend to shape and size of particles which is important for a great deal of industrial processes as diverse as ink production for copiers and printers and quality control in chocolate making. Acoustic focusing and alignment of particles greatly enhances quality of imaging of particles by bringing particles into focus at the focal imaging plane and also orienting asymmetric particles with respect to the acoustic field. Acoustic focusing can be used to concentrate and/or remove particles from waste streams or feed streams. An acoustic focusing apparatus can be placed in-with other filtration systems, e.g. water purification systems, to extend the life of the filters. Such processing is not just limited to aqueous environments, removal of metal, ceramic or other particulates from machining fluids or particulates from spent oils such as motor oils and cooking oils is also possible.

Any of the methods above can be automated with a processor and a database. A computer readable medium containing instructions can preferably cause a program in a data processing medium (a computing system) to perform a method.

The preceding examples can be repeated with similar success by substituting the generically or specifically described components and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A particle analyzing system, comprising:
a flow cell configured to receive a sample stream that comprises a plurality of particles;
an acoustic device configured to acoustically focus at least some of the particles within the flow cell;
a fluidics system configured to hydrodynamically focus at least some of the plurality of particles within the flow cell;
a controller configured to automate an aspect of the particle analyzing system operation; and,
a monitor configured to monitor at least some of the plurality of particles,
the system being configured to, during operation, effect acoustic particle focusing and hydrodynamic particle focusing within the flow cell.

2. The particle analyzing system of claim 1, wherein the monitor comprises an imager.

3. The particle analyzing system of claim 2, wherein the imager is configured to capture a plurality of images, wherein the images are used to create a high content image.

4. The particle analyzing system of claim 3, wherein a sampling matrix of particles taken from subpopulations of a particle population is used to create the high content image.

5. The particle analyzing system of claim 1, wherein the monitor comprises a detector.

6. The particle analyzing system of claim 5, wherein the detector is a CCD.

7. The particle analyzing system of claim 1, further including a light source configured to illuminate at least some of the plurality of particles for monitoring.

8. The particle analyzing system of claim 1, wherein a user defines a threshold for monitoring.

9. The particle analyzing system of claim 1, wherein system is configured to monitor a particle of the plurality of particles more than once.

10. The particle analyzing system of claim 2, wherein the system is configured to image, at the same time, more than one particle of the plurality of particles.

11. The particle analyzing system of claim 1, wherein the fluidics system is configured to deliver a sheath fluid to the flow cell.

12. The particle analyzing system of claim 1, wherein the fluidics system is configured to deliver a sample fluid including at least some of the plurality of particles to the flow cell.

13. The particle analyzing system of claim 1, wherein the system is configured to decrease, reverse, or stop a particle velocity for monitoring.

14. A particle analyzing system, comprising:
a flow cell configured to receive a sample stream that comprises a plurality of particles;
an acoustic device configured to focus at least some of the particles within the flow cell;
a fluidics system configured to deliver a sheath fluid to the flow cell;
a controller configured to automate an aspect of the particle analyzing system operation; and
an imager,
the system being configured to, during operation, effect acoustic particle focusing and hydrodynamic particle focusing within the flow cell.

15. The particle analyzing system of claim 1, wherein the particle analyzing system is configured to focus at least some of the plurality of particles toward the center of the flow cell.

16. The particle analyzing system of claim 14, wherein the particle analyzing system is configured to focus at least some of the plurality of particles toward the center of the flow cell.

17. The particle analyzing system of claim 1, wherein the controller is configured to operate the acoustic device.

18. The particle analyzing system of claim 14, wherein the controller is configured to operate the acoustic device.

19. The particle analyzing system of claim 14, wherein the controller is configured to adjust a flow rate of the sample stream.

20. The particle analyzing system of claim 1, wherein the controller is configured to adjust a flow rate of the sample stream.

* * * * *